US012251242B1

(12) United States Patent
Vakili et al.

(10) Patent No.: US 12,251,242 B1
(45) Date of Patent: Mar. 18, 2025

(54) VOICE-BASED METHOD AND SYSTEM FOR MANAGEMENT OF TYPE 2 DIABETES

(71) Applicant: UpDoc Inc., Los Altos, CA (US)

(72) Inventors: Sharif Vakili, Los Altos, CA (US); Ashwin K. Nayak, Mountain View, CA (US)

(73) Assignee: UpDoc Inc., Los Altos, CA (US)

( * ) Notice: Subject to any disclaimer, the term of this patent is extended or adjusted under 35 U.S.C. 154(b) by 39 days.

(21) Appl. No.: 18/384,321

(22) Filed: Oct. 26, 2023

Related U.S. Application Data

(60) Provisional application No. 63/545,542, filed on Oct. 24, 2023.

(51) Int. Cl.
A61B 5/145 (2006.01)
A61B 5/00 (2006.01)
G16H 40/67 (2018.01)

(52) U.S. Cl.
CPC .......... A61B 5/7465 (2013.01); A61B 5/0004 (2013.01); A61B 5/0022 (2013.01); A61B 5/14532 (2013.01); A61B 5/741 (2013.01); A61B 5/749 (2013.01); G16H 40/67 (2018.01)

(58) Field of Classification Search
None
See application file for complete search history.

(56) References Cited

U.S. PATENT DOCUMENTS 10,007,760 B2 6/2018 Bielawa et al.
10,272,198 B2 4/2019 Bashan et al.
11,302,448 B1 4/2022 Jain et al.
11,322,260 B1 5/2022 Jain et al.
11,342,051 B1 5/2022 Jain et al.
11,367,519 B1 6/2022 Heldman et al.
11,369,297 B2 6/2022 Wu et al.
11,456,080 B1 9/2022 Jain et al.
11,504,011 B1 11/2022 Jain et al.
11,862,303 B1 1/2024 Gershoni et al.
11,901,059 B2 2/2024 Pugsley
2017/0329917 A1* 11/2017 McRaith ................ G16H 40/67
2018/0272066 A1 9/2018 McMahon et al.
2018/0277246 A1* 9/2018 Zhong .................... A61B 5/746
2019/0043501 A1 2/2019 Ramaci
2020/0276088 A1 9/2020 Valentine
2021/0212606 A1 7/2021 Tran
2022/0115133 A1 4/2022 Mason et al.

(Continued)

FOREIGN PATENT DOCUMENTS

WO 2022169856 A1 8/2022

Primary Examiner — Aurelie H Tu
(74) Attorney, Agent, or Firm — Gregory Finch; Finch Paolino, LLC

(57) ABSTRACT

An artificially intelligent, voice-based method for prescribing, managing and administering at least one medication for management of type 2 diabetes to a patient. Aspects of the present disclosure provide for a system and method for configuring one or more clinical algorithms according to one or more clinical protocols to configure a conversational AI model. The conversational AI model is configured to drive a conversational AI agent configured to facilitate a plurality of multi-turn conversational interactions between a patient user and the conversational agent to enable automated initiation and titration of one or more diabetes medications for the patient.

11 Claims, 17 Drawing Sheets

(56) References Cited

U.S. PATENT DOCUMENTS

| | | |
|---|---|---|
| 2022/0133224 A1 | 5/2022 | Bashan et al. |
| 2022/0328153 A1 | 10/2022 | Lavender |
| 2023/0008055 A1 | 1/2023 | Hoar et al. |
| 2023/0285745 A1 | 9/2023 | Hogg et al. |
| 2023/0298754 A1 | 9/2023 | Bitetti |
| 2024/0062859 A1 | 2/2024 | Gnanasambandam et al. |

* cited by examiner

VOICE-BASED METHOD AND SYSTEM FOR MANAGEMENT OF TYPE 2 DIABETES

CROSS-REFERENCE TO RELATED APPLICATIONS

This application claims priority benefit of U.S. Provisional App. Ser. No. 63/545,542, filed Oct. 24, 2023, entitled "ARTIFICIALLY INTELLIGENT SYSTEM FOR MEDICATION MANAGEMENT"; the entirety of which is hereby incorporated herein by reference.

FIELD

The present disclosure relates to the field of systems and methods for management of type 2 diabetes; in particular, an artificially intelligent, voice-based system and method for remote management of type 2 diabetes.

BACKGROUND

Nearly a quarter of the 33 million US adults with type 2 diabetes have poor glycemic control with hemoglobin A1c above 8%. Medication management with oral therapies, biologics and/or insulin is essential for poorly controlled diabetes, but effective management requires frequent medication adjustments and dose titrations. This can be challenging to achieve in practice as these adjustments typically only occur at outpatient clinic visits generally scheduled every three to six months. Additionally, many providers fail to follow through on adjustments when indicated due to therapeutic inertia, lack of time and competing demands in appointments. With the shortage in provider labor and ever-increasing patient demand due to demographic shifts, certain prior art solutions have emerged to help support patients to manage their medication and care in a home setting or other non-clinical setting.

Innovations that have emerged to help support diabetes management include mobile apps and remote patient monitoring (RPM) devices. These solutions are designed to scale care management teams of nurses, pharmacists, and other support staff, and improve medication support and adherence. Historically, most of these tools have focused on diabetes education, medication reminders and tracking health data, but there is a growing number of mobile applications and devices that also provide real-time decision support for medication self-management.

SUMMARY

The following presents a simplified summary of some embodiments of the invention in order to provide a basic understanding of the invention. This summary is not an extensive overview of the invention. It is not intended to identify key/critical elements of the invention or to delineate the scope of the invention. Its sole purpose is to present some embodiments of the invention in a simplified form as a prelude to the more detailed description that is presented later.

Certain aspects of the present disclosure include a method for management of type 2 diabetes comprising one or more steps or operations for receiving (e.g., from a practitioner user via a first client device) a plurality of user-generated inputs comprising a plurality of clinical parameters for management of type 2 diabetes in a patient; configuring (e.g., with at least one server communicably engaged with the first client device) a clinical algorithm for initiation and titration of a GLP-1 agonist drug regimen for the patient according to the plurality of user-generated inputs; configuring (e.g., with the at least one server) a conversational AI model according to the clinical algorithm; receiving (e.g., with the at least one server) a first set of blood sugar or hemoglobin A1C data for the patient; outputting (e.g., with a conversational agent) a first generative voice prompt to the patient according to the conversational AI model, wherein the first generative voice prompt comprises a medication initiation prompt for the GLP-1 agonist drug regimen, wherein the conversational agent comprises a smart speaker communicably engaged with the at least one server via a network interface; receiving (e.g., with the conversational agent) a first voice input from the patient in response to the first generative voice prompt, wherein the first voice input comprises a response to the medication initiation prompt; processing (e.g., with the at least one server) the first set of blood sugar or hemoglobin A1C data and the first voice input according to the clinical algorithm; outputting (e.g., with the conversational agent) a second generative voice prompt according to the conversational AI model, wherein the second generative voice prompt comprises a first dosage instruction for the GLP-1 agonist drug regimen for the patient according to the clinical algorithm; and administering (e.g., by the patient) a dose of the GLP-1 agonist drug to the patient in accordance with the first dosage instruction.

In accordance with certain aspects of the present disclosure, the method for management of type 2 diabetes may further comprise one or more steps or operations for establishing a data transfer interface between a continuous glucose monitor device or a glucometer for the patient and the at least one server. In certain embodiments, the first set of blood sugar or hemoglobin A1C data for the patient comprises blood sugar or hemoglobin A1C data collected via the continuous glucose monitor device or glucometer. Certain aspects of the method for management of type 2 diabetes may further comprise one or more steps or operations for outputting (e.g., with the conversational agent) a third generative voice prompt according to the conversational AI model, wherein the third generative voice prompt comprises a medication log prompt for the GLP-1 agonist drug regimen; receiving (e.g., with the conversational agent) a second voice input from the patient in response to the third generative voice prompt, wherein the second voice input comprises medication log data for the patient; and recording (e.g., with the at least one server) the medication log data for the patient according to the second voice input. Certain aspects of the method for management of type 2 diabetes may further comprise one or more steps or operations for receiving (e.g., with the at least one server) a second set of blood sugar or hemoglobin A1C data for the patient; and analyzing (e.g., with the at least one server) the second set of blood sugar or hemoglobin A1C data and the medication log data for the patient according to the clinical algorithm. Certain aspects of the method for management of type 2 diabetes may further comprise one or more steps or operations for outputting (e.g., with the conversational agent) a fourth generative voice prompt according to the conversational AI model, wherein the fourth generative voice prompt comprises a second dosage instruction for the GLP-1 agonist drug regimen for the patient according to the clinical algorithm; and administering, by the patient, a second dose of the GLP-1 agonist drug to the patient in accordance with the second dosage instruction. Certain aspects of the method for management of type 2 diabetes may further comprise one or more steps or operations for outputting (e.g., with the conversational agent) a fifth generative voice prompt according to the conversational AI model, wherein the fifth generative voice prompt comprises a check-in prompt for the patient; receiving (e.g., with the conversational agent) a third voice input from the patient in response to the fifth generative voice prompt, wherein the third voice input comprises a response to the check-in prompt; and recording (e.g., with the at least one server) response data for the patient according to the third voice input.

Further aspects of the present disclosure provide for a method for management of type 2 diabetes comprising one or more steps or operations for receiving (e.g., from a practitioner user via a first client device) a plurality of user-generated inputs comprising a plurality of clinical parameters for management of type 2 diabetes in a patient; configuring (e.g., with at least one server communicably engaged with the first client device) a clinical algorithm for initiation and titration of a biguanide drug regimen for the patient according to the plurality of user-generated inputs; configuring (e.g., with the at least one server) a conversational AI model according to the clinical algorithm; receiving (e.g., with the at least one server) a first set of blood sugar or hemoglobin A1C data for the patient; outputting (e.g., with a conversational agent) a first generative voice prompt to the patient according to the conversational AI model, wherein the first generative voice prompt comprises a medication initiation prompt for the biguanide drug regimen, wherein the conversational agent comprises a smart speaker communicably engaged with the at least one server via a network interface; receiving (e.g., with the conversational agent) a first voice input from the patient in response to the first generative voice prompt, wherein the first voice input comprises a response to the medication initiation prompt; processing (e.g., with the at least one server) the first set of blood sugar or hemoglobin A1C data and the first voice input according to the clinical algorithm; outputting (e.g., with the conversational agent) a second generative voice prompt according to the conversational AI model, wherein the second generative voice prompt comprises a first dosage instruction for the biguanide drug regimen for the patient according to the clinical algorithm; and administering, by the patient, a dose of the biguanide drug to the patient in accordance with the first dosage instruction.

In accordance with certain aspects of the present disclosure, the method for management of type 2 diabetes may further comprise one or more steps or operations for outputting (e.g., with the conversational agent) a third generative voice prompt according to the conversational AI model, wherein the third generative voice prompt comprises a medication log prompt for the biguanide drug regimen; receiving (e.g., with the conversational agent) a second voice input from the patient in response to the third generative voice prompt, wherein the second voice input comprises medication log data for the patient; and recording (e.g., with the at least one server) the medication log data for the patient according to the second voice input. In accordance with certain embodiments, the method may further comprise one or more steps or operations for analyzing (e.g., with the at least one server) the medication log data for the patient according to the clinical algorithm to determine a measure of patient adherence to the biguanide drug regimen. In certain embodiments, the method may further comprise one or more steps or operations for outputting (e.g., with the conversational agent) a fourth generative voice prompt according to the conversational AI model, wherein the fourth generative voice prompt comprises a second medication dosage instruction for the biguanide drug regimen for the patient according to the clinical algorithm; and administering, by the patient, a second dose of the biguanide drug to the patient in accordance with the second medication dosage instruction. In accordance with certain aspects of the method, the second dose of the biguanide drug is different from the first dose of the biguanide drug according to the biguanide drug regimen. In certain embodiments, the method may further comprise one or more steps or operations for receiving (e.g., with the at least one server) a first set of electronic medical record data for the patient, wherein the first set of electronic medical record data comprises laboratory test data. The method may further comprise one or more steps or operations for updating (e.g., with the at least one server) the clinical algorithm for initiation and titration of the biguanide drug regimen for the patient according to the first set of electronic medical record data for the patient.

Still further aspects of the present disclosure provide for a method for management of type 2 diabetes comprising one or more steps or operations for receiving (e.g., from a practitioner user via a first client device) a plurality of user-generated inputs comprising a plurality of clinical parameters for management of type 2 diabetes in a patient; configuring (e.g., with at least one server communicably engaged with the first client device) a clinical algorithm for initiation and titration of a SGLT-2 inhibitor drug regimen for the patient according to the plurality of user-generated inputs; configuring (e.g., with the at least one server) a conversational AI model according to the clinical algorithm; receiving (e.g., with the at least one server) a first set of blood sugar or hemoglobin A1C data for the patient; outputting (e.g., with a conversational agent) a first generative voice prompt to the patient according to the conversational AI model, wherein the first generative voice prompt comprises a medication initiation prompt for the SGLT-2 inhibitor drug regimen, wherein the conversational agent comprises a smart speaker communicably engaged with the at least one server via a network interface; receiving (e.g., with the conversational agent) a first voice input from the patient in response to the first generative voice prompt, wherein the first voice input comprises a response to the medication initiation prompt; processing (e.g., with the at least one server) the first set of blood sugar or hemoglobin A1C data and the first voice input according to the clinical algorithm; outputting (e.g., with the conversational agent) a second generative voice prompt according to the conversational AI model, wherein the second generative voice prompt comprises a first dosage instruction for the SGLT-2 inhibitor drug regimen for the patient according to the clinical algorithm; and administering, by the patient, a dose of the SGLT-2 inhibitor drug to the patient in accordance with the first dosage instruction.

In accordance with certain aspects of the present disclosure, the method for management of type 2 diabetes may further comprise one or more steps or operations for outputting (e.g., with the conversational agent) a third generative voice prompt according to the conversational AI model, wherein the third generative voice prompt comprises a medication log prompt for the SGLT-2 inhibitor drug regimen; receiving (e.g., with the conversational agent) a second voice input from the patient in response to the third generative voice prompt, wherein the second voice input comprises medication log data for the patient; and recording (e.g., with the at least one server) the medication log data for the patient according to the second voice input. In certain embodiments, the method for management of type 2 diabetes may further comprise one or more steps or operations for receiving (e.g., with the at least one server) a second set of blood sugar or hemoglobin A1C data for the patient; and analyzing (e.g., with the at least one server) the second set of blood sugar or hemoglobin A1C data and the medication log data for the patient according to the clinical algorithm. In certain embodiments, the method for management of type 2 diabetes may further comprise one or more steps or operations for outputting, with the conversational agent, a fourth generative voice prompt according to the conversational AI model, wherein the fourth generative voice prompt comprises a second dosage instruction for the SGLT-2 inhibitor drug regimen for the patient according to the clinical algorithm; and administering, by the patient, a second dose of the SGLT-2 inhibitor drug to the patient in accordance with the second dosage instruction. In certain embodiments, the second dose of the SGLT-2 inhibitor drug is different from the first dose of the SGLT-2 inhibitor drug according to the SGLT-2 inhibitor drug regimen. In certain embodiments, the method for management of type 2 diabetes may further comprise one or more steps or operations for analyzing (e.g., with the at least one server) the medication log data for the patient according to the clinical algorithm to determine a measure of patient adherence to the SGLT-2 inhibitor drug regimen.

The foregoing has outlined rather broadly the more pertinent and important features of the present invention so that the detailed description of the invention that follows may be better understood and so that the present contribution to the art can be more fully appreciated. Additional features of the invention will be described hereinafter which form the subject of the claims of the invention. It should be appreciated by those skilled in the art that the conception and the disclosed specific methods and structures may be readily utilized as a basis for modifying or designing other structures for carrying out the same purposes of the present invention. It should be realized by those skilled in the art that such equivalent structures do not depart from the spirit and scope of the invention as set forth in the appended claims.

BRIEF DESCRIPTION OF DRAWINGS

The skilled artisan will understand that the figures, described herein, are for illustration purposes only. It is to be understood that in some instances various aspects of the described implementations may be shown exaggerated or enlarged to facilitate an understanding of the described implementations. In the drawings, like reference characters generally refer to like features, functionally similar and/or structurally similar elements throughout the various drawings. The drawings are not necessarily to scale, emphasis instead being placed upon illustrating the principles of the teachings. The drawings are not intended to limit the scope of the present teachings in any way. The system and method of the present disclosure may be better understood from the following illustrative description with reference to the following drawings in which.

DETAILED DESCRIPTION

Figure 1:
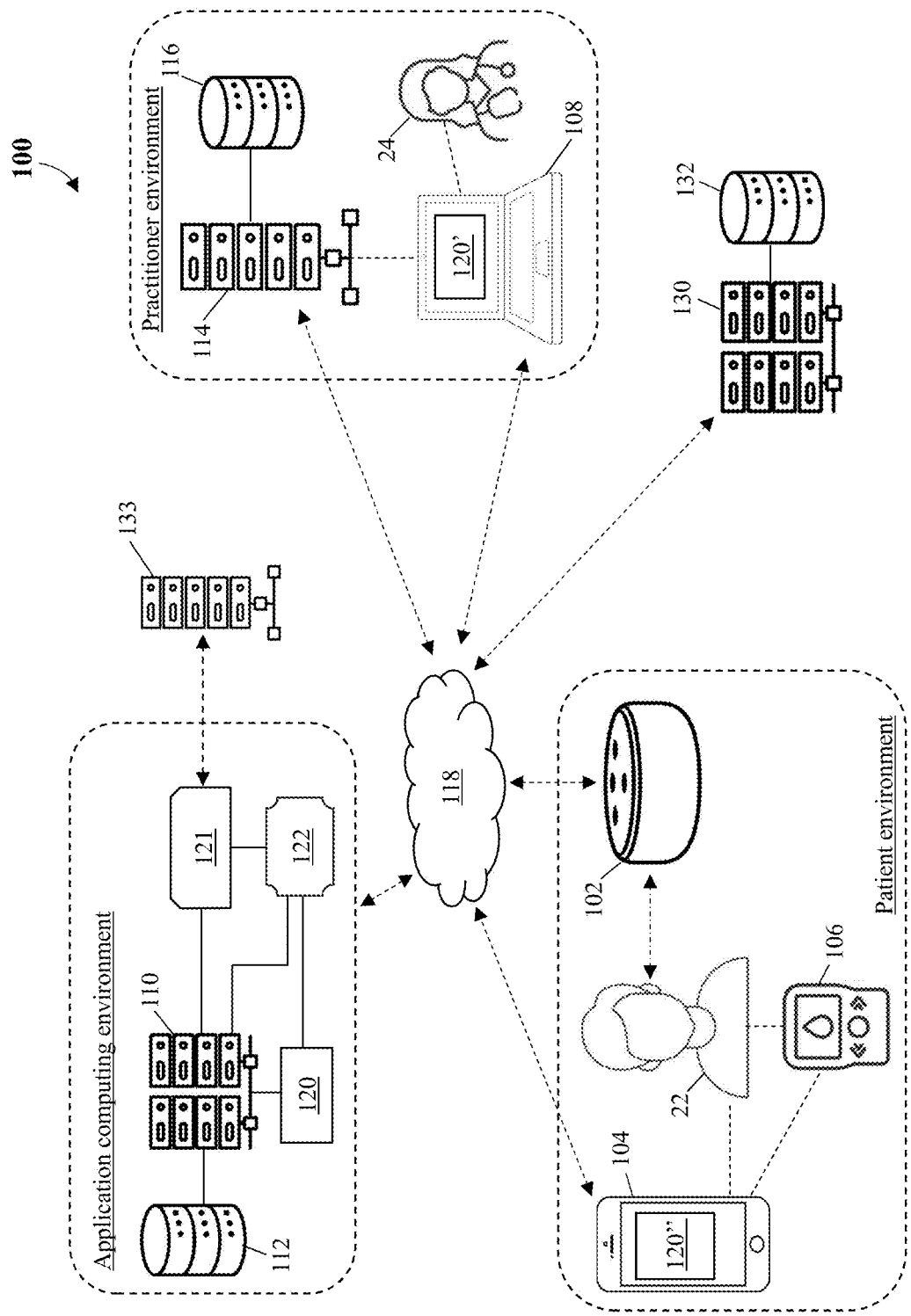
FIG. 1 is an architecture diagram of a voice-based system for management of type 2 diabetes through which one or more aspects of the present disclosure may be implemented.

It should be appreciated that all combinations of the concepts discussed in greater detail below (provided such concepts are not mutually inconsistent) are contemplated as being part of the inventive subject matter disclosed herein. It also should be appreciated that terminology explicitly employed herein that also may appear in any disclosure incorporated by reference should be accorded a meaning most consistent with the particular concepts disclosed herein.

Following below are more detailed descriptions of various concepts related to, and embodiments of, inventive methods, apparatus and systems configured to provide for automated initiation, titration and management of a medication regimen in a patient with type 2 diabetes via a series of voice-based and/or chat-based interactions between the patient and an artificial intelligence (AI) conversational agent.

It should be appreciated that various concepts introduced above and discussed in greater detail below may be implemented in any of numerous ways, as the disclosed concepts are not limited to any particular manner of implementation. Examples of specific implementations and applications are provided primarily for illustrative purposes. The present disclosure should in no way be limited to the exemplary implementation and techniques illustrated in the drawings and described below.

Before the present invention and specific exemplary embodiments of the invention are described, it is to be understood that this invention is not limited to the particular embodiments described, and as such may vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed by the invention. The upper and lower limits of these smaller ranges may independently be included in the smaller ranges, and are also encompassed by the invention, subject to any specifically excluded limit in a stated range. Where a stated range includes one or both of the endpoint limits, ranges excluding either or both of those included endpoints are also included in the scope of the invention.

As used herein, the term "behaviorome" means the set of all behaviors of an individual or a group of individuals that may be observed and analyzed to create a plurality of digital behavior markers for the individual or group of individuals.

As used herein, the terms "computer," "processor" and "computer processor" encompass a personal computer, a workstation computer, a tablet computer, a smart phone, a microcontroller, a microprocessor, a field programmable object array (FPOA), a digital signal processor (DSP), an application-specific integrated circuit (ASIC), a field programmable gate array (FPGA), a programmable logic array (PLA), or any other digital processing engine, device or equivalent capable of executing software code including related memory devices, transmission devices, pointing devices, input/output devices, displays and equivalents.

As used herein, the terms "conversational agent" or "conversational AI agent" or "agent" refer to any device, system and/or program configured to autonomously execute one or more objective function in response to one or more inputs. Said terms may be used interchangeably. The one or more inputs may comprise one or more user-generated inputs, sensor-based inputs, internal system inputs, external system inputs, environmental percepts, and the like. Examples of conversational agents may include, but are not limited to, one or more virtual assistant, personal assistant or chatbot.

As used herein, the terms "drug regimen" or "medication regimen" mean a prescribed systematic form of treatment for a course of drug(s).

As used herein, the term "dosing regimen" means a frequency of administration, the dose per a single administration, the time interval between administrations, duration of treatments, and how a drug is to be taken. In accordance with certain aspects of the present disclosure, the term "dosing regimen" may comprise one or more aspects of a drug regimen. In certain contexts, the terms "dosing regimen" and "drug regimen" may be used interchangeably.

As used herein, the term "exemplary" means serving as an example or illustration and does not necessarily denote ideal or best.

As used herein, the term "includes" means includes but is not limited to, the term "including" means including but not limited to. The term "based on" means based at least in part on.

As used herein, the term "interface" refers to any shared boundary across which two or more separate components of a computer system may exchange information. The exchange can be between software, computer hardware, peripheral devices, humans, and combinations thereof.

As used herein, the term "mobile device" includes any portable electronic device capable of executing one or more digital functions or operations; including, but not limited to, smart phones, tablet computers, personal digital assistants, wearable activity trackers, smart watches, smart speakers, and the like.

As used herein, the terms "provider" and "practitioner" refer to a healthcare professional or healthcare provider that is responsible for one or more aspects of a patient's care; including, but not limited to, a doctor, a nurse, a physician's assistant, a pharmacist, a technician, and the like. The terms "provider" and "practitioner" may be used interchangeably throughout the present disclosure. As used herein, the term "practitioner user" refers to a provider/practitioner who is also a user of the voice-based system for management of type 2 diabetes, as described herein.

As used herein, the term "patient" refers to any recipient of health care services that are performed or facilitated by a practitioner; including, but not limited to, an individual with type 2 diabetes. As used herein, the term "patient user" refers to a patient who is also a user of the voice-based system for management of type 2 diabetes, as described herein.

As used herein, a "portal" makes network resources (applications, databases, etc.) available to end users. The user can access the portal via a web browser, smart phone, tablet computer, and other client computing devices. Portals may include network enabling services such as e-mail, chat rooms and calendars that interact seamlessly with other applications.

As used herein, "remote patient intervention" refers to a model of care that incorporates the use of remote patient monitoring data to provide real-time disease and medication management for patients based on physician-approved protocols. Autonomous diabetes medication dosing instructions of the present disclosure is an example of remote patient intervention.

As used herein, the term "smart speaker" refers to an internet-enabled speaker that is controlled by spoken commands and is capable of streaming audio content, relaying information, and communicating with other devices. In accordance with certain aspects of the present disclosure, a smart speaker may be configured to execute a client-side instance of a conversational AI agent.

As used herein, the term "transmit" and its conjugates means transmission of digital and/or analog signal information by electronic transmission, Wi-Fi, BLUETOOTH technology, wireless, wired, or other known transmission technologies including transmission to an Internet web site.

As used herein, a "GLP-1 agonist drug" comprises a class of prescription medications that helps lower blood sugar levels for people with type 2 diabetes, including semaglutide, tirzepatide, liraglutide, retatrutide, dulaglutide, exenatide, and lixisenatide.

As used herein, a "biguanide drug" comprises a class of prescription medications that helps lower blood sugar levels for people with type 2 diabetes, including metformin IR (immediate release) and metformin ER (extended release).

As used herein, a "SGLT-2 inhibitor drug" comprises a class of prescription medications that helps lower blood sugar levels for people with type 2 diabetes, including empagiflozen, canagiflozen, dapagiflozen, bexagliflozin, and sotagliflozin.

Certain aspects of the present disclosure provide for a remote patient intervention system comprising a portable integrated electronic device and computer-readable media configured to operably engage with at least one remote virtual server, preferably a secured HIPAA-compliant server, to provide one or more cloud-based control services; including, but not limited to, automated speech recognition (ASR), natural language processing (NLP), natural language understanding (NLU), dialogue management, and text-to-speech (TTS) conversion, among others. In various embodiments, the cloud-based control services together may comprise a conversational artificial intelligence (AI) agent configured to perform natural language or speech-based automated dynamic multi-turn conversations with a user of the portable integrated electronic device. The portable integrated electronic device enables the user to access, interact, and engage with said conversational AI agent to remotely receive at least one medication prescription, therapeutic dose titration, and dose regimen, among others. In various embodiments, said portable integrated electronic device may provide recording and/or monitoring of the user's medication adherence, medication adverse reactions, and one or more behavioral phenotype for the user (e.g., including social demographics, health literacy, technical literacy, illness perception, and clinical complexity, among others). In various embodiments, said portable integrated electronic device may provide recording and/or monitoring of custom user interactions, including but not limited to device check-in frequency, user speech complexity, clinical flexibility, user personality, and user persistence, among others. In various embodiments, said portable integrated electronic device listens (e.g., via at least one microphone) and interacts with the user (e.g., via at least one speaker) to determine at least one intent based on NLU of the user's speech. Said portable integrated electronic device may be configured to record and/or monitor one or more user voice utterances and transmit voice data to at least one cloud-based control service virtual server via a telecommunication network. The cloud-based control service may perform ASR, NLP and/or NLU on the utterances to determine intents expressed by the utterances via one or more scripted computing skills. In response to an identified intent, the control service may perform one or more corresponding actions. In various embodiments, an action may be performed at the control service and/or by commanding said portable integrated electronic device to perform a function. The combination of the portable integrated electronic device and one or more applications executed by the control service may comprise a conversational AI agent. The conversational AI agent may provide conversational interactions, utilizing ASR, NLP, NLU, or TTS conversion, and the like, to perform said functions, interact with the user (i.e., patient), query questions to the user, and provide said user with non-clinical self-management instructions, questionnaire, education, health-related information, nutrition, carb counts, instructional video, tasks, alerts, and the like. The portable integrated electronic device may be optimally configured for low device operation latency and for parsimonious memory usage, promptly responsive for enhancing user experience.

Certain aspects of the present disclosure provide for a portable integrated electronic voice-based device comprising or more microprocessor, microcontroller, read-only memory device, memory storage device, flash memory, I-O device, buttons, volume control button, display, user interface, rechargeable battery, microUSB, USB-C, CODEC, microphone, speaker, speaker amplifier, wireless transceiver IC, including but not limited to Bluetooth, Wi-Fi or cellular, micro GSM/GPRS chipset, micro SIM module, antenna, haptic sensor, power management IC, vibrating motor (output), preferably configured in combination, to function fully as an Internet-of-Things (IoT) device. The portable integrated electronic device is communicably engaged (e.g., via a communications network) with one or more remote cloud-based or virtual servers capable of providing ASR-response, NLP/NLU-processing, predictive algorithm processing, reminders, alerts, general and specific information for the remote management of patients with an acute, chronic, condition, or disease, including but not limited to diabetes, cancer, hypertension, kidney disease, infectious disease and heart failure, among others. In various embodiments, the portable integrated electronic device may be communicably engaged with one or more external devices, including but not limited to, a point-of-care testing (POCT) device, a glucose meter, a wearable continuous glucose meter, an HbA1C meter, a lactate meter, an IoT sensor, a remote or mobile patient monitor for EKG, ECG, variable heart rate, blood pressure, a capillary blood collection device, or the like, a mobile phone, and a smart appliance, among others.

Certain aspects of the present disclosure provide for a behaviorome platform comprising a patient engagement engine comprising the portable integrated electronic device. In various embodiments, the patient engagement engine enables the execution of at least one proprietary derived clinical protocol for instructing a patient user via at least one conversational AI agent. In various embodiments, said device, operating alone or engaged in combination with said cloud-based control service server, uses one or more proprietary derived voice dataset to deliver personalized interactions with a user of the device (e.g., a patient). In various embodiments, one or more said behavioral phenotype or custom interactions are collected, processed, and analyzed by the patient engagement engine to provide the user with autonomous medication management (including, for example, initiation and titration of one or more diabetes drug), personalized intervention, and/or to monitor medication adherence and persistence using one or more clinically validated survey or questionnaire (e.g., via a generative chat interface or voice-based multi-turn interaction). In various embodiments, one or more said behavioral phenotype or said custom interactions are collected, processed, and analyzed by the patient engagement engine to provide (in real-time, synchronously, or asynchronously) the user with non-clinical self-management instructions or education for therapeutic titration, medication dose adjustment, medication dosing regimen, perform a blood measurement with a home-use meter, glucose meter (i.e., glucometer), or POCT device, recommend nutrition or physical exercise, care plan, and a personalized intervention, among others. In various embodiments, said device may provide said information to a user on a mobile phone application.

Certain aspects of the present disclosure provide for a physician portal for the remote patient intervention system comprising said portable integrated electronic device, a secured HIPAA-compliant remote application World Wide Web ("Web") server, an EMR database, cloud-based control service server, client computing devices, dashboard, and non-transitory computer-readable media. The remote application Web server may be accessible through one or more client computing devices, including but not limited to, desktop, laptop, tablet, mobile phone, smart phone, and smart appliances, among others. The remote Web server may contain IT support applications software that may include a database for storing patient and/or user(s) information. The applications software may provide an interactive physician portal or WWW portal between healthcare providers, nurses, clinical staff, insurer, and patients for communication and sending prescription information, among other functions. In various embodiments, the remote Web server may communicate or engage operably with an electronic health record (EHR) or an electronic medical record (EMR) system. The remote Web server may communicate with said EHR or EMR system using an application programming interface (API). In various embodiments, said dashboard may be configured to enable a healthcare provider to access the physician portal. In various embodiments, one or more client device may be communicably engaged with the application server, the client device being configured to display a graphical user interface (GUI) or a mobile application containing non-limiting information including patient engagement, patient behaviorome, remote patient intervention, non-clinical self-management, patient and healthcare provider interactions, user log, medication log, blood sugar log, therapeutic titration, medication dose adjustment or changes, medication dosing regimen, date, time, hourly or daily blood glucose values, HbA1C values, health record, analytical test results, user self-management performance trends, medication adherence, persistence, nutrition habits, physical habits, behaviors, care plan, protocol, patient weight, frequency, goal fasting blood sugar range, among others. In various embodiments, the GUI or mobile application may contain text, graphics, video, or charts, among others. In various embodiments, the dashboard and GUI may be accessible over the Internet. In various embodiments, the physician portal may be incorporated into a product comprising a hardware implementation or software instructions stored and executable from one or more non-transitory storage medium located locally on a client device or mobile computing platform (e.g., smart phone) or remotely on a cloud server or cloud service.

Certain aspects of the present disclosure provide for a remote patient intervention system comprising: a portable voice-based electronic device configured to execute an instance of a GUI comprising a plurality of user prompts associated with diabetes or a disease or disorder of a patient user; an integral or remote processor communicatively engaged with said electronic device; and a non-transitory computer readable medium having instructions stored thereon that, when executed, cause the processors to perform one or more operations, the one or more operations comprising operations for: receiving a plurality of user-generated voice or touch screen inputs in response to the plurality of user prompts; receiving one or more sensor inputs; receiving one or more external data inputs comprising at least one patient voice dataset; aggregating the plurality of user-generated inputs, the one or more sensor inputs, and the one or more external data inputs to define an aggregated dataset; analyzing the aggregated dataset according to at least one conversational AI framework comprising at least one rules-based or large language AI model, wherein the at least one conversational AI framework comprises at least one dependent variable corresponding to a current or future state of a patient behaviorome or a patient engagement engine; generating at least one conversational AI prompt according to the at least one conversational AI framework; and generating, with the processor, at least one activity recommendation in response to at least one diagnostic measure, the at least one activity recommendation corresponding to at least one patient action associated with the current or future state of glycemic control. In various embodiments, the system further comprises at least one said portable voice-based electronic device communicatively engaged with at least point of care testing (POCT) device, including but not limited to a portable or wearable continuous glucose monitoring system (CGM), among others.

Certain aspects of the present disclosure provide for computer-implemented methods for performing a remote patient intervention. In various embodiments, a conversational AI encounter with a user of a portable voice-based electronic device may be triggered by voice, proximity, or touch. The user may be instructed to complete the setup of said device and account linkage. The user may be asked to set up a wireless link (e.g., via BLUETOOTH) to a monitoring device, such as a continuous glucose monitor (CGM). The user may be instructed to conduct one or more non-limiting maintenance tasks such as making sure the CGM is worn correctly, making sure data is transmissible, and sensor replacement reminder or refill. The user may be asked to confirm understanding of any provider-driven changes such as a medication dose change, the addition of an alternate medication, any necessary medication change instructions, any necessary calibration of medication (e.g., with one or more meals), and any addition of non-glycemic medications (e.g., blood pressure medication, cholesterol medication, etc.) that may affect a clinical protocol. In various embodiments, the device may then collect data for any non-limiting driven changes such as diabetes medication adherence, blood sugar results, specific information on meals that may cause changes in CGM blood sugar levels, and side effects. The conversational AI agent then may ask the user to confirm the understanding of any changes, information about meals, side effects, exercise and other behaviorome tasks, among others.

Certain aspects of the present disclosure provide for computer-implemented methods for performing a remote patient intervention comprising one or more oral medication titration protocols. In various embodiments, oral medication titration protocols may comprise non-limiting oral medications used for the treatment of diabetes such as non-insulin glycemic medications, statins, angiotensin receptor blockers, among others. In various embodiments, glycemic control oral medication protocols may comprise one or more non-limiting principles such as starting prescriptions, identifying contraindicated medications, setting doses manually, selection of titration priorities, checking all device user's medication side effects, device usage risk assessment and lock-out if a device user is admitted to a hospital, titration duration, titration procedure to prevent side effect confounders, and initiation of glycemic medications based on HbA1C percentages, among others.

Certain aspects of the present disclosure provide for computer-implemented methods for performing a remote patient intervention comprising one or more diabetes medication titration protocols. In various embodiments, diabetes medication titration protocols may comprise glycemic goals, GLP-1 agonist drug protocol, biguanide drug protocol, SGLT-2 inhibitor drug protocol, medication interactions, clinical status change, titration considerations, medication intensification, medication de-intensification, patient hypoglycemia intervention, goal fasting blood glucose range, starting medication dose, maximum permitted medication dose, dose frequency, titration schedule, minimum titration requirements, hyperglycemia and hypoglycemia protocols, among others.

Certain aspects of the present disclosure provide for one or more non-transitory computer-readable medium encoded with instructions for commanding one or more processors of said portable device, client computing device, or cloud-based control service remote server to execute one or more steps of one or more methods or processes within a remote patient intervention system, behaviorome platform, or patient engagement engine comprising one or more operations for: receiving a plurality of data from one or more data sources, the plurality of data comprising one or more voice-based patient user generated input or response, conversational AI queries or responses, cloud-based computing server input or output, client computing device input or output; aggregating the plurality of data to define an aggregated voice dataset; analyzing the aggregated voice dataset according to at least one AI framework comprising at least one rules-based or large language model generative AI framework, wherein the at least one said AI framework comprises at least one dependent variable corresponding to a current or future state of serum electrolyte values, creatinine, blood urea nitrogen (BUN), medication adherence, side effects, blood glucose, blood lipids, or HbA1C of a patient; using at least one clinical protocol and generating at least one autonomous adjustment medication dose recommendation for a diabetic patient user, preferably type 2, to achieve better glycemic and diabetes disease management control and health self-management, in a non-clinical setting. An object of the present disclosure provides for a remote patient intervention system for patient self-management of a medication regimen for management of type 2 diabetes in a non-clinical setting.

Further objects and advantages of the present disclosure include computer-implemented methods for performing voice-based, conversational AI titration protocols for a diabetes medication dosing regimen. Diabetes medication titration protocols may comprise glycemic goals, GLP-1 agonist drug protocol, biguanide drug protocol, SGLT-2 inhibitor drug protocol, basal protocol, types of medication to administer, titration considerations, medication intensification, medication de-intensification, patient hypoglycemia intervention, prandial protocol, goal fasting blood glucose range, starting medication dose, maximum permitted medication dose, dose frequency, titration schedule, minimum titration requirements, adverse event protocols, patient safety protocols, hyperglycemia and hypoglycemia protocols, among others. In accordance with certain embodiments, a medication titration protocol may comprise one or more default and editable prescription parameters within a graphical user interface of a practitioner (e.g., primary care provider) application.

Further objects and advantages of the present disclosure include computer-implemented methods for performing a remote patient intervention comprising one or more oral medication titration protocols. In various embodiments, oral medication titration protocols may comprise one or more non-limiting oral medications used for the treatment of diabetes such as non-insulin glycemic medications, statins, angiotensin receptor blockers, glucagon-like peptide 1 agonists, sodium-glucose cotransporter 2 inhibitors, glucose-dependent insulinotropic polypeptide combination medications, biguanides, among others. In various embodiments, glycemic control oral medication protocols may comprise one or more non-limiting principles such as starting prescriptions, identifying contraindicated medications, setting doses manually, selection of titration priorities, checking medication side effects for all patient medications and medication combinations, device usage risk assessment and lock-out parameters (e.g., lock-out if a qualifying adverse event takes place, lock-out if a qualifying laboratory result takes place, lock-out in response to a practitioner input, etc.) titration duration, titration procedure to prevent side effect confounders, initiation of medication based on HbA1c percentages, among others. In accordance with certain aspects of the present disclosure, a "lock-out" comprises one or more operations under the one or more diabetes medication titration protocols may be temporarily or permanently discontinued.

Further objects and advantages of the present disclosure provide for one or more non-transitory computer-readable medium encoded with instructions for commanding one or more processors of a smart speaker device, a client computing device, and/or cloud-based control service remote server to execute one or more steps of one or more methods or processes within a remote patient intervention system, behaviorome platform, and/or patient engagement engine comprising one or more operations for: receiving a plurality of data from one or more data sources, the plurality of data comprising one or more voice-based patient user generated input or response, conversational AI queries or responses, cloud-based computing server input or output, client computing device input or output; aggregating the plurality of data to define an aggregated voice dataset; analyzing the aggregated voice dataset according to at least one AI framework comprising at least one rules-based or large language model generative AI framework, wherein the at least one said AI framework comprises at least one dependent variable corresponding to a current or future state of serum electrolyte values, creatinine, blood urea nitrogen (BUN), medication adherence, side effects, blood glucose, blood lipids, or hemoglobin A1C of a patient; and generating at least one autonomous adjustment medication dose recommendation according to at least one clinical protocol for a patient with type 2 diabetes to achieve better glycemic and diabetes disease control and health self-management, in a non-clinical setting (e.g., at home).

Turning now descriptively to the drawings, in which similar reference characters denote similar elements throughout the several views, FIG. 1 depicts an architecture diagram of a system 100 for remote management of type 2 diabetes in and through which certain aspects of the present invention may be implemented. In accordance with certain aspects of the present disclosure, system 100 is configured to enable a voice-based remote patient intervention system for initiation and titration of a medication regimen in a patient user 22 with type 2 diabetes. System 100 comprises a practitioner computing environment, a patient computing environment and an application computing environment configured to enable configuration of a clinical protocol for management of type 2 diabetes by a practitioner user 24; configuration of a clinical algorithm for initiation and titration of a diabetes medication regimen; and configuration of a conversational AI model to enable a plurality of generative, voice-based interactions between a conversational agent 122 and patient user 22. Practitioner user 24 may be a primary care provider for patient user 22. In accordance with certain embodiments, a patient environment of system 100 may comprise a smart speaker 102, an end user device 104 and, optionally, a continuous glucose monitor 106. End user device 104 may comprise a smart phone, tablet computer, desktop computer, personal digital assistant, or other personal computing device. Continuous glucose monitor 106 may be a body-worn device comprising a sensor, a transmitter and a user interface configured to be worn by patient user 22 to monitor blood glucose on a continual basis. Continuous glucose monitor 106 may be communicably engaged with end user device 104 via a wireless data transfer interface (e.g., BLUETOOTH) to transmit blood glucose data for patient user 22 to a software application executing on end user device 104. Examples of continuous glucose monitor 106 may include the FREESTYLE LIBRE, manufactured by ABBOTT LABORATORIES, and the DEXCOM G7, manufactured by DEXCOM INC.

In accordance with certain embodiments, a practitioner environment of system 100 may include a practitioner computing device 108, a healthcare provider server 114 and a healthcare provider database 116. Practitioner computing device 108 may be communicably engaged with healthcare provider server 114 via a local area or a wide area network interface. Healthcare provider database 116 may be communicably engaged with healthcare provider server 114 to store and retrieve a plurality of health records; e.g., health records associated with management of type 2 diabetes for patient user 22. Practitioner computing device 108, healthcare provider server 114 and healthcare provider database 116 may be operably engaged according to a HIPAA-compliant network architecture. In certain embodiments, system 100 may comprise one or more external electronic medical record (EMR)/electronic health record (EHR) server 130 and external EMR/EHR database 132. External EMR/EHR server 130 and external EMR/EHR database 132 may comprise one or more third-party medical server, including one or more laboratory information management system (LIMS) server, third-party payor server, government server, and the like.

In accordance with certain aspects of the present disclosure, the elements of the patient environment, the practitioner environment, and, optionally, the external EMR/EHR server 130 and external EMR/EHR database 132, may be communicably engaged with the application computing environment via communications network 118. The application computing environment may comprise a cloud computing environment. Communications network 118 may comprise one or more network interfaces to enable one or more real-time data transfer interfaces between the elements of system 100; including, for example, one or more application programming interface (API) or software development kit (SDK). In accordance with certain aspects of the present disclosure, the application computing environment comprises at least one application server 110 and an application database 112. In accordance with certain embodiments, application database 112 may comprise a knowledge base comprising a plurality of subject-matter information from which the conversational AI model may draw to generate responses to one or more user queries. Application server 110 may comprise one or more computing modules and control services to enable one or more functions and operations of system 100. In accordance with certain aspects of the present disclosure, application server 110 comprises a diabetes management application 120, a large language model engine 121, and a conversational agent 122 service. Large language model engine 121 may comprise a large language model configured to drive a plurality of generative text-to-speech outputs of conversational agent 122. In accordance with certain aspects of the present disclosure, system 100 may comprise an external server 133 comprising a third-party large language model service. Large language model engine 121 may be communicably engaged with external server 133 via at least one data transfer interface to execute one or more functions or operations for configuring, implementing and/or executing the conversational AI model.

In accordance with certain aspects of the present disclosure, patient user 22 provides a voice input to smart speaker 102 to invoke one or more functions of conversational agent 122. The voice input is converted by smart speaker 102 into a digital audio format and is streamed to application server 110 (as described in more detail herein) and is received at conversational agent 122 (e.g., in real-time). In various embodiments, one or more invocations from smart speaker 102 and generative voice outputs (e.g., diabetes medication initiation and titration instructions) may be communicated bi-directionally between smart speaker 102 and conversational agent 122.

In accordance with certain aspects of the present disclosure, an exemplary use case of system 100 is initiated within the practitioner environment. In accordance with certain embodiments, practitioner user 24 may instantiate a practitioner instance 120' of diabetes management application 120 at a user interface of practitioner computing device 108. Practitioner instance 120' may comprise a graphical user interface configured to enable practitioner user 24 to input a plurality of clinical parameters for management of type 2 diabetes for patient user 22; e.g., in accordance with one or more clinical protocols (as described in more detail herein below). In certain embodiments, practitioner instance 120' may comprise a plurality of pre-populated data for patient user 22 comprising a plurality of health record data to assist practitioner user 24 in configuring the clinical parameters. Practitioner instance 120' may be configured to communicate the user-generated data (e.g., via a hypertext transfer protocol) to application server 110 via communications network 118. Application server 110 may receive and process the user-generated data according to one or more data processing operations for diabetes management application 120. In accordance with certain embodiments, diabetes management application 120 is configured to process the user-generated data to configure a clinical algorithm for initiation and titration of a medication regimen for the patient. Diabetes management application 120 may provide one or more outputs to conversational agent 122 comprising parameters for the clinical algorithm. Large language model engine 121 may execute one or more operations with internal or external large language models under the direction of conversational agent 122. In accordance with certain aspects of the present disclosure, the conversational agent 122 may comprise an AI framework comprising a neural network architecture configured to enable one or more automated speech recognition (ASR), natural language processing (NLP), natural language understanding (NLU), dialogue management, text-to-speech (TTS) converter function.

In accordance with certain aspects of the present disclosure, application server 110 may receive one or more clinical data inputs for patient 22 via one or more of end user device 104, continuous glucose monitor 106, external EMR/EHR server 130 and/or healthcare provider server 114. Clinical data inputs may include, but are not limited to, basic metabolic panel (e.g., sodium, potassium, chloride, bicarbonate, BUN, creatinine, glucose, magnesium, phosphate, calcium, uric acid, and the like), hemoglobin A1C, medication adherence based on patient-reported data (e.g., prescription ("Rx") fill data, log data, and other data sources), blood pressure data and other physiological sensor data, patient-reported side effects, and the like. In certain embodiments, patient-reported data may be received via a graphical user interface of a patient instance 120" of diabetes management application 120. Diabetes management application 120 may receive and process the clinical data inputs according to the clinical algorithm and provide one or more outputs to large language model engine 121 in accordance with the same. Conversational agent 122 may generate a first generative voice prompt and output the generative voice prompt to patient user 22 via smart speaker 102. In accordance with certain aspects of the present disclosure, the first generative voice prompt comprises a medication initiation prompt for patient user 22 to begin a diabetes medication regimen according to the clinical protocol.

In accordance with certain aspects of the present disclosure, patient user 22 may provide a voice input at smart speaker 102 in response to the medication initiation prompt (e.g., to confirm initiation of the diabetes medication regimen according to the clinical protocol). Diabetes management application 120 may process the voice input and, optionally, the clinical data (e.g., at one or more time points) according to the clinical algorithm and provide one or more outputs to conversational agent 122 with the same. In accordance with certain aspects of the present disclosure, conversational agent 122 may generate a second or subsequent generative voice prompt with the help of large language model engine 121 and output the second or subsequent generative voice prompt to patient user 22 via smart speaker 102. In accordance with certain aspects of the present disclosure, the second or subsequent generative voice prompt comprises a diabetes medication dosage instruction for the patient according to the clinical algorithm. In certain instances, the medication dosage instruction may comprise a titration instruction for at least one medication. In certain instances, the medication dosage instruction may comprise a medication dosage instruction for two or more medications.

Figure 2:
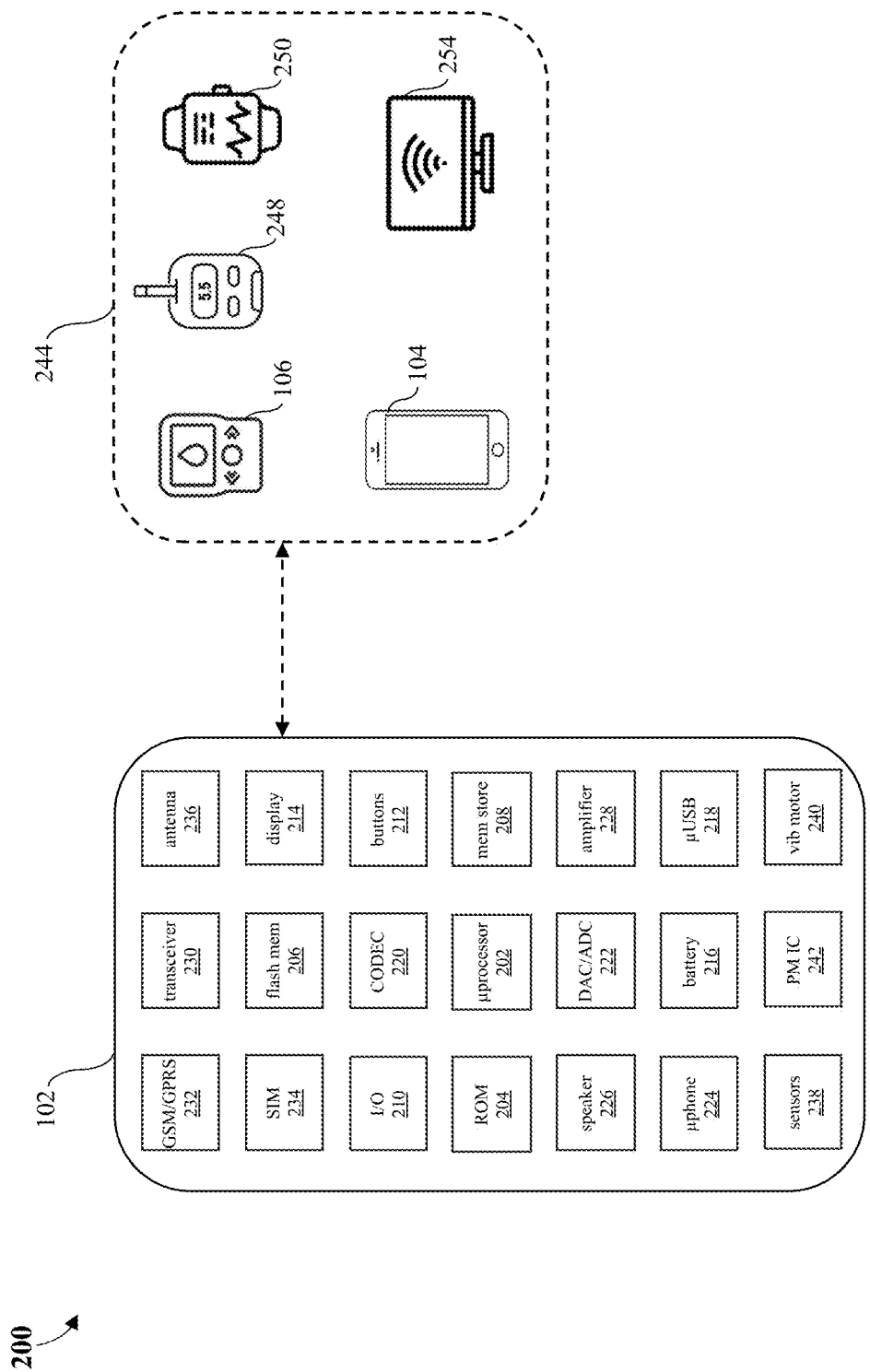
FIG. 2 is a schematic diagram of a smart speaker and a plurality of remote patient monitoring devices through which one or more aspects of the present disclosure may be implemented.

Referring now to FIG. 2, a schematic diagram 200 of smart speaker 102 and a plurality of remote patient monitoring devices 244, through which one or more aspects of the present disclosure may be implemented, is shown. In accordance with certain aspects of the present disclosure, smart speaker 102 may comprise one or more microprocessor 202 or microcontroller, read-only memory device 204, flash memory 206, memory storage device 208, I-O device 210, buttons 212 (e.g., volume control button), display 214 (e.g., user interface) rechargeable battery 216, microUSB 218, CODEC 220, digital-to-analog converter (DAC)/analog-to-digital converter (ADC) 222, microphone 224, speaker 226, speaker amplifier 228, wireless transceiver ICs 230 (e.g., including, but not limited to, BLUETOOTH and Wi-Fi), micro GSM/GPRS chipset 232, micro SIM module 234, antenna 236, sensors 238, vibrating motor (output) 240, and power management IC 242. In accordance with certain embodiments, elements 202-240 may be operably configured in combination, each component engaged electronically, via one or more I²C or I²S and controlled by microprocessor 202 to function as a self-contained portable Internet-of-Things (IoT) device. In certain embodiments, microprocessor 202 may comprise a SoC MT8163 SoC or MT7658CSN ICs (MEDIATEK, Hsinchu, Taiwan) incorporating wireless transceiver ICs 230 and a GPS receiver. In various embodiments, flash memory 206 may comprise an embedded Multi-Chip (eMCP) with RAM and eMMC-flash memory integrated in a single IC (e.g., available from several vendors including, MICRON (Boise, ID), SAMSUNG (Suwon-si, South Korea), and SK HYNIX (Icheon-si, South Korea). In various embodiments, DAC/ADC 222 may comprise one or more converters; for example, TEXAS INSTRUMENTS (Dallas, TX) TLV320ADC, TLV320ADC3101, TLV320DAC. In various embodiments, speaker amplifier 228 may be embedded with DAC/ADC 222 whereby the output of the chip feeds into speaker 226. In various embodiments, CODEC 220 may comprise an ultra-low power audio CODEC (e.g., TLV320DAC3202, TEXAS INSTRUMENTS). In various embodiments, microprocessor 202 may comprise a System on Chip (SoC); for example, an MT8516B SoC (MEDIATEK, Hsinchu, Taiwan), designed specifically for voice assistance devices. In various embodiments, I-O device 210 may comprise one or more LEDs controlled by one or more LED drivers (e.g., LP55231, available from TEXAS INSTRUMENTS, or IS31FL3236, available from LUMISSIL MICROSYSTEMS, Milpitas, CA). In various embodiments, buttons 212 may comprise tactile buttons. In various embodiments, power management IC 242 may comprise MT6323 (MEDIATEK, Hsinchu, Taiwan) with buck regulator components or an integrated power management IC TPS65910A1 (TEXAS INSTRUMENTS). In various embodiments, sensors 238 may comprise non-limiting haptic, visible light, infrared, and acoustic sensors, among others. Microphone 224 may comprise, for example, a V6 MEMS microphone available from KNOWLES SISONIC (Itasca, IL). In certain embodiments, microphone 224 may comprise a microphone array with built-in advanced DSP algorithms including, but not limited to, ReSpeaker v2, Matrix Creator, PS3 eye, Conexant 4, MiniDSP UMA-8, Microsemi AcuEdge ZLK38AVS, among others.

In accordance with certain aspects of the present disclosure, smart speaker 102 is communicably engaged with one or more remote cloud-based or virtual servers (e.g., application server 110 of FIG. 1) capable of providing ASR-response, NLU-processing, predictive algorithm processing, reminders, alerts, general and specific information for remote management of patient user 22 of FIG. 1 with an acute, chronic, condition, or disease, including but not limited to diabetes, cancer, hypertension, infectious disease, kidney disease, heart failure, among others. In various embodiments, device 102 may be communicably engaged (e.g., via antenna 236) with the plurality of remote patient monitoring devices 244. In accordance with certain embodiments, the plurality of remote patient monitoring devices 244 may include, but are not limited to, continuous glucose monitor (CGM) 106, a glucometer 248, a remote or mobile patient monitor 250, end user smart speaker 102 and/or smart appliance 254. In certain embodiments, patient monitor 250 may comprise one or more physiological sensors configured to measure one or more physiological data for a patient, including EKG, ECG, variable heart rate, blood pressure and the like. Plurality of remote patient monitoring devices 244 may further comprise one or more point-of-care testing (POCT) device, glucose meter, lactate meter, capillary blood collection device, IoT sensor and the like. In certain embodiments, smart speaker 102 may act as a broker between the plurality of remote patient monitoring devices 244 and application server 110 of FIG. 1.

Figure 3:
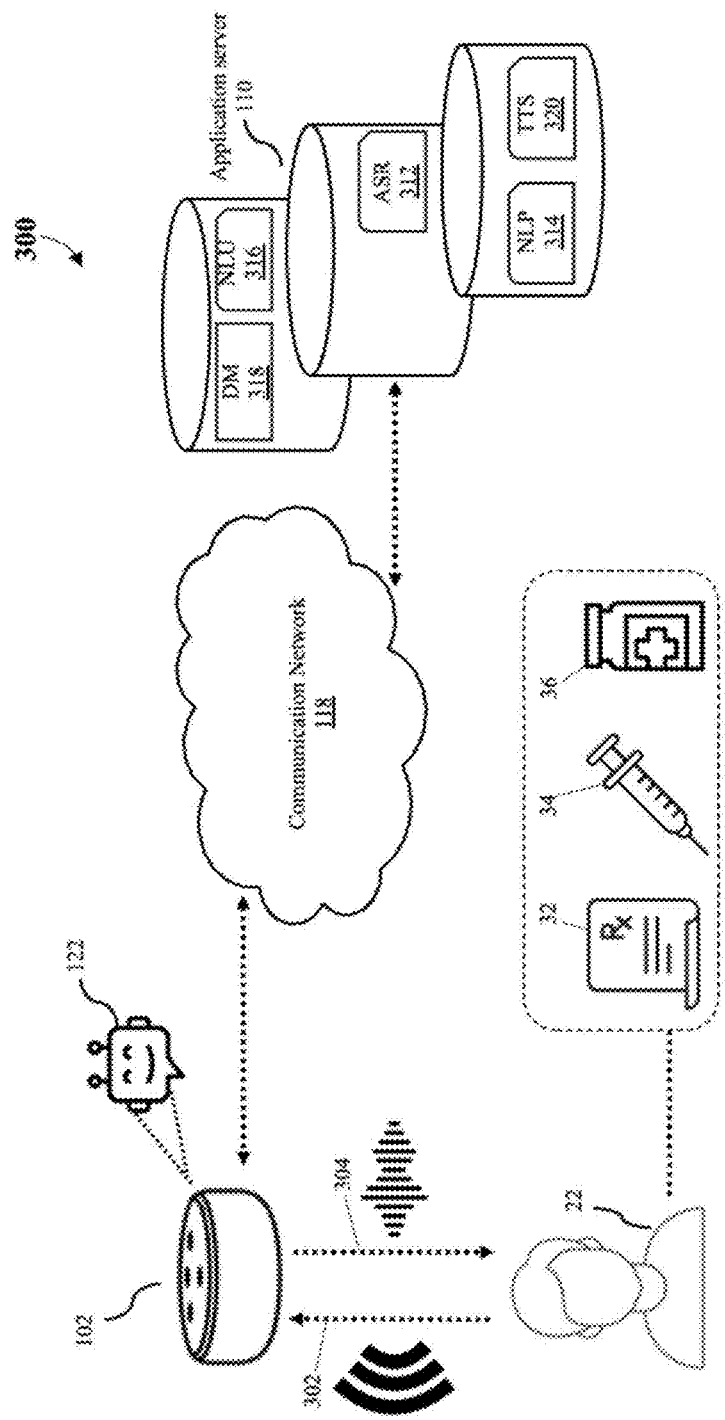
FIG. 3 is a system diagram of a voice-based system for management of type 2 diabetes, in accordance with certain aspects of the present disclosure.

Referring now to FIG. 3 (with cross-references to FIG. 1), a system diagram of a voice-based system 300 for management of type 2 diabetes is shown. In accordance with certain aspects of the present disclosure, system 300 comprises an embodiment of system 100, as shown and described in FIG. 1. In accordance with certain aspects of the present disclosure, smart speaker 102 is communicably engaged with application server 110 via communication network 118 in order to execute a local instance of conversational agent 122. Application server 110 preferably comprises a secured HIPAA-compliant server. In accordance with certain aspects of the present disclosure, application server 110 is configured to provide one or more cloud-based control services to smart speaker 102 via one or more computing module executing on application server 110. In certain embodiments, the one or more cloud-based control services include automated speech recognition (ASR) 312, natural language processing (NLP) 314, natural language understanding (NLU) 316, dialogue management 318, and text-to-speech (TTS) converter 320. In various embodiments, the cloud-based control services, together with smart speaker 102, drive the operations of conversational agent 122 to perform natural language or speech-based automated, dynamic multi-turn conversations with patient user 22. Smart speaker 102 enables patient user 22 to access, interact, and engage with conversational agent 122 to receiving a plurality of generative voice prompts for remotely managing at least one medication prescription, therapeutic dose titration and/or dose regimen. In various embodiments, smart speaker 102 may provide for recording, tracking and monitoring of the user's medication adherence, medication adverse reactions, and the user's behavioral phenotype; including, but not limited to, social demographics, health literacy, technical literacy, illness perception, and clinical complexity, among others. In various embodiments, smart speaker 102 may provide for recording, tracking and monitoring of voice-based interactions between patient user 22 and smart speaker 102; including, but not limited to, device check-in frequency, user speech complexity, clinical flexibility, user personality, and user persistence, among others. In various embodiments, smart speaker 102 listens to and interacts with patient user 22 to determine at least one intent based on NLU of the user's speech. Smart speaker 102 may be configured to record or monitor one or more voice utterances 302 from patient user 22 and transmit them to application server 110 via communication network 118. Communication network 118 may comprise a LAN, WAN, wireless network, cellular network, or Internet connection/protocol. The control service executed by application server 110 may perform ASR 312, NLP 314 and/or NLU 316 on the voice utterances 302 from patient user 22 to determine intents expressed by the utterances via one or more scripted computing skills in accordance with the conversational AI model. In response to an identified intent, the control service may perform one or more corresponding actions. In various embodiments, an action may be performed at the control service or by instructing smart speaker 102 to perform a function, including outputting a generative voice prompt 304 to patient user 22. The combination of smart speaker 102 and one or more applications executed by the control service may serve as conversational agent 122. Conversational agent 122 may facilitate multi-turn conversational interactions, utilizing ASR 312, NLP 314, NLU 316, and TTS 320 conversion to perform said functions, interact with patient user 22, query questions to patient user 22, and provide patient user 22 with one or more prompts for management of type 2 diabetes in patient user 22; including, but not limited to, non-clinical self-management instructions, education, health-related information, nutrition, carb counts, instructional video, tasks, alerts, and the like. In accordance with certain aspects of the present disclosure, conversational agent 122 may provide one or more generative voice prompts to instruct patient 22 to fill a prescription 32 and/or provide instructions for administering a dose of insulin 34 and/or medication 36 in accordance with a clinical protocol. Insulin 34 may comprise basal or prandial insulin in accordance with the clinical protocol. In certain embodiments, medication 36 may comprise a medication for management of type 2 diabetes; including, but not limited to, metformin immediate release, metformin extended release, semaglutide, tirzepatide, liraglutide, retatrutide, dulaglutide, exenatide, exenatide extended release, lixisenatide, empagliflozin, canagliflozin, ertugliflozin, bexagliflozin, sotagliflozin, rosuvastatin, atorvastatin, fluvastatin, lovastatin, pravastatin, simvastatin, and pitavastatin. In certain embodiments, medication 36 may comprise one or more medication for management of hypertension in association with managing type 2 diabetes; including, but not limited to, losartan, valsartan, olmesartan, candesartan, irbesartan, telmisartan, amlodipine, hydrochlorothiazide, chlorthalidone, azilsartan, eprosartan, chlorothiazide, indapamide, metolazone, amiloride, spironolactone, triamterene, eplerenone, lisinopril, captopril, benazepril, enalapril, fosinopril, moexipril, perindopril, quinapril, ramipril and trandolapril. In certain embodiments, medication 36 may further comprise one or more medication for management of hypertension in association with managing type 2 diabetes; including, but not limited to, bumetanide, torsemide, acebutolol, atenolol, betaxolol, bisoprolol, carvedilol, carvedilol phosphate, labetalol, metoprolol tartrate, metoprolol succinate, nadolol, nebivolol, penbutolol, pindolol, propranolol IR, propranolol LA, solatol, timolol, diltiazem, felodipine, isradipine, nicardipine, nifedipine LA, nisoldipine, verapamil, doxazosin, prazosin, terazosin, methyldopa, clonidine, guanfacine, hydralazine, minoxidil, and sacubitril/valsartan.

An object of the present disclosure provides for the combined function of smart speaker 102 and the one or more cloud-based control services of application server 110. According to certain aspects of the present disclosure, application server 110 performs services/functions generally understood and referred to as "cloud computing," "on-demand computing," "software as a service (SaaS)," "platform computing," "network-accessible platform," "cloud services," "data centers," and the like. The term "cloud" generally encompasses a collection of hardware and software that forms a shared pool of configurable computing resources (e.g., networks, servers, storage, applications, services, etc.) suitably provisioned to provide on-demand self-service, network access, resource pooling, elasticity, and measured service, among other features. In various embodiments, a cloud-based control service may be implemented through a SaaS model, including but not limited to: AMAZON Web Services, AMAZON Lex, AMAZON Lambda, available through AMAZON (Seattle, WA); CLOUD AI, GOOGLE Cloud, available through Google, Inc. (Mountain View, Calif.); AZURE AI, available through Microsoft, Inc. (Redmond, Wash.). These services may provide access to one or more remote servers containing hardware and software to operate in conjunction with smart speaker 102.

In lieu of being bound to a specific configuration, the one or more cloud-based control services of application server 110 may provide speech services implementing automated computing modules, ASR 312, NLP 314, and dialogue management 318, TTS 320, and applications providing commands back to smart speaker 102. Computing module ASR 312 may recognize human speech in an audio signal transmitted by smart speaker 102 received from a built-in microphone. Module NLP 314 may determine the intent of patient user 22 based on his or her speech that is recognized by ASR 312. The speech services may also include speech generation functionality that synthesizes speech audio. The control service may also use dialogue management 318 to provide a plurality of system prompts to patient user 22 to coordinate speech; for example, dialogues about medication titration, blood glucose values, or interactions with the user in conjunction with the speech services. Speech dialogues may be used to determine patient user 22 intents using speech prompts. One or more applications may serve as a command interpreter that determines functions or commands corresponding to intents expressed by the user's speech. In alternative embodiments, commands may correspond to functions that are to be performed by smart speaker 102 and a command interpreter may, in those cases, provide smart speaker 102 commands or instructions to smart speaker 102 for implementing such functions. The command interpreter may implement "built-in" capabilities that are used in conjunction with smart speaker 102. The control service may be configured to use a library of installable applications including one or more software applications; for example, medication titration, behavioral modification, and medication persistence.

The one or more cloud-based control services may interact with other network-based services (e.g., AMAZON Lambda) to obtain information, access additional database, application, or services on behalf of patient user 22. Dialogue management 318 may be configured to coordinate dialogues or interactions with patient user 22 based on speech as recognized by ASR 312 and/or interpreted by NLP 314. The one or more cloud-based control services may also use TTS 320 responsive to dialogue management 318 to generate speech for playback on smart speaker 102. These cloud-based control service modules may function based on models or rules, which may include acoustic models, specify grammar, lexicons, phrases, responses, among others, created through various training or machine learning techniques, including a large language model and generative pre-trained transformer. Dialogue management 318 module may utilize dialogue models that specify logic for conducting dialogues with patient user 22. In various embodiments, a dialogue may comprise an alternating sequence of natural language statements or utterances 302 by patient user 22 and system generated speech or textual responses 304 via smart speaker 102. The dialogue models embody logic for creating responses based on received patient user 22 statements to prompt patient user 22 for more detailed information of the intents or to obtain other information from patient user 22.

An application selection component or intent router identifies, selects, and/or invokes installed smart speaker 102 applications and/or application server 110 applications in response to user intents identified by NLP 314. In response to a determined user intent, the intent router can identify one of the installed applications capable of servicing the user intent. The application can be called or invoked to satisfy the user intent or to conduct further dialogue with patient user 22 to further refine the user intent. Each of the installed applications may have an intent specification that defines the serviceable intent. The one or more cloud-based control services may use the intent specifications to detect user utterances, expressions, or intents that correspond to the applications. An application intent specification may include natural language understanding models for use by NLP 314. In addition, one or more installed applications may contain specified dialogue models for creating and coordinating speech interactions with patient user 22. The dialogue models may be used by dialogue management 318 in conjunction with the dialogue models to create and coordinate dialogues with patient user 22 and to determine user intent either before or during operation of the installed applications.

NLP 314 and dialogue management 318 may be configured to use the intent specifications of the applications either to conduct dialogues, to identify expressed intents of patient user 22, identify and use the intent specifications of installed applications, in conjunction with NLP 314 models and dialogue models, to determine when patient user 22 has expressed an intent that can be serviced by the application, and to conduct one or more dialogues with patient user 22. As an example, in response to an utterance 302 by patient user 22, the control service may refer to the intent specifications of multiple applications, including both smart speaker 102 applications and application server 110 applications. The control service may then invoke the corresponding application. Upon invocation, the application may receive an indication of the determined intent and may conduct or coordinate further dialogues with patient user 22 to elicit further intent details. Upon determining sufficient details regarding the user intent, the application may perform its designed functionality in fulfillment of the intent. Smart speaker 102 may be optimally configured for low device operation latency and for parsimonious memory usage to enable prompt responsiveness to enhance user experience.

Figure 4:
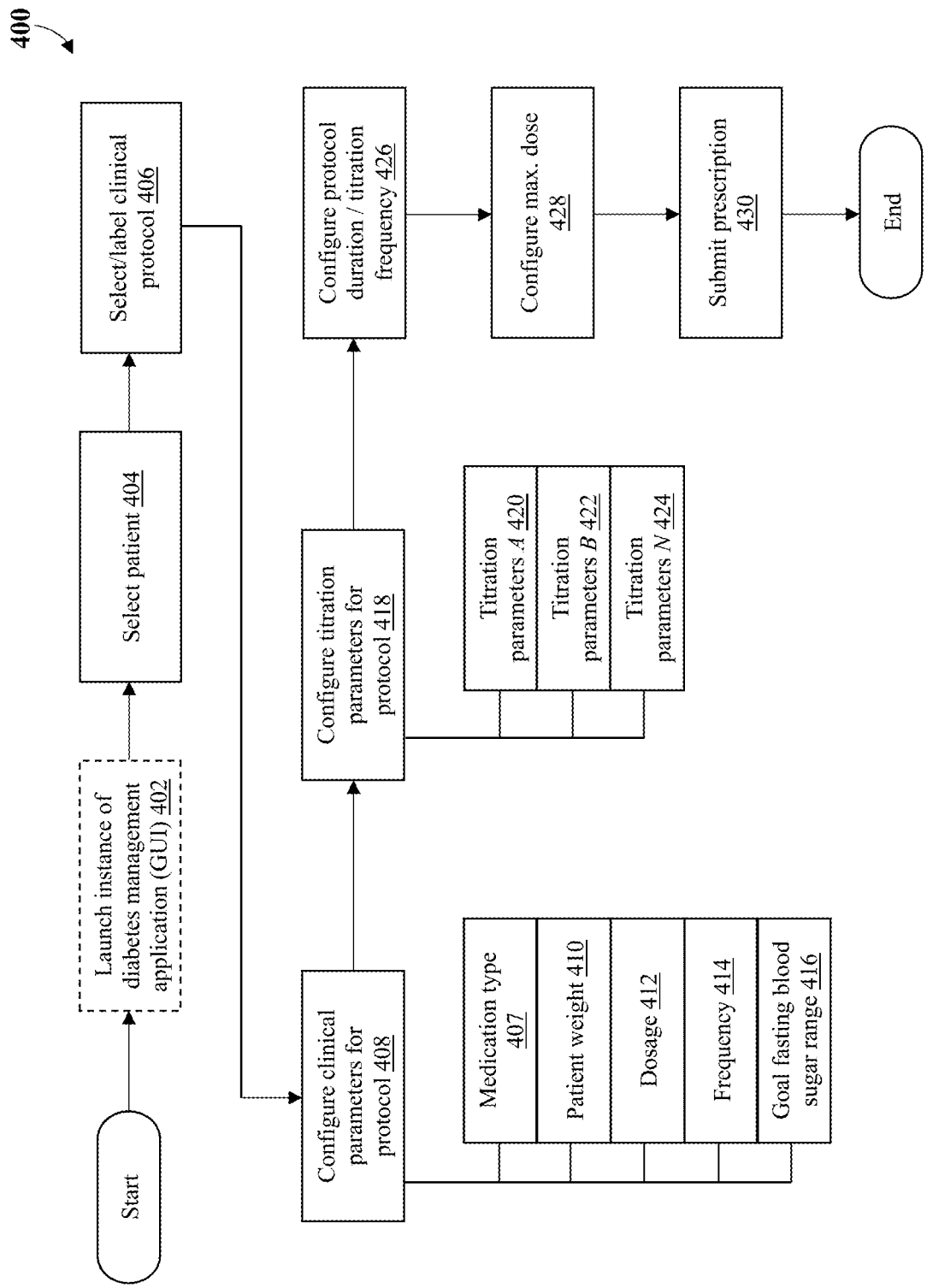
FIG. 4 is a functional block diagram of a routine for configuring a clinical protocol within the voice-based system for management of type 2 diabetes.

Referring now to FIG. 4, a functional block diagram of a routine 400 for configuring a clinical protocol within the voice-based system for management of type 2 diabetes is shown. In accordance with certain aspects of the present disclosure, the voice-based system for management of type 2 diabetes comprises system 100, as shown and described in FIG. 1. In accordance with certain aspects of the present disclosure, routine 400 comprises one or more operations 402-430 to enable a practitioner user (e.g., practitioner user 24 of FIG. 1) to configure a clinical protocol for management of type 2 diabetes in a patient (e.g., patient user 22 of FIG. 1) via a practitioner instance of a diabetes management application (e.g., practitioner instance 120' of diabetes management application 120 of FIG. 1). The operations in routine 400 may be performed in the order presented, in a different order, or simultaneously. Further, in some exemplary embodiments, some of the operations may be omitted, added, modified, skipped, or the like without departing from the scope of the invention In accordance with certain embodiments, routine 400 comprises one or more steps or operations for launching an instance of a diabetes management application (e.g., practitioner instance 120' of diabetes management application 120 of FIG. 1) at a client device associated with the practitioner user (Step 402). The instance of the diabetes management application may comprise a graphical user interface configured to enable the practitioner user in providing a plurality of inputs for configuring a clinical protocol for the patient. In accordance with certain embodiments, routine 400 may comprise one or more steps or operations (e.g., presenting one or more user interface elements) to enable the practitioner user to select a patient to be associated with the clinical protocol (Step 404) and select and label one or more clinical protocols to be associated with that patient (Step 406). Routine 400 may further comprise one or more steps or operations (e.g., presenting one or more user interface elements) to enable the practitioner user to configure one or more clinical parameters for the selected protocol(s) (Step 408). In accordance with certain embodiments, the one or more clinical parameters may include, but are not limited to, parameters for configuring a diabetes medication prescription protocol or other medication prescription protocols 407, patient weight (or other patient data) 410, dosage amount 412, dosage frequency 414 and a goal fasting blood sugar range 416 (e.g., including goal hemoglobin A1C). Routine 400 may further comprise one or more steps or operations (e.g., presenting one or more user interface elements) to enable the practitioner user to configure one or more medication titration parameters for the selected protocol(s) (Step 418). In accordance with certain embodiments, the one or more medication titration parameters for the selected protocol(s) may comprise titration parameters applicable to varying trigger conditions (e.g., blood sugar ranges, hypoglycemic events, hypertensive events, laboratory test result data, and the like). For example, a first set of titration parameters, titration parameters A 420, may comprise a first set of titration parameters for modifying a medication dosage regimen for at least one medication (e.g., a GLP-1 agonist drug, a biguanide drug, or a SGLT-2 inhibitor drug) under a first set of conditions for the patient (e.g., average fasting blood sugar falling within a first specified range). A second set of titration parameters, titration parameters B 422, may comprise a second set of titration parameters for modifying the medication dosage regimen for the at least one medication under a second set of conditions for the patient (e.g., average fasting blood sugar falling within a second specified range). Routine 400 may enable the practitioner user to configured additional titration parameters, e.g., titration parameters N 424, comprising one or more successive titration parameters for modifying the medication dosage regimen for the at least one medication under one or more safety or efficacy conditions for the patient (e.g., blood sugar ranges, hypoglycemic events, hypertensive events, laboratory test result data, and the like). In accordance with certain aspects of the present disclosure, titration parameters N 424 may comprise one or more parameters for terminating the clinical protocol, changing the clinical protocol, and/or temporarily locking the clinical protocol in response to one or more triggering conditions (e.g., safety or efficacy conditions for the patient).

Routine 400 may further comprise one or more steps or operations (e.g., presenting one or more user interface elements) to enable the practitioner user to configure one or more time-based parameters (e.g., protocol duration or titration frequency) for administering the protocol and/or titrating the medication regimen according to the titration parameters (Step 426). Routine 400 may further comprise one or more steps or operations (e.g., presenting one or more user interface elements) to enable the practitioner user to configure a maximum dosage for the medication regimen (Step 428) and submit a prescription to at least one networked server via the practitioner interface (Step 430). In accordance with certain aspects of the present disclosure, the prescription comprises the practitioner-generated inputs received at steps 408-428.

Figure 5:
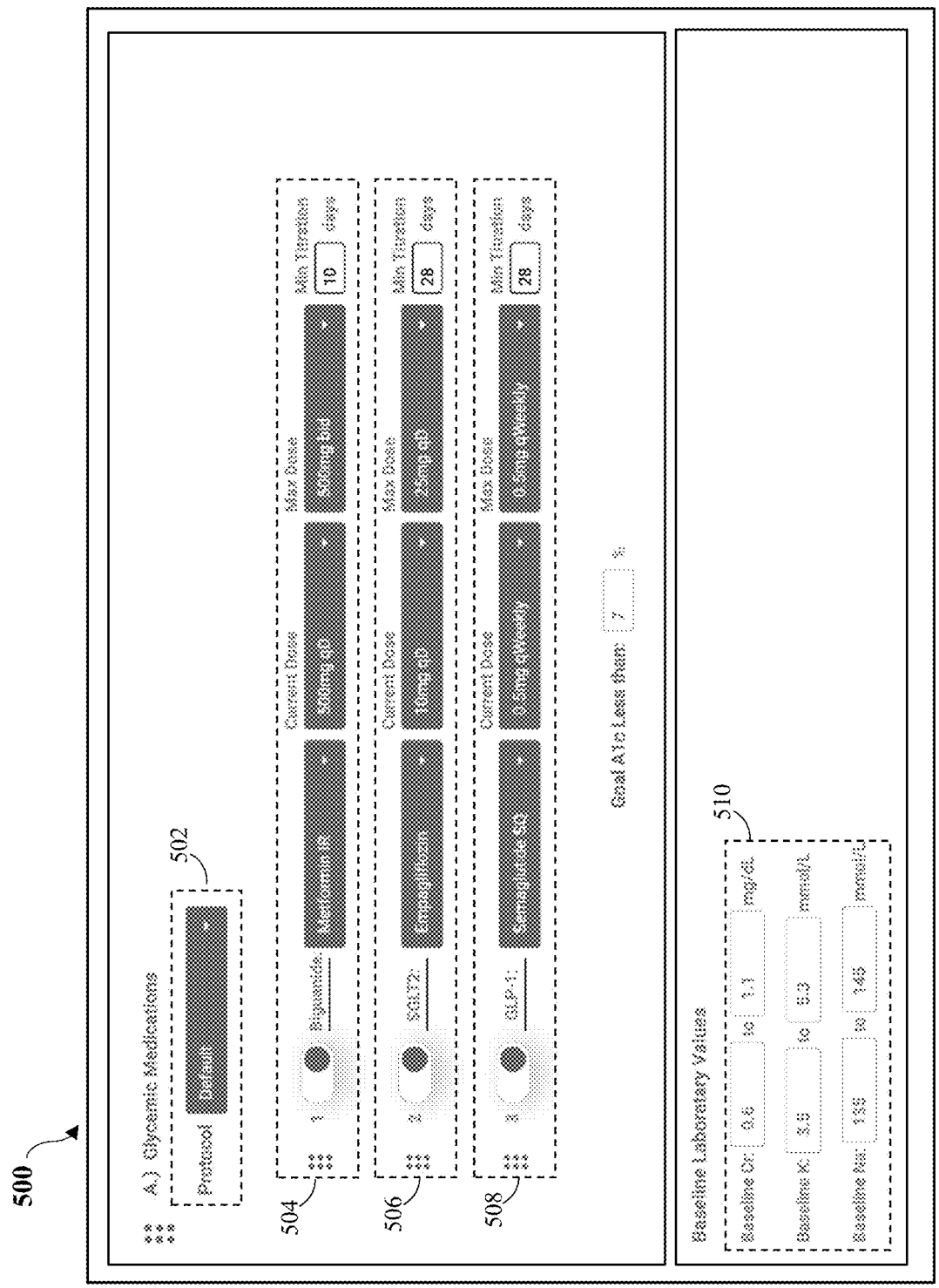
FIG. 5 is an illustration of a user interface associated with a practitioner user within the voice-based system for management of type 2 diabetes.

Referring now to FIG. 5, illustrations of a user interface screen 500 associated with a practitioner instance of a diabetes management application are shown. In accordance with certain aspects of the present disclosure, the practitioner instance of the diabetes management application comprises practitioner instance 120' of diabetes management application 120 of FIG. 1. In accordance with certain embodiments, user interface screen 500 is implemented in accordance with routine 400 of FIG. 4. In accordance with certain embodiments, user interface screen 500 comprises a graphical user interface comprising a plurality of graphical elements 502-510 configured to enable the practitioner user to configure one or more clinical protocol(s) and prescription(s) for a patient. In accordance with certain embodiments, user interface screen 500 may comprise a graphical element 502 configured to enable the practitioner user to select one or more glycemic medication protocols for the patient (e.g., default, conservative, off). In accordance with certain embodiments, each protocol may comprise parameters for a biguanide drug regimen, a SGLT-2 inhibitor drug regimen and a GLP-1 agonist drug regimen. In said embodiments, user interface screen 500 may comprise interface elements 504 for configuring a biguanide drug regimen associated with the selected protocol. Interface elements 504 may comprise a graphical element (e.g., a toggle button) for turning the biguanide drug regimen ON or OFF within the selected protocol; a graphical element for selecting a biguanide drug (e.g., metformin IR), a current (i.e., prescribed) dose, a maximum dosage for titration, and a minimum number of days between titrations. In said embodiments, user interface screen 500 may comprise interface elements 506 for configuring a SGLT-2 inhibitor drug regimen associated with the selected protocol. Interface elements 506 may comprise a graphical element (e.g., a toggle button) for turning the SGLT-2 inhibitor drug regimen ON or OFF within the selected protocol; a graphical element for selecting a SGLT-2 inhibitor drug (e.g., empagliflozin), a current (i.e., prescribed) dose, a maximum dosage for titration, and a minimum number of days between titrations. In said embodiments, user interface screen 500 may comprise interface elements 508 for configuring a GLP-1 agonist drug regimen associated with the selected protocol. Interface elements 508 may comprise a graphical element (e.g., a toggle button) for turning the GLP-1 agonist drug regimen ON or OFF within the selected protocol; a graphical element for selecting a GLP-1 agonist drug (e.g., semaglutide SQ), a current (i.e., prescribed) dose, a maximum dosage for titration, and a minimum number of days between titrations. In certain embodiments, user interface screen 500 may comprise one or more interface elements 510 to enable the practitioner user to input one or more baseline laboratory values for the patient user (e.g., baseline chromium, baseline potassium, and baseline sodium).

Figure 6:
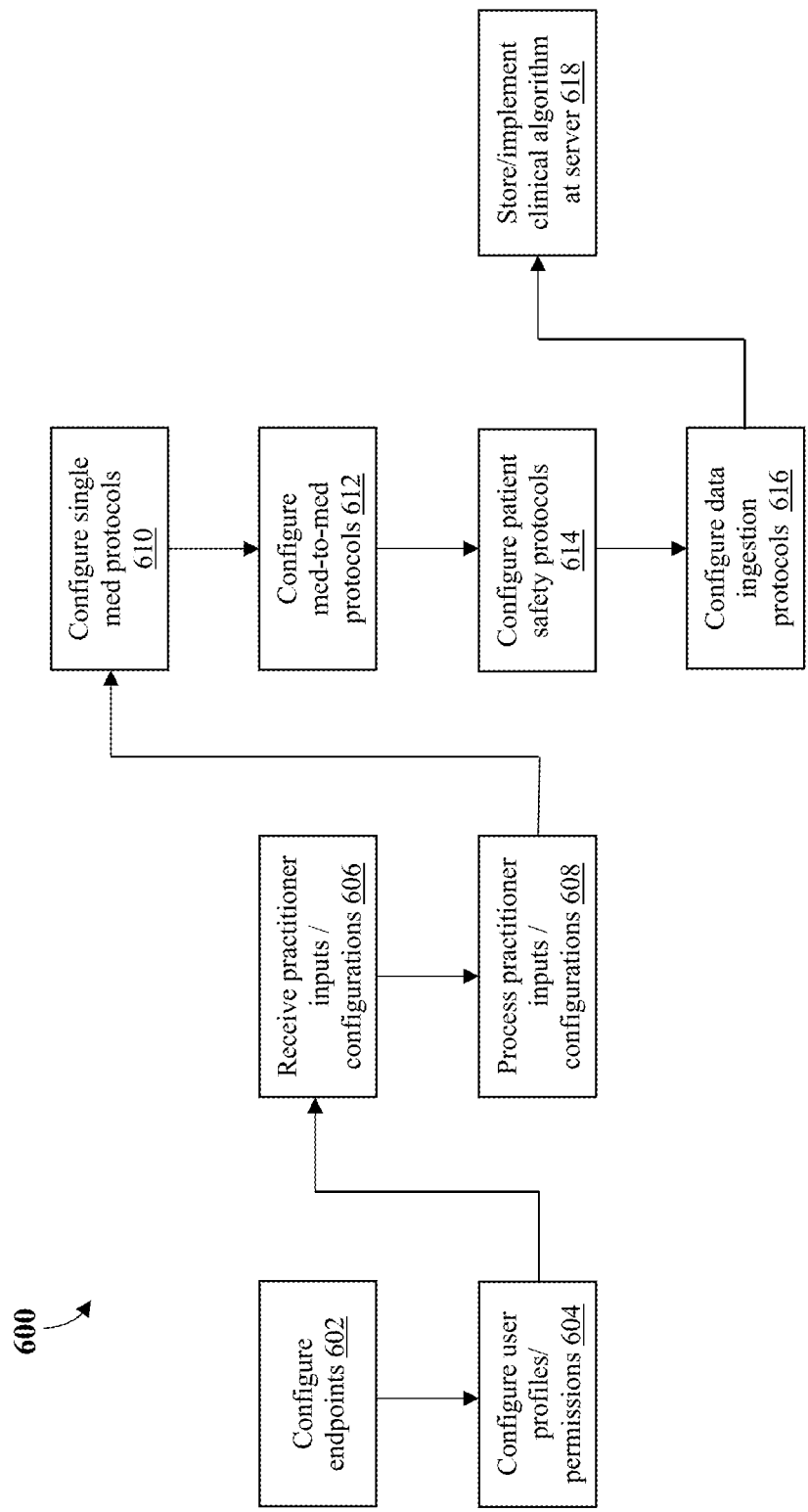
FIG. 6 is a process flow diagram of a routine for configuring a clinical algorithm within the voice-based system for management of type 2 diabetes, in accordance with certain aspects of the present disclosure.

Referring now to FIG. 6, a process flow diagram of a routine 600 for configuring a clinical algorithm within a voice-based system for management of type 2 diabetes is shown. In accordance with certain aspects of the present disclosure, the voice-based system for management of type 2 diabetes comprises system 100 as shown and described in FIG. 1. In certain embodiments, one or more steps or operations of routine 600 may be successive or sequential to one or more steps or operations of routine 400, as shown and described in FIG. 4. In accordance with certain aspects of the present disclosure, routine 600 comprises one or more steps or operations 602-618 for configuring and implementing a clinical algorithm at an application server (e.g., application server 110 of FIG. 1). The one or more steps or operations 602-618 may be embodied as one or more operations of diabetes management application 120 executing on application server 110, as shown and described in FIG. 1. The operations in routine 600 may be performed in the order presented, in a different order, or simultaneously. Further, in some exemplary embodiments, some of the operations may be omitted, added, modified, skipped, or the like without departing from the scope of the invention.

In accordance with certain aspects of the present disclosure, routine 600 may comprise one or more steps or operations for configuring one or more endpoints within the voice-based system for management of type 2 diabetes (Step 602). The one or more endpoints may comprise one or more client devices (e.g., end user device 104 in FIG. 1), one or more remote patient monitoring devices (e.g., CGM 106 in FIG. 1), and/or one or more external data sources (e.g., external EMR/EHR server 130 in FIG. 1). Step 602 may further comprise one or more steps or operations for configuring one or more data transfer protocols between the application server and the one or more endpoints. Routine 600 may proceed by executing one or more steps or operations for configuring one or more user profiles and/or user permissions for one or more users (e.g., patient user 22 and practitioner user 24 of FIG. 1) of the diabetes management application (Step 604). Routine 600 may proceed by executing one or more steps or operations for receiving a plurality of user-generated inputs/configurations via a data transfer protocol with the practitioner instance of the diabetes management application (Step 606). In accordance with certain aspects of the present disclosure, one or more operations of step 606 may be dependent on an output of routine 400 of FIG. 4. Routine 600 may proceed by executing one or more steps or operations for processing the plurality of user-generated inputs/configurations received at step 606 according to one or more data processing steps (Step 608). According to certain aspects of the present disclosure, the one or more data processing steps at step 608 are configured to configure a clinical algorithm within the diabetes management application. In accordance with said aspects, the one or more data processing steps at step 608 further comprise one or more steps or operations for configuring one or more single medication protocol(s) for the patient user (Step 610), configuring one or more medication-to-medication protocol(s) (i.e., multi-medication protocols) for the patient user (Step 612) and configuring one or more safety protocol(s) for the patient user (Step 614). Routine 600 may further comprise one or more steps or operations for configuring one or more data ingestion protocols (e.g., for the one or more endpoints) (Step 616). The one or more data ingestion protocols may comprise protocols for processing clinical data inputs from the one or more endpoints; including, but not limited to, basic metabolic panel data (e.g., sodium, potassium, chloride, bicarbonate, BUN, creatinine, glucose, magnesium, phosphate, calcium, uric acid, and the like), hemoglobin A1C data, medication adherence data based on patient-reported data (e.g., Rx fill data, Rx log data), blood pressure data, physiological sensor data, patient-reported side effects, and the like. Routine 600 may further comprise one or more steps or operations for storing the clinical algorithm at the application server and implementing the clinical algorithm within one or more operations of the diabetes management application (Step 618).

Figure 7:
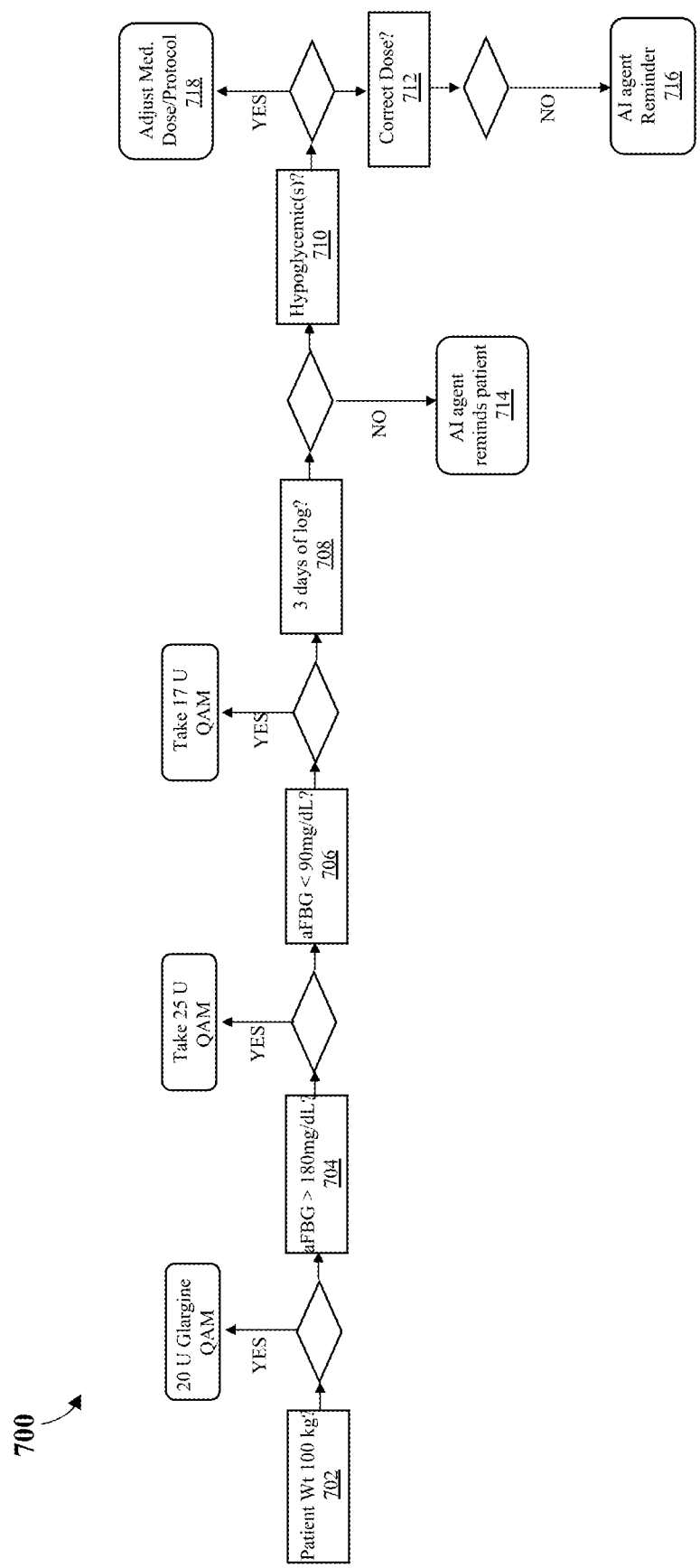
FIG. 7 is a process flow diagram of an exemplary clinical algorithm, in accordance with certain aspects of the present disclosure.

Referring now to FIG. 7, a process flow diagram of an exemplary clinical algorithm 700 is shown. In accordance with certain aspects of the present disclosure, clinical algorithm 700 comprises a non-limiting example of at least one clinical algorithm that may be configured as an output of routine 600 in FIG. 6. Clinical algorithm 700 may further provide an example of a clinical algorithm that may be configured in response to the plurality of practitioner-generated inputs and configurations received pursuant to routine 400 in FIG. 4. Clinical algorithm 700 is intended to be illustrative (i.e., not limiting) and it is anticipated that the functions and operations of the clinical algorithm will be driven by a myriad of configurable parameters for management of type 2 diabetes in a patient. The operations in clinical algorithm 700 may be performed in the order presented, in a different order, or simultaneously. Further, in some exemplary embodiments, some of the operations may be omitted, added, modified, skipped, or the like without departing from the scope of the invention.

In accordance with certain aspects of the present disclosure, clinical algorithm 700 may comprise a sequence of operations 702-718 for medication initiation and titration in a medication regimen for a patient with type 2 diabetes. In accordance with certain embodiments, clinical algorithm 700 may comprise at least one operation based on an input of the patient's weight (e.g., the patient weighs 100 kg) (Block 702). If YES, then clinical algorithm 700 is configured to output a first medication dosage instruction, e.g., administer 20 units of Glargine QAM (0.2 U/kg). In accordance with certain aspects of the present disclosure, the patient reports their fasting blood glucose and medication dosage log for a specified time period (e.g., three consecutive days) via one or more conversational interactions with the conversational AI agent. In response to said data inputs, algorithm 700 may comprise at least one operation to determine whether a patient's average fasting blood sugar over those three days is above 180 mg/dL (Block 704). If YES, then algorithm 700 is configured to titrate the medication dosage (e.g., administer 25 units QAM (+25%)). In accordance with certain aspects of the present disclosure, the patient reports their fasting blood glucose and medication dosage log for a specified time period (e.g., three consecutive days) via one or more conversational interactions with the conversational AI agent. In response to said data inputs, clinical algorithm 700 may comprise at least one operation to determine whether the patient's average fasting blood sugar is below 90 ml/dL (Block 706). If YES, then clinical algorithm 700 is configured to titrate the medication dosage (e.g., administer 17 units QAM (−3 U)).

Clinical algorithm 700 may further comprise at least one operation to determine whether the patient recorded or logged the required data for three consecutive days (Block 708). If NO, then clinical algorithm 700 is configured to drive at least one function of the conversational AI agent to generate a voice-based prompt to remind the patient to log the data and no dose adjustments will be made until three consecutive days of logged data are received (Block 714). Clinical algorithm 700 may further comprise at least one operation to determine whether the patient has a "hypoglycemic event" (Block 710). If YES, then clinical algorithm 700 is configured to drive at least one function of the conversational AI agent to generate a voice-based prompt to instruct a patient to adjust the medication dosage per a predetermined hypoglycemia protocol (Block 718). Clinical algorithm 700 may further comprise at least one operation to determine whether the patient is correctly taking the medication dose as prescribed (e.g., in response to processing the patient log data) (Block 712). If NO, then clinical algorithm 700 is configured to adjust the medication dosage according to the patient-reported data and is configured to drive at least one function of the conversational AI agent to generate a voice-based prompt to the patient (Block 716). For example, if clinical algorithm 700 prescribed 10 units of Glargine QAM and during the three-day adjustment period the patient's average fasting blood sugar is within goal, but the patient reported taking 8 units one night, then 9 units, then 8 units, then clinical algorithm 700 may drive at least one function of the conversational AI agent to instruct the patient to take 9 units (e.g., the maximum dose taken in that period). However, if a patient reports taking some medication doses that are both above the patient's prescription and below the patient's prescription within the same period, then the clinical algorithm 700 will not adjust the medication dosage.

Figure 8:
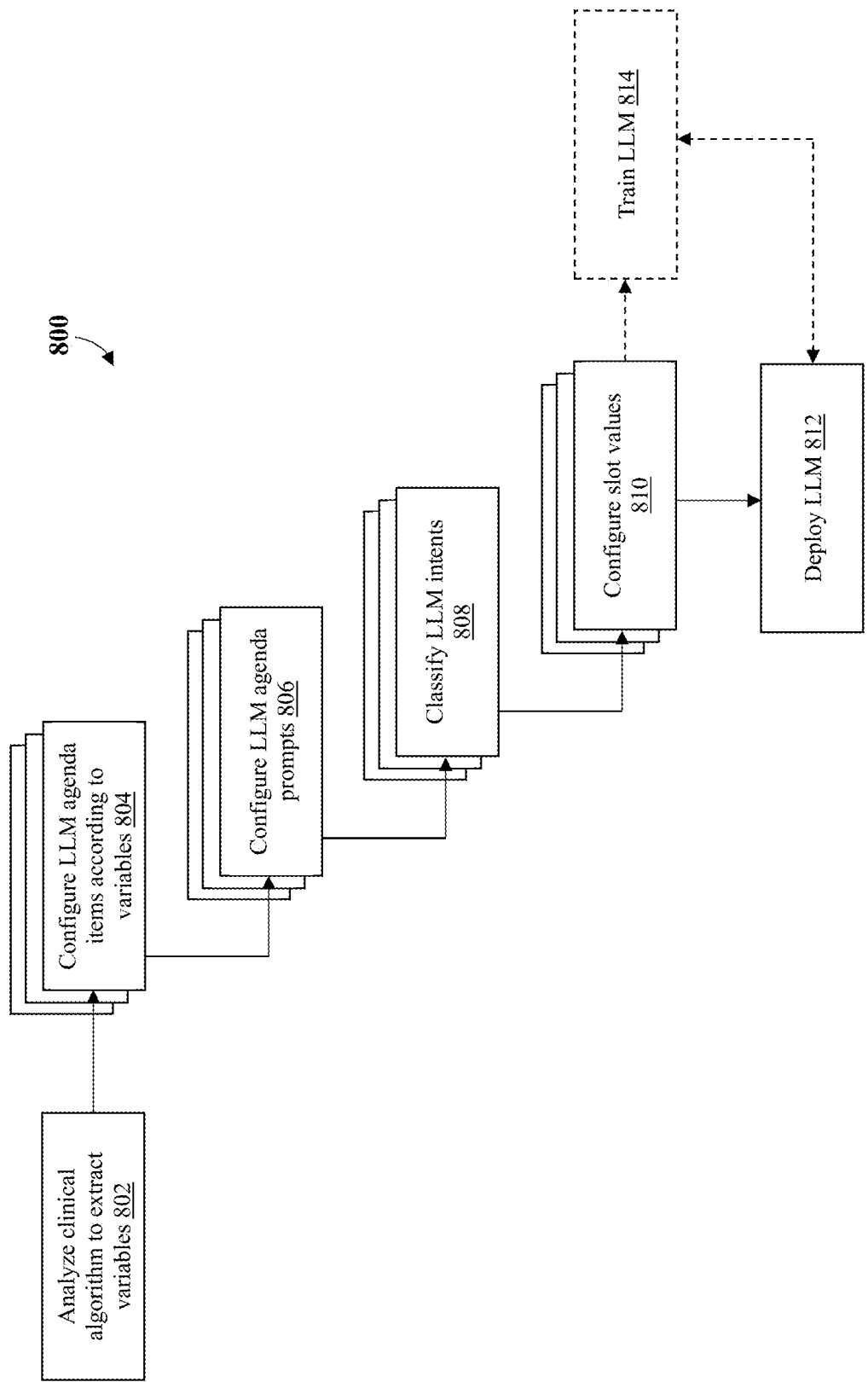
FIG. 8 is a process flow diagram of a routine for configuring a large language model within the voice-based system for management of type 2 diabetes, in accordance with certain aspects of the present disclosure.

Referring now to FIG. 8, a process flow diagram of a routine 800 for configuring a large language model within the voice-based system for management of type 2 diabetes is shown. In accordance with certain aspects of the present disclosure, the voice-based system for management of type 2 diabetes comprises system 100 as shown and described in FIG. 1. In certain embodiments, one or more steps or operations of routine 800 may be successive or sequential to one or more steps or operations of routine 400, as shown and described in FIG. 4, and/or one or more steps or operations of routine 600, as shown and described in FIG. 6. In accordance with certain aspects of the present disclosure, routine 800 comprises one or more steps or operations 802-812 for configuring a large language model at an application server (e.g., application server 110 of FIG. 1). The one or more steps or operations 802-812 may be embodied as one or more processor-executable instructions of large language model engine 121 executing on application server 110, as shown and described in FIG. 1. The operations in routine 800 may be performed in the order presented, in a different order, or simultaneously. Further, in some exemplary embodiments, some of the operations may be omitted, added, modified, skipped, or the like without departing from the scope of the invention.

In accordance with certain aspects of the present disclosure, routine 800 may comprise one or more steps or operations for analyzing one or more clinical algorithm (e.g., pursuant to an output of routine 600 in FIG. 6) to extract one or more variables (Step 802). In accordance with certain embodiments, the one or more variables may comprise one or more clinical parameters configured by the practitioner user pursuant to routine 400 in FIG. 4 (e.g., via user interface screen 500 of FIG. 5). Routine 800 may proceed by executing one or more steps or operations for configuring a plurality of LLM agenda items according to the one or more variables (Step 804). The LLM agenda items may include, for example, a "New Medication Recommendation" item, a "GLP-1 Education" item, a "Medication Initiation" item, a "Medication Titration" item, and other items based on the clinical algorithm(s). Routine 800 may proceed by executing one or more steps or operations for configuring a plurality of agenda prompts according to the plurality of LLM agenda items (Step 806). The plurality of agenda prompts may include, for example, one or more generative prompts associated with a desired outcome of the plurality of LLM agenda items. Routine 800 may proceed by executing one or more steps or operations for classifying one or more LLM intents; e.g., according to each agenda prompt in the plurality of agenda prompts (Step 808). In certain embodiments, classifying the LLM intents may comprise one or more steps or operations for analyzing a plurality of conversational or user-utterance data to create embeddings comprising clusters of semantically similar sentences. In accordance with certain embodiments, the clustered groupings may each comprise an intent, each of which may be classified according to the plurality of agenda prompts. Routine 800 may proceed by executing one or more steps or operations for configuring one or more slot values for the large language model; e.g., corresponding to the LLM intents (Step 810). In accordance with certain embodiments, the slot values comprise different parameters for the user's query/response. Upon completion of steps 802-810, routine 800 may comprise one or more steps or operations for deploying the LLM (e.g., at large language model engine 121) (Step 812). In certain embodiments, routine 800 may comprise one or more steps or operations for training the LLM according to the configurations from steps 802-810 (Step 814). In accordance with certain embodiments, step 814 may comprise analyzing a library of training data from other users of the voice-based system for management of type 2 diabetes. In certain embodiments, one or more operations of step 814 may be performed on a continuous basis in response to new user data.

In accordance with certain aspects of the present disclosure, an example of an output of routine 800 may comprise the LLM configurations shown in Table 1 below.

TABLE 1

Example LLM Configuration 1

| | |
|---|---|
| Agenda Item: | New Medication Recommendation |
| Description: | This item is added to the agenda to initiate a new medication per the clinical algorithm. The purpose of this agenda item is to confirm the patient consents to starting the new medication and answer any questions the patient might have about the new medication. |
| LLM Usage: | Answer specific medication questions based on knowledge base<br>Identify reason (from given list) that patient is apprehensive |
| Slots: | questions_about_med: bool REQUIRED<br>comfortable_starting_med: bool REQUIRED<br>recommendation_confirmation: bool REQUIRED |

In accordance with certain aspects of the present disclosure, another example of an output of routine 800 may comprise the LLM configurations shown in Table 2 below.

TABLE 2

Example LLM Configuration 2

| | |
|---|---|
| Agenda Item: | GLP-1 Education |
| Description: | This idem is added to the agenda when a patient agrees to start a GLP-1 agonist. This item will only occur after the patient has alreadypicked up the GLP-1 agonist. The purpose of this agenda item is to educate the patient on GLP-1 agonist use. Education items include how to administer a GLP-1 agonist (injection site, medication pen, sharps disposal), how to store medication and how to check blood sugars (CGM vs glucometer). |
| LLM Usage: | Answer specific medication questions based on knowledge base |
| Slots: | picked_up_rx: bool REQUIRED<br>needs_education: bool<br>has_CGM: bool<br>understands_blood_sugar_checks: bool |

In accordance with certain aspects of the present disclosure, another example of an output of routine 800 may comprise the LLM configurations shown in Table 3 below.

TABLE 3

Example LLM Configuration 3

| | |
|---|---|
| Agenda Item: | Medication Initiation |
| Description: | This item is added to the agenda when a provider wants to initiate a new medication and the patient has agreed to start taking it. The purpose of this agenda item is to confirm that the patient has picked up the new medication, understands the prescription and is informed about possible side effects. |
| LLM Usage: | Identify issue with picking up Rx<br>Answer specific side effect question based on our knowledge base |
| Slots: | picked_up_rx: bool REQUIRED<br>recommendation_confirmation: bool REQUIRED<br>understands_side_effects: bool REQUIRED<br>issues_with_rx: bool<br>rx_issue: categorical |

In accordance with certain aspects of the present disclosure, another example of an output of routine 800 may comprise the LLM configurations shown in Table 4 below.

TABLE 4

Example LLM Configuration 4

| | |
|---|---|
| Agenda Item: | Medication Titration |
| Description: | This agenda item occurs when a patient checks-in after initiation of a new medication. The purpose of this agenda item is to ask about adherence and side effects and provide a dose adjustment if needed. |
| LLM Usage: | Confirm conditions for medication titration |
| Slots: | rx_started: bool |
| | picked_up_rx: bool |
| | med_adherence_1: bool REQUIRED |
| | med_adherence_2: bool |
| | med_adherence_3: bool |
| | med_adherence_4: bool |
| | med_dose_1: float REQUIRED |
| | med_dose_2: float |
| | med_dose_3: float |
| | med_dose_4: float |
| | med_adherence_confirmation: bool REQUIRED |
| | side_effects_present: bool |
| | side_effects_severity: bool |
| | has_enough_medication: bool |
| | recommendation_confirmation: bool REQUIRED |

Figure 9:
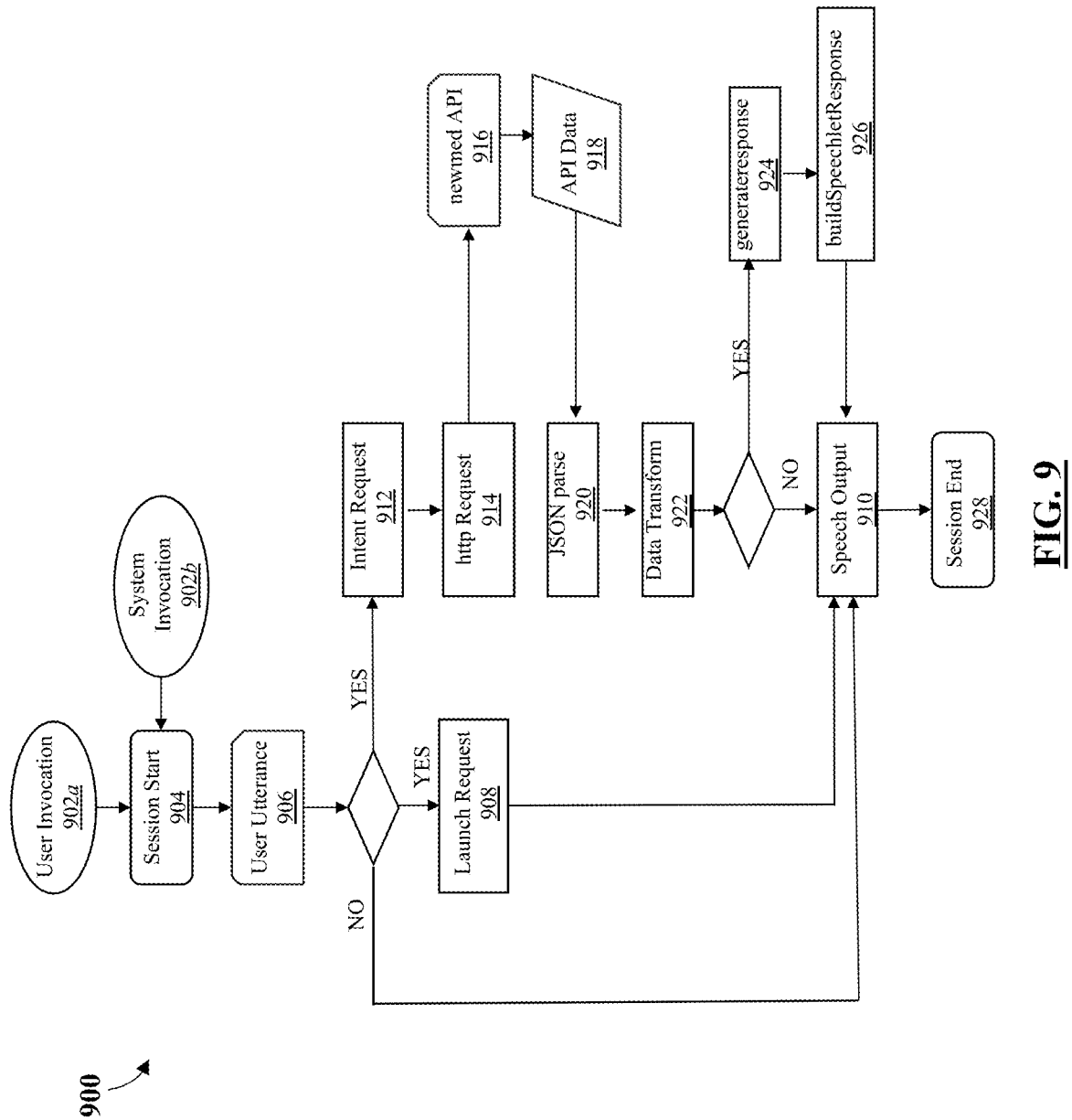
FIG. 9 is a process flow diagram of a routine for processing a user voice input within the voice-based system for management of type 2 diabetes, in accordance with certain aspects of the present disclosure.

Referring now to FIG. 9, a process flow diagram of a routine 900 for executing a user session within a voice-based system for management of type 2 diabetes is shown. In accordance with certain aspects of the present disclosure, the voice-based system for management of type 2 diabetes comprises system 100 as shown and described in FIG. 1. In certain embodiments, one or more steps or operations of routine 900 may be successive or sequential to one or more steps or operations of routine 400, as shown and described in FIG. 4, and/or one or more steps or operations of routine 600, as shown and described in FIG. 6, and/or one or more steps or operations of routine 800, as shown and described in FIG. 8. In accordance with certain aspects of the present disclosure, routine 900 comprises one or more steps or operations 902-928 for receiving and processing a plurality of user utterances to generate a conversational agent output in accordance with a conversational AI model. The one or more steps or operations 902-928 may be embodied as one or more processor-executable instructions of large language model engine 121 and/or conversational agent 122, as shown and described in FIG. 1. The one or more steps or operations in routine 900 may be performed in the order presented, in a different order, or simultaneously. Further, in some exemplary embodiments, some of the operations may be omitted, added, modified, skipped, or the like without departing from the scope of the invention.

In accordance with certain aspects of the present disclosure, routine 900 may comprise one or more steps or operations for invoking one or more custom operations or functions of a conversational agent accessible to a patient in a non-clinical setting and executable via a smart speaker in conjunction with a conversational agent. In various embodiments, a custom operations or functions may comprise an Intent Schema, Slot Types definitions and Sample Utterances. In various embodiments, a developer may define one or more intents in the Intent Schema. In various embodiments, intents may be programmed in JavaScript Object Notation (JSON) data structure, a lightweight data-interchange format, based on a sub-net of the JavaScript programming language. In various embodiments, intents may represent one or more actions to be performed by the conversational agent. In various embodiments, a Sample Utterance may be words spoken by a user to invoke a request. In various embodiments, an intent may possess an intent signature defined to it which starts with an action and sets the type of action's properties. In various embodiments, a Slot may be a statically typed argument that is passed into an intent. In various embodiments, one or more operations or functions of the conversational agent may comprise the steps of a New Session, Launch Request, Intent Request, and a Session End Request.

In accordance with an illustrative example as shown in FIG. 9, routine 900 may comprise a process flow for recommending a new medication (e.g., metformin) to a patient user. Routine 900 may be initiated upon executing one or more steps or operations for receiving a user invocation at a smart speaker device configured to execute an instance of a conversational agent (Step 902a). In accordance with Step 902a, the patient user may speak a wake word utterance (e.g., "Hey UpDoc") to the smart speaker. In certain embodiments, the conversational agent may initiate the system invocation without the use of a wake word (e.g., at one or more designated time intervals) (Step 902b). In response to the invocation, routine 900 may comprise one or more steps or operations to initiate a Session Start to create a new conversation session with the conversational agent (Step 904). Routine 900 may proceed in response to receiving at least one user utterance via the conversational agent (Step 906). Per step 906, the patient user may ask the conversational agent a question (e.g., "What is metformin?"). In various embodiments, a new session may comprise one or more YES or NO process options determined by a switch state with (event.request.type) parameters for either a Launch Request, Intent request, or End Session Request. In accordance with certain instances, a user question may comprise an invocation name (e.g., metformin). In accordance with said instances, routine 900 may execute one or more steps or operations to initiate a Launch Request (Step 908). The conversational agent may respond accordingly using a flash briefing function and providing a Speech Output containing the requested information (Step 910).

In an alternative instance, a User Utterance may comprise the option to advance to an Intent Request where parameters (event.request.intent.name) determine the execution of the domain logic for one or more intent (Step 912). The Intent Request may comprise a user inquiry (e.g., "How does metformin work?"). In accordance with certain embodiments, routine 900 may comprise one or more operations for initiating an http request to retrieve a knowledge base response (Step 914). In accordance with said embodiments, routine 900 may execute one or more steps or operations to perform the http request in accordance with a "newmed" API (Step 916) and receive a response containing the API data (Step 918). In accordance with certain embodiments, API data may be processed through a JSON parse (Step 920) and subsequently manipulated according to one or more data transform operations (Step 922). At this junction, a process option (YES/NO) determines whether to generate a response. In accordance with certain embodiments, if YES, then one or more helper functions may be used to generate a data structure (e.g., returned from a conversational AI engine) and subsequently transmitted to the smart speaker via a generateresponse step (Step 924). A response data structure may comprise a SpeechletResponse (Step 926) that specifies the output text for the smart speaker to speak via Speech Output step 910, as well as whether to end the session via a Session End (Step 928). If NO, The conversational agent may respond accordingly using a flash briefing function and providing a Speech Output (Step 910) and end the session via a Session End (Step 928).

Figure 10:
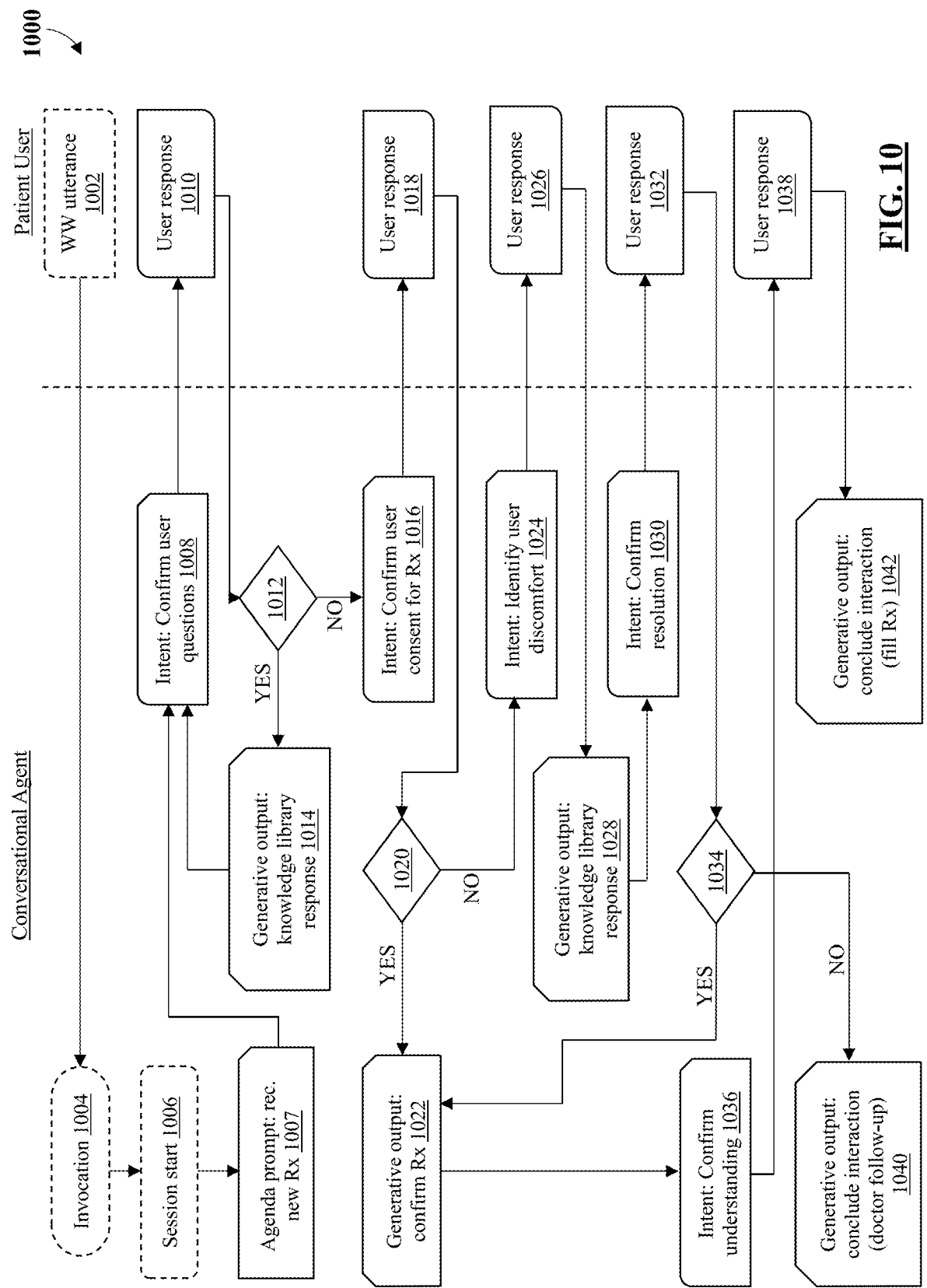
FIG. 10 is a process flow diagram of a multi-turn conversational interaction with a conversational agent of the voice-based system for management of type 2 diabetes, in accordance with certain aspects of the present disclosure.

Referring now to FIG. 10, a process flow block diagram of a multi-turn user interaction 1000 with a conversational agent of the voice-based system for management of type 2 diabetes is shown. In accordance with certain aspects of the present disclosure, the voice-based system for management of type 2 diabetes comprises system 100 as shown and described in FIG. 1. In certain embodiments, one or more steps or operations of multi-turn user interaction 1000 may be successive or sequential to one or more steps or operations of routine 400, as shown and described in FIG. 4, and/or one or more steps or operations of routine 600, as shown and described in FIG. 6, and/or one or more steps or operations of routine 800, as shown and described in FIG. 8. In certain embodiments, one or more steps or operations of multi-turn user interaction 1000 may be embodied within one or more steps or operations of routine 900, as shown and described in FIG. 9. In accordance with certain embodiments, multi-turn user interaction 1000 may comprise a plurality of multi-turn user interactions 1002-1042 for initiating a new medication for the patient user according to a conversational AI model agenda item. The one or more steps or operations in multi-turn user interaction 1000 may be performed in the order presented, in a different order, or simultaneously. Further, in some exemplary embodiments, some of the operations may be omitted, added, modified, skipped, or the like without departing from the scope of the invention.

In accordance with certain aspects of the present disclosure, a session of multi-turn user interaction 1000 may be initiated upon a wake word utterance (Block 1002) by a patient user to a smart speaker (e.g., smart speaker 102 of FIG. 1) configured to execute a conversational agent (e.g., conversational agent 122 of FIG. 1) of the voice-based system for management of type 2 diabetes. The conversational agent may process the wake word utterance as a session invocation (Block 1004) and instantiate a session start (Block 1006) of multi-turn user interaction 1000. In accordance with certain aspects of the present disclosure, the conversational agent may be configured to generate a generative voice output according to a conversational AI model agenda item for recommending a new medication for the patient user (Block 1007). The conversational agent may proceed by generating a generative voice output to prompt the patient user to confirm whether the patient user has any questions about the new medication (Block 1008). The patient user provides a voice response to the conversational agent in response to the generative voice prompt to confirm whether the patient user has any questions (Block 1010). Multi-turn interaction 1000 may comprise a decision block 1012 for driving the next turn in the multi-turn interaction based on the content of the user response from block 1010. If user response 1010 comprises a YES response (i.e., the patient user has questions about the new medication), the conversational agent proceeds by processing the patient user's question(s) according to the conversational AI model to generate a generative voice output comprising a knowledge library response to the patient user's question(s) (Block 1014). In accordance with certain embodiments, multi-turn interaction 1000 may repeat the interaction sequence of blocks 1008-1014 until all of the patient user's questions about the new medication have been answered. If user response 1010 comprises a NO response (i.e., the patient user does not have questions about the new medication), then the conversational agent proceeds by generating a generative voice prompt to confirm whether the patient user consents (i.e., agrees to take) to the new medication (Block 1016). The patient user provides a voice response to the conversational agent in response to the generative voice prompt to indicate consent to the new medication (Block 1018).

Multi-turn interaction 1000 may comprise a decision block 1020 for driving the next turn in the multi-turn interaction based on the content of the user response from block 1018. If user response 1018 comprises a NO response (i.e., the patient user does not consent to the new medication), the conversational agent proceeds by generating a generative voice output to prompt the user to identify issues/discomfort with the new medication (Block 1024). The patient user provides a voice response to the conversational agent in response to the generative voice prompt to identify issues/discomfort with the new medication (Block 1026). The conversational agent proceeds by processing the user response from block 1026 according to the conversational AI model to determine the patient user's issue with the new medication and generates a generative voice output comprising a knowledge library response to the patient user's issue (Block 1028). The conversational agent proceeds by generating a generative voice output to prompt the user to confirm whether the user's issue/discomfort with the new medication has been resolved (Block 1030). The patient user provides a voice response to the conversational agent in response to the generative voice prompt to confirm resolution (Block 1032). Multi-turn interaction 1000 may comprise a decision block 1034 for driving the next turn in the multi-turn interaction based on the content of the user response from block 1032. If user response 1032 comprises a NO response (i.e., the patient user's issue/discomfort with the new medication has not been resolved), the conversational agent proceeds by generating a generative voice output to instruct the patient user to follow-up with the patient's primary care provider and concludes the interaction (Block 1040). If user response 1032 comprises a YES response (i.e., the issue/discomfort with the new medication has been resolved), then multi-turn interaction 1000 proceeds to block 1022.

If user response 1018 comprises a YES response (i.e., the patient consents to the new medication), the conversational agent proceeds by generating a generative voice output to confirm the new prescription (Block 1022). The conversational agent proceeds by generating a generative voice output to prompt the user to confirm one or more aspects of the new prescription (e.g., pharmacy location, prescription start date, etc.) (Block 1036). The patient user provides a voice response to the conversational agent in response to the generative voice output to confirm understanding (Block 1038). The conversational agent proceeds by generating a generative voice output to confirm the prescription has been sent to the patient user's pharmacy and concludes the interaction (Block 1042).

In accordance with certain aspects of the present disclosure, data from each turn of multi-turn interaction 1000 is stored in an application database (e.g., application database 102 of FIG. 1). The diabetes management application (e.g., diabetes management application 120 of FIG. 1) is configured to process the data to execute one or more operations; for example, provide a notification to the provider user that the patient user has an unresolved issue for follow-up or provide a prescription for the new medication to a third-party server (e.g., pharmacy).

An illustrative example of multi-turn interaction 1000 may be embodied as Conversation Flow 10-1, as shown below.

Conversation Flow 10-1

Patient user: "[wake word]"

Conversational Agent: "Based on your latest numbers, your diabetes is still not well controlled. To help better control your blood sugars, your doctor recommends that we start a once-a-day oral medication called metformin. Have you heard of this medication?"

Patient user: "Yes" [or "No" ]

Conversational Agent: "Metformin is one of the first line treatments for diabetes. The main side effect of metformin in 10% of patients can be stomach upset, but it reduces the risk of heart attacks by 50%. Do you have any questions about metformin?"

Patient user: "No"

Conversational Agent: Are you comfortable with your doctor starting metformin at this time?

Patient user: "Yes"

Conversational Agent: "Ok great, I'll notify your doctor so they can send a prescription to your pharmacy. Once you've picked this up and are ready to start, check back in with me. Do you understand?"

Patient user: "Yes"

An illustrative example of multi-turn interaction 1000 may be embodied in Conversation Flow 10-2, as shown below.

Conversation Flow 10-2

Conversational Agent: "Do you have any questions about starting semaglutide?"

Patient user: "Yes"

Conversational Agent: "What do you want to know?"

Patient user: "[specific question]"

Conversational Agent: "[knowledge base response]"

Conversational Agent: "Do you have any other questions?"

[repeat block until all questions have been answered]

An illustrative example of multi-turn interaction 1000 may be embodied in Conversation Flow 10-3, as shown below.

Conversation Flow 10-3

Conversational Agent: "Are you comfortable with starting semaglutide at this time?"

Patient user: "No"

Conversational Agent: "It's normal to feel apprehensive about starting semaglutide. What makes you feel uncomfortable about this?"

Patient user: "[reason for discomfort]"

Conversational Agent: "[knowledge base response]"

Conversational Agent: "Do you have any other questions about semaglutide?"

Patient user: "No"

Conversational Agent: "Now that we've talked about it a little, how do you feel about starting semaglutide?"

Patient user: "I still don't want it."

Conversational Agent: "That's perfectly ok. I'll let your doctor know that you're not ready to start semaglutide."

Figure 11:
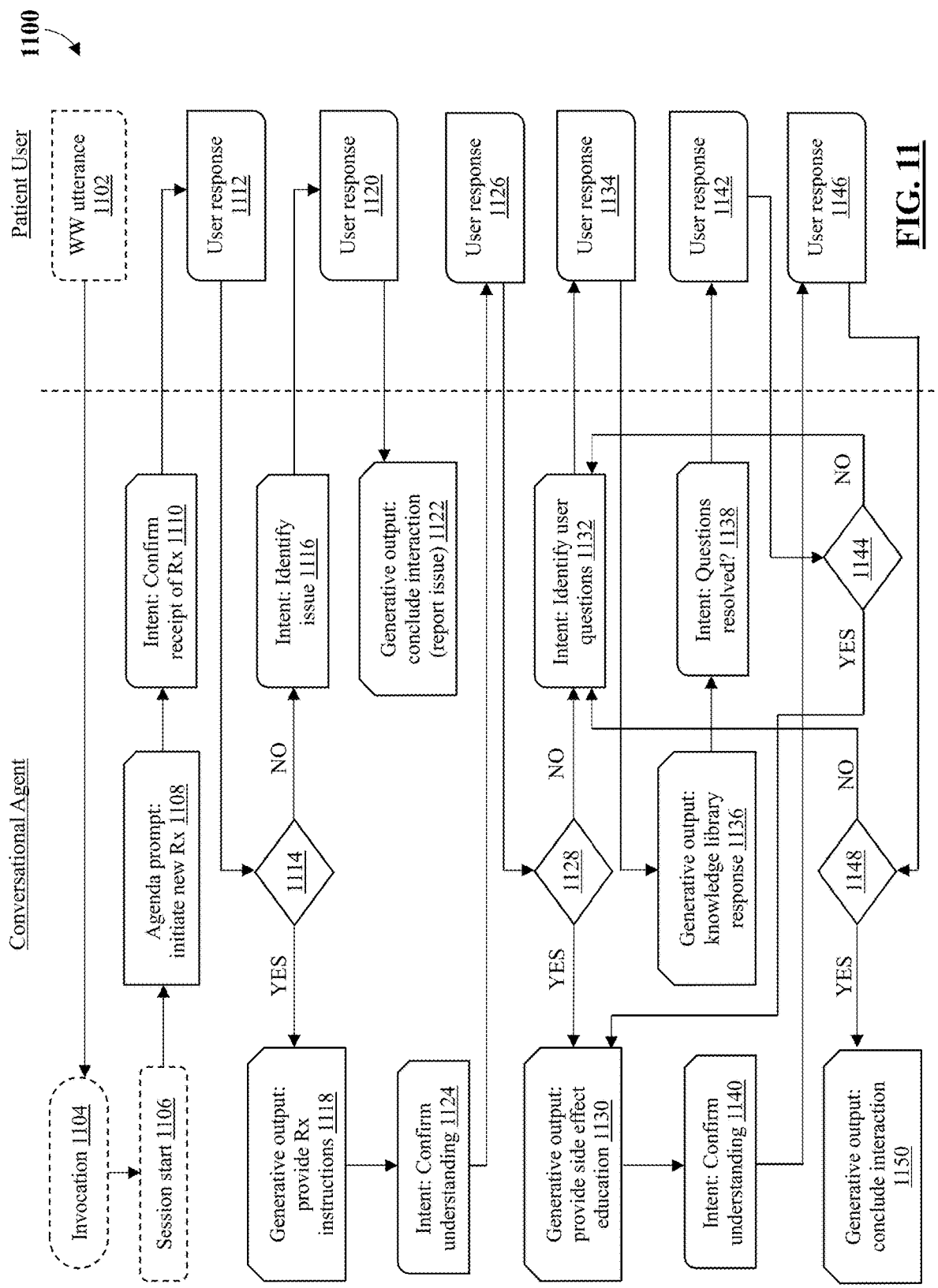
FIG. 11 is a process flow diagram of a multi-turn conversational interaction with a conversational agent of the voice-based system for management of type 2 diabetes, in accordance with certain aspects of the present disclosure.

Referring now to FIG. 11, a process flow block diagram of a multi-turn user interaction 1100 with a conversational agent of the voice-based system for management of type 2 diabetes is shown. In accordance with certain aspects of the present disclosure, the voice-based system for management of type 2 diabetes comprises system 100 as shown and described in FIG. 1. In certain embodiments, one or more steps or operations of multi-turn user interaction 1100 may be successive or sequential to one or more steps or operations of routine 400, as shown and described in FIG. 4, and/or one or more steps or operations of routine 600, as shown and described in FIG. 6, and/or one or more steps or operations of routine 800, as shown and described in FIG. 8. In certain embodiments, one or more steps or operations of multi-turn user interaction 1100 may be embodied within one or more steps or operations of routine 900, as shown and described in FIG. 9. In certain embodiments, one or more aspects of multi-turn user interaction 1100 may be driven by, or otherwise dependent upon, one or more outputs of multi-turn user interaction 1000 of FIG. 10. The one or more steps or operations in multi-turn user interaction 1100 may be performed in the order presented, in a different order, or simultaneously. Further, in some exemplary embodiments, some of the operations may be omitted, added, modified, skipped, or the like without departing from the scope of the invention.

In accordance with certain aspects of the present disclosure, a session of multi-turn user interaction 1100 may be initiated upon a wake word utterance (Block 1102) by a patient user to a smart speaker (e.g., smart speaker 102 of FIG. 1) configured to execute a conversational agent (e.g., conversational agent 112 of FIG. 1) of the voice-based system for management of type 2 diabetes. The conversational agent may process the wake word utterance as a session invocation (Block 1104) and instantiate a session start (Block 1106) of multi-turn user interaction 1100. In accordance with certain aspects of the present disclosure, the conversational agent may be configured to generate a generative voice output according to a conversational AI model agenda item for initiating a new medication regimen for the patient user (Block 1108). The conversational agent may proceed by generating a generative voice output to prompt the patient user to confirm receipt of the medication (Block 1110). The patient user provides a voice response to the conversational agent in response to the generative voice prompt to confirm receipt of the medication (Block 1112). Multi-turn interaction 1100 may comprise a decision block 1114 for driving the next turn in the multi-turn interaction based on the content of the user response from block 1112. If user response 1112 comprises a NO response (i.e., the patient user has not received the new medication), the conversational agent may proceed by generating a generative voice output to prompt the patient user to identify the issue with obtaining the new medication (Block 1116). The patient user provides a voice response to the conversational agent in response to the generative voice prompt to specify the issue with obtaining the new medication (Block 1120). The conversational agent proceeds by generating a generative voice output to report the issue (e.g., to a practitioner user) and conclude the interaction (Block 1122).

If user response 1112 comprises a YES response (i.e., the patient user confirms receipt of the new prescription), then the conversational agent proceeds by generating a generative voice output providing dosage instructions to the patient user per the clinical protocol (Block 1118). The conversational agent proceeds by generating a generative voice prompt to confirm the patient user's understanding of the dosage instructions (Block 1124). The patient user provides a voice response to the conversational agent in response to confirm the patient user's understanding of the dosage instructions (Block 1126). Multi-turn interaction 1100 may comprise a decision block 1128 for driving the next turn in the multi-turn interaction based on the content of the user response from block 1126. If user response 1126 comprises a NO response (i.e., the patient user does not understand the dosage instructions), the conversational agent proceeds by generating a generative voice output to prompt the user to identify questions with the dosage instructions (Block 1132). The patient user provides a voice response to the conversational agent in response to the generative voice prompt to identify questions with the dosage instructions (Block 1134). The conversational agent proceeds by processing the user response from block 1134 according to the conversational AI model to determine the patient user's issue with the new medication and generates a generative voice output comprising a knowledge library response to the patient user's questions (Block 1136). The conversational agent proceeds by generating a generative voice output to prompt the user to confirm whether the user's questions have been resolved (Block 1138). The patient user provides a voice response to the conversational agent in response to the generative voice prompt to confirm resolution (Block 1142). Multi-turn interaction 1100 may comprise a decision block 1144 for driving the next turn in the multi-turn interaction based on the content of the user response from block 1142. If user response 1142 comprises a NO response (i.e., the patient user's questions have not been resolved), then multi-turn interaction 1100 proceeds to block 1132. If user response 1142 comprises a YES response (i.e., the patient user's questions have been resolved), then multi-turn interaction 1100 proceeds to block 1130. If user response 1126 comprises a YES response (i.e., the patient confirms understanding of the medication dosing instructions), the conversational agent proceeds by generating a generative voice output to provide education of one or more side effects of the new medication to the patient user (Block 1130). The conversational agent proceeds by generating a generative voice output to prompt the user to confirm understanding of the side effects of the new medication (Block 1140). The patient user provides a voice response to the conversational agent in response to the generative voice output to confirm understanding of the side effects of the new medication (Block 1146). Multi-turn interaction 1100 may comprise a decision block 1148 for driving the next turn in the multi-turn interaction based on the content of the user response from block 1146. If user response 1146 comprises a NO response (i.e., the patient user does not understand the side effect), then multi-turn interaction 1100 proceeds to block 1132. If user response 1146 comprises a YES response (i.e., the patient user understands the side effects), then conversational agent proceeds by generating a generative voice output to provide at least one check-in instruction and concludes the interaction (Block 1150).

In accordance with certain aspects of the present disclosure, data from each turn of multi-turn interaction 1100 is stored in an application database (e.g., application database 112 of FIG. 1). The diabetes management application (e.g., diabetes management application 110 of FIG. 1) is configured to process the data to execute one or more operations; for example, provide a notification to the provider user that the patient user has started the new prescription.

An illustrative example of multi-turn interaction 1100 may be embodied as Conversation Flow 11-1, as shown below.

Conversation Flow 11-1
Patient user: "[wake word]"
Conversational agent: "Have you picked up the new prescription we sent called Glargine?"
Patient user: "Yes"
Conversational agent: "Great, based on your sugar readings, your doctor and I would like you to start taking 10 units of Glargine every night before you go to bed. Do you understand?"
Patient user: "Yes"
Conversational agent: "Great! The main side effect to look out for with Glargine is [side effect]. Check back in with me tomorrow. Do you understand?"
Patient user: "Yes"

Another illustrative example of multi-turn interaction 1100 may be embodied as Conversation Flow 11-2, as shown below.

Conversation Flow 11-2
Conversational agent: "Have you picked up the new prescription we sent called Lispro?"
Patient user: "Yes"
Conversational agent: "Great, based on your sugar readings, your doctor and I would like you to start taking 4 units of Lispro right before breakfast, lunch and dinner, every day. Do you understand?"

Another illustrative example of multi-turn interaction 1100 may be embodied as Conversation Flow 11-3, as shown below.

Conversation Flow 11-3
Patient user: "[wake word]"
Conversational agent: "Have you picked up the new prescription we sent for metformin immediate release?"
Patient user: "Yes"
Conversational agent: "Great, to start, take one 500 mg tablet of metformin immediate release every evening before bed. Do you understand?"
Patient user: "Yes"
Conversational agent: "Great! The main side effect to look out for with metformin is stomach upset. Our next phase starts Monday, I'll remind you. Feel free to check in before then."

Another illustrative example of multi-turn interaction 1100 may be embodied as Conversation Flow 11-4, as shown below.

Conversation Flow 11-4
Conversational agent: "Have you picked up the new prescription we sent called Glargine?"
Patient user: "No"
Conversational agent: "Have you had any issues picking up the prescription?"
Patient user: "No"
Conversational agent: "Ok no worries, check back in when you've picked up the prescription. Do you understand?"

Another illustrative example of multi-turn interaction 1100 may be embodied as Conversation Flow 11-5, as shown below.

Conversation Flow 11-5
Conversational agent: "Have you had any issues picking up the prescription?"
Patient user: "Yes"
Conversational agent: "What was the issue?"
Patient user: "It wasn't at the pharmacy"
Conversational agent: "Sorry to hear that! I will inform your doctor right away. I'll let you know when this issue is resolved."

Another illustrative example of multi-turn interaction 1100 may be embodied as Conversation Flow 11-6, as shown below.

Conversation Flow 11-6
Conversational agent: "Have you picked up the new prescription we sent called Glargine?"
Patient user: "No"
Conversational agent: "Have you had any issues picking up the prescription?"

Patient user: "Yeah, the pharmacist said they didn't have it."

Conversational agent: "Sorry to hear that! [generative response]"

Another illustrative example of multi-turn interaction 1100 may be embodied as Conversation Flow 11-7, as shown below.

Conversation Flow 11-7

[Patient has Question about Side Effects]

Conversational agent: "The main side effect to look out for with Glargine is [side effect]. Check back in with me tomorrow. Do you understand?"

Patient user: "[question about side effects]"

Conversational agent: "[knowledge base response]"

Figure 12:
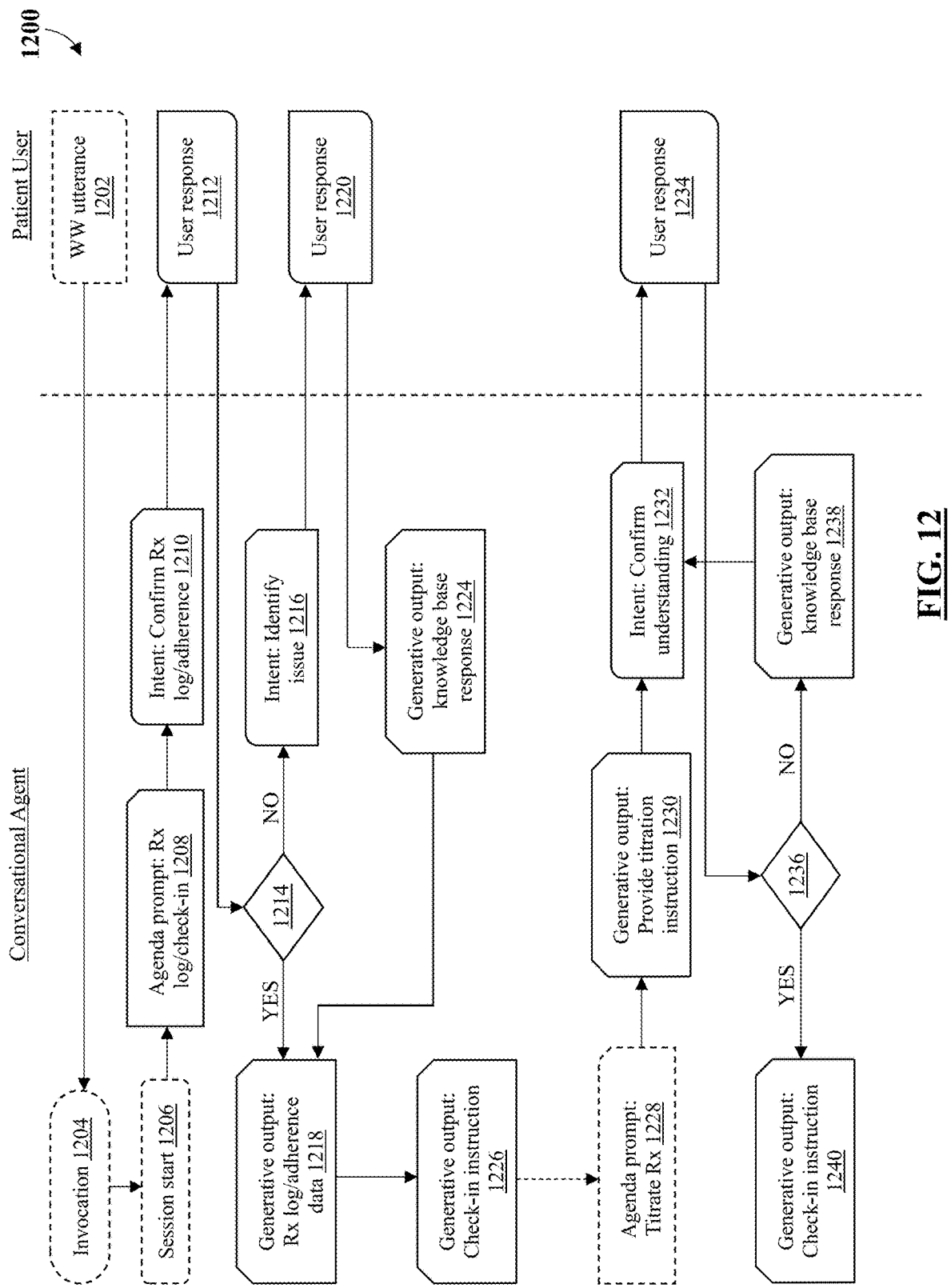
FIG. 12 is a process flow diagram of a multi-turn conversational interaction with a conversational agent of the voice-based system for management of type 2 diabetes, in accordance with certain aspects of the present disclosure.

Referring now to FIG. 12, a process flow block diagram of a multi-turn user interaction 1200 for a conversational agent of the voice-based system for management of type 2 diabetes is shown. In accordance with certain aspects of the present disclosure, the voice-based system for management of type 2 diabetes comprises system 100 as shown and described in FIG. 1. In certain embodiments, one or more steps or operations of multi-turn user interaction 1200 may be successive or sequential to one or more steps or operations of routine 400, as shown and described in FIG. 4, and/or one or more steps or operations of routine 600, as shown and described in FIG. 6, and/or one or more steps or operations of routine 800, as shown and described in FIG. 8. In certain embodiments, one or more steps or operations of multi-turn user interaction 1200 may be embodied within one or more steps or operations of routine 900, as shown and described in FIG. 9. In certain embodiments, one or more aspects of multi-turn user interaction 1200 may be driven by, or otherwise dependent upon, one or more outputs of multi-turn user interaction 1000 of FIG. 10 and/or multi-turn user interaction 1100 of FIG. 11. The one or more steps or operations in multi-turn user interaction 1200 may be performed in the order presented, in a different order, or simultaneously. Further, in some exemplary embodiments, some of the operations may be omitted, added, modified, skipped, or the like without departing from the scope of the invention.

In accordance with certain aspects of the present disclosure, a session of multi-turn user interaction 1200 may be initiated upon a wake word utterance (Block 1202) by a patient user to a smart speaker (e.g., smart speaker 102 of FIG. 1) configured to execute a conversational agent (e.g., conversational agent 122 of FIG. 1) of the voice-based system for management of type 2 diabetes. The conversational agent may process the wake word utterance as a session invocation (Block 1204) and instantiate a session start (Block 1206) of multi-turn user interaction 1200. In accordance with certain aspects of the present disclosure, the conversational agent may be configured to generate a generative voice output according to a conversational AI model agenda item for initiating a medication log and patient check-in (Block 1208). The conversational agent may proceed by generating a generative voice output to prompt the patient user to confirm adherence to the assigned medication regimen and receive one or more medication log entries (Block 1210). The patient user provides a voice response to the conversational agent in response to the generative voice prompt to confirm adherence and/or provide one or more medication log entries (Block 1212). Multi-turn interaction 1200 may comprise a decision block 1214 for driving the next turn in the multi-turn interaction based on the content of the user response from block 1212. If user response 1212 comprises a NO response (i.e., the patient user has not adhered to the medication regimen or fails to provide one or more log entries), the conversational agent may proceed by generating a generative voice output to prompt the patient user to identify the issue with adherence and/or log entries (Block 1216). The patient user provides a voice response to the conversational agent in response to the generative voice prompt to specify the adherence or medication log issue (Block 1220). The conversational agent proceeds by generating a generative voice output to provide a knowledge base response according to the issue with adherence and/or log entries (Block 1224). Multi-turn interaction 1200 may proceed to block 1218. If user response 1212 comprises a YES response (i.e., the patient user is adherent and/or provides medication log data), then the conversational agent proceeds by generating a generative voice output confirming the user input(s) (Block 1218). The conversational agent proceeds by generating a generative voice prompt to provide check-in and/or log instructions to the user (Block 1226). In certain interactions, block 1226 may comprise a generative voice output to conclude the interaction with the patient user.

In certain interactions, multi-turn interaction 1200 may proceed according to a conversational AI model agenda prompt for titrating the patient user's medication dosage according to the clinical algorithm (Block 1228). The conversational agent may proceed by generating a generative voice output comprising a titration instruction for the patient user's medication (Block 1230) and a generative voice output to prompt the user to confirm understanding of the titration instruction (Block 1232). The patient user provides a voice response to the conversational agent in response to confirm understanding of the titration instruction (Block 1234). Multi-turn interaction 1200 may comprise a decision block 1236 for driving the next turn in the multi-turn interaction based on the content of the user response from block 1234. If user response 1234 comprises a NO response (i.e., the patient user does not understand the titration instruction), then the conversational agent generates a knowledge base response based on the patient's issue (Block 1238) and multi-turn interaction 1200 proceeds to block 1232. If user response 1234 comprises a YES response (i.e., the patient user confirms understanding of the titration instruction), then the conversational agent proceeds by generating a generative voice output to provide check-in instructions for the next conversational interaction and concludes the interaction (Block 1240).

In accordance with certain aspects of the present disclosure, data from each turn of multi-turn interaction 1200 is stored in an application database (e.g., application database 122 of FIG. 1). The diabetes management application (e.g., diabetes management application 120 of FIG. 1) is configured to process the data to execute one or more operations; for example, provide a notification to the provider user that the patient's prescription has been titrated according to the clinical protocol.

An illustrative example of multi-turn interaction 1200 may be embodied as Conversation Flow 12-1, as shown below.

Conversation Flow 12-1

Patient user: "[wake word]"

Conversational agent: "Thanks for checking in. Did you take your dose of Lantus last night?"

Patient user: "Yes"

Conversational agent: "Great, how many units did you take?"

Patient user: "10 units"

Conversational agent: "Great, based on the blood sugars logged by your CGM, your doctor and I would like you to increase your dose of Lantus to 12 units every night. Do you understand?"

Patient user: "Yes"

Another illustrative example of multi-turn interaction 1200 may be embodied as Conversation Flow 12-2, as shown below.

Conversation Flow 12-2

Patient user: "[wake word]"

Conversational agent: "Have you missed any medication doses whatsoever since we last caught up eight days ago?"

Patient user: "No"

Conversational agent: "You have been doing a great job logging your medication and we do not need to check in as frequently. Keep taking 10 U of Glargine every night. Let's check back in again sometime next week. If a sooner visit is needed, I will let you know. Do you understand?"

Another illustrative example of multi-turn interaction 1200 may be embodied as Conversation Flow 12-3, as shown below.

Conversation Flow 12-3

Patient user: "[wake word]"

Conversational agent: "Have you missed any medication doses whatsoever since we last caught up eight days ago?"

Patient user: "Yes"

Conversational agent: "In the last nine days, how many times have you forgotten to take your medication?"

Patient user: "Four times"

Conversational agent: "It's ok, it can be tough to remember to take your medications sometimes. Please increase your dose of Glargine to 11 units every night remembering the best you can. [I will also provide extra reminders to help out]. Check back in with me tomorrow. Do you understand?"

Alternate: Conversational agent: "It's ok, it can be tough to remember to take your medications sometimes. Please continue taking 10 U Glargine every night remembering the best you can. [I will also provide extra reminders to help out]. Check back in with me tomorrow. Do you understand?"

Another illustrative example of multi-turn interaction 1200 may be embodied as Conversation Flow 12-4, as shown below.

Conversation Flow 12-4

Conversational agent: "Did you take all three doses of lispro yesterday?"

Patient user: "Yes"

Conversational agent: "Did you take the same dose for breakfast, lunch and dinner?"

Patient user: "Yes"

Conversational agent: "What dose did you take before each meal?"

Patient user: "Three units"

Conversational agent: "I'm logging that you took three units before breakfast, lunch and dinner, is that correct?"

Patient user: "Yes"

Conversational agent: "You have been doing a great job logging your medication and we do not need to check in as frequently. Let's check back in again sometime next week. If a sooner visit is needed, I will let you know."

Another illustrative example of multi-turn interaction 1200 may be embodied as Conversation Flow 12-5, as shown below.

Conversation Flow 12-5

Conversational agent: "Have you missed any medication doses whatsoever since we last caught up three days ago?"

Patient user: "No"

Conversational agent: "Great, keep taking 3 U of lispro before each meal. You're doing a great job! Let's catch up again next week. If a sooner visit is needed, I will let you know."

[Alternate]

Conversational agent: "Great, I want you to increase your lispro to 4 U before each meal. Check back in with me tomorrow."

Another illustrative example of multi-turn interaction 1200 may be embodied as Conversation Flow 12-6, as shown below.

Conversation Flow 12-6

Conversational agent: "Did you take all three doses of lispro yesterday?"

Patient user: "No"

Conversational agent: "Did you take your lispro with breakfast yesterday?"

Patient user: "No"

Conversational agent: "Did you take your lispro with lunch yesterday?"

Patient user: "No"

Conversational agent: "Did you take your lispro with dinner yesterday?"

Patient user: "Yes"

Conversational agent: "How many units did you take?"

Patient user: "Three units"

Conversational agent: "I'm logging that you took three units before dinner, is that correct?"

Patient user: "Yes"

Another illustrative example of multi-turn interaction 1200 may be embodied as Conversation Flow 12-7, as shown below.

Conversation Flow 12-7

Conversational agent: "Have you missed any doses of lispro whatsoever since we last caught up 9 days ago?"

Patient: "Yes"

Conversational agent: "In the last 9 days, about what percent of time have you been taking your lispro before meals?"

Patient user: "50%"

Conversational agent: "It's ok, it can be tough to remember to take your medications sometimes. Please continue taking 3 U lispro before each meal remembering the best you can. [I will also provide extra reminders to help out]. Check back in with me tomorrow."

Another illustrative example of multi-turn interaction 1200 may be embodied as Conversation Flow 12-8, as shown below.

Conversation Flow 12-8

Patient user: "[wake word]"

Conversational agent: "Have you missed any doses of your metformin immediate release over the last 5 days?"

Patient user: "No"

Conversational agent: "Do you think you are experiencing any side effects from your metformin immediate release? Side effects to look out for include diarrhea, nausea, stomach aches, body aches, and feeling sick."

Patient user: "No"

Conversational agent: "You're doing a great job logging in with me. Please continue 500 mg metformin immediate release every evening before bed. Do you understand?"

Patient user: "Yes"

Conversational agent: "Great, our next phase starts Monday, I'll remind you. Feel free to check in before then."

Another illustrative example of multi-turn interaction 1200 may be embodied as Conversation Flow 12-9, as shown below.

Conversation Flow 12-9

Conversational agent: "Today, we're going to make an adjustment to your metformin. Your doctor and I would like you to start taking 500 mg metformin immediate release twice a day. Once in the morning, and once at night. Do you understand?"

Patient user: "Yes"

Conversational agent: "Great! Do you have enough pills in your current bottle to start twice a day metformin immediate release today?"

Patient user: "Yes"

Conversational agent: "Great. Go ahead and start taking twice a day metformin immediate release. I will send an updated prescription to your pharmacy within a business day for you to pick up. Our next phase starts in 2 weeks. Feel free to check in before then."

Another illustrative example of multi-turn interaction 1200 may be embodied as Conversation Flow 12-10, as shown below.

Conversation Flow 12-10

Patient user: "[wake word]"

Conversational agent: "Hey! Have you picked up your new prescription for 500 mg metformin immediate release twice a day?"

Patient user: "Yes"

Conversational agent: "Have you started that prescription?"

Patient user: "Yes"

Conversational agent: "When did you start taking your new prescription?"

Patient user: "Today"

Conversational agent: "Great! Are you experiencing any new side effects?"

Patient user: "No"

Conversational agent: "Great, based on our treatment plan, you should continue metformin immediate release twice a day. Let's check back in two weeks when your next phase begins."

Figure 13:
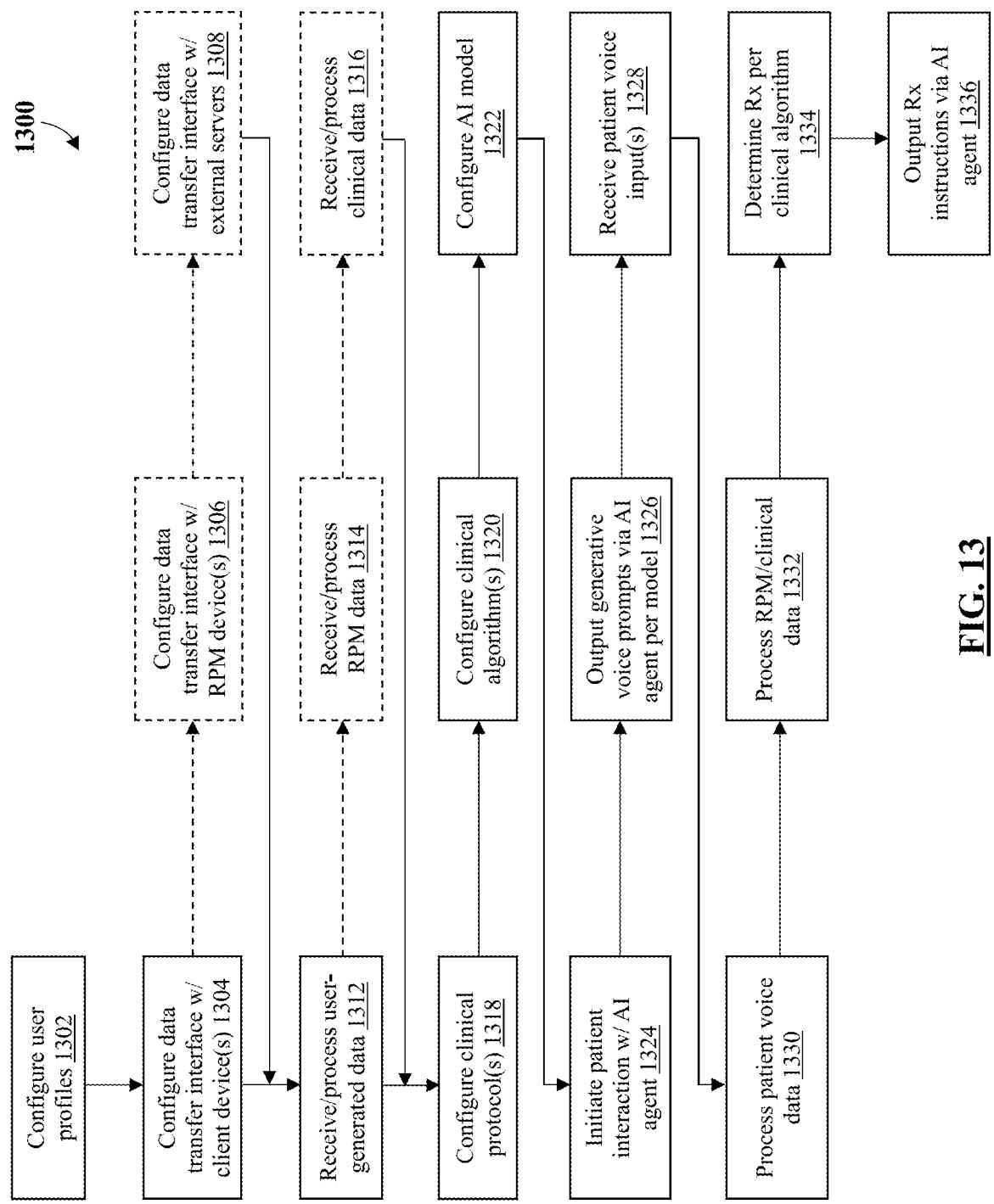
FIG. 13 is a process flow diagram of a process flow for a voice-based method for management of type 2 diabetes, in accordance with certain aspects of the present disclosure.

Referring now to FIG. 13, a process flow diagram of a voice-based method 1300 for management of type 2 diabetes is shown. In accordance with certain aspects of the present disclosure, method 1300 may be embodied as one or more functions or operations within system 100, as shown and described in FIG. 1, and/or system 300, as shown and described in FIG. 3. Method 1300 may comprise one or more steps or operations 1302-1336 for configuring one or more clinical protocols and algorithms for autonomous management and titration of at least one medication for management of type 2 diabetes in a patient user. The one or more steps or operations in method 1300 may be performed in the order presented, in a different order, or simultaneously. Further, in some exemplary embodiments, some of the operations may be omitted, added, modified, skipped, or the like without departing from the scope of the invention.

In accordance with certain aspects of the present disclosure, method 1300 may comprise one or more steps or operations for configuring one or more user profiles for a diabetes management application executing on an application server (Step 1302). The user profiles may include a patient user profile (e.g., associated with a patient with type 2 diabetes) and a practitioner user profile (e.g., associated with a primary care provider for the patient with type 2 diabetes). Method 1300 may comprise one or more steps or operations for configuring (e.g., with the application server) one or more data transfer interfaces between one or more client devices in a network (Step 1304). The client devices may include a smart speaker for the patient user, a patient user device (e.g., a smart phone) and a practitioner user device (e.g., a desktop workstation). In certain embodiments, method 1300 may comprise one or more steps or operations for configuring one or more data transfer interfaces with one or more remote patient monitoring (RPM) devices associated with the patient user (Step 1306). The RPM devices may include, for example, a CGM device, a wearable activity tracker, a blood pressure monitor, and the like. In certain embodiments, method 1300 may comprise one or more steps or operations for configuring one or more data transfer interfaces (e.g., APIs) with one or more external servers (Step 1308). The external servers may include, for example, an EMR/EHR server, a LIMS server, a payor server, and the like. In accordance with certain aspects of the present disclosure, method 1300 may comprise one or more steps or operations for receiving and processing a plurality of user generated data (Step 1312). The plurality of user generated data may include a plurality of inputs via a practitioner user interface for configuring one or more clinical protocols for management of type 2 diabetes for the patient user (e.g., pursuant to routine 400, as shown in FIG. 4). In certain embodiments, method 1300 may comprise one or more steps or operations for receiving and processing one or more data inputs from the one or more RPM devices (Step 1314). For example, the application server may receive one or more sets of blood glucose data for the patient via the CGM device. In certain embodiments, method 1300 may comprise one or more steps or operations for receiving and processing one or more sets of clinical data for the patient; e.g., via the external servers (Step 1316). The clinical data may comprise laboratory test results, electronic medical records, and the like.

In accordance with certain aspects of the present disclosure, method 1300 may comprise one or more steps or operations for configuring one or more clinical protocols for the patient user via the diabetes management application at the application server (Step 1318). The one or more clinical protocols may comprise protocols for managing the treatment of type 2 diabetes in the patient user according to the practitioner user's configurations, the RPM data and the clinical data. Method 1300 may further comprise one or more steps or operations for configuring (e.g., via the diabetes management application at the application server) one or more clinical algorithms for initiation, titration and termination of one or more medications for treatment of type 2 diabetes in the patient user in accordance with the clinical protocol(s) (Step 1320). Method 1300 may further comprise one or more steps or operations for configuring a conversational AI model via a conversational AI engine executing on the application server (Step 1322). In certain embodiments, the conversational AI engine is configured to analyze one or more variables or objects of the one or more clinical algorithms to configure the conversational AI model.

In accordance with certain aspects of the present disclosure, method 1300 may comprise one or more steps or operations for initiating an interaction between a conversational agent and the patient user (Step 1324). In accordance with certain embodiments, the conversational agent is instantiated via a smart speaker present in the patient user's home or other non-clinical setting. In certain embodiments, step 1324 is instantiated in response to the patient user speaking a wake word utterance to the smart speaker. Method 1300 may further comprise one or more steps or operations for generating one or more prompts via the conversational agent and outputting the prompts as computer voice outputs at the smart speaker (Step 1326) and receiving one or more patient voice inputs at the smart speaker in response to the prompts (Step 1328). In accordance with certain embodiments, steps 1326-1328 may be embodied as one or more multi-turn conversational interactions between the patient user and the conversational agent; for example, as shown and described in FIGS. 10-12. Method 1300 may further comprise one or more steps or operations for processing the voice data received pursuant to step 1328 at the application server; e.g., according to the clinical algorithm(s)/protocol(s) (Step 1330). In certain embodiments, method 1300 may further comprise one or more steps or operations for processing the RPM data (e.g., CGM data) and/or clinical data (e.g., lab test results) either concomitantly or independently with the voice data (Step 1332). In accordance with certain aspects of the present disclosure, method 1300 may comprise one or more steps or operations for determining at least one prescription for the patient user (Step 1334) and outputting a generative prompt as a computer voice output at the smart speaker to the patient user, wherein the generative prompt comprises dosage instructions for the prescription for the patient user (Step 1336).

Figure 14:
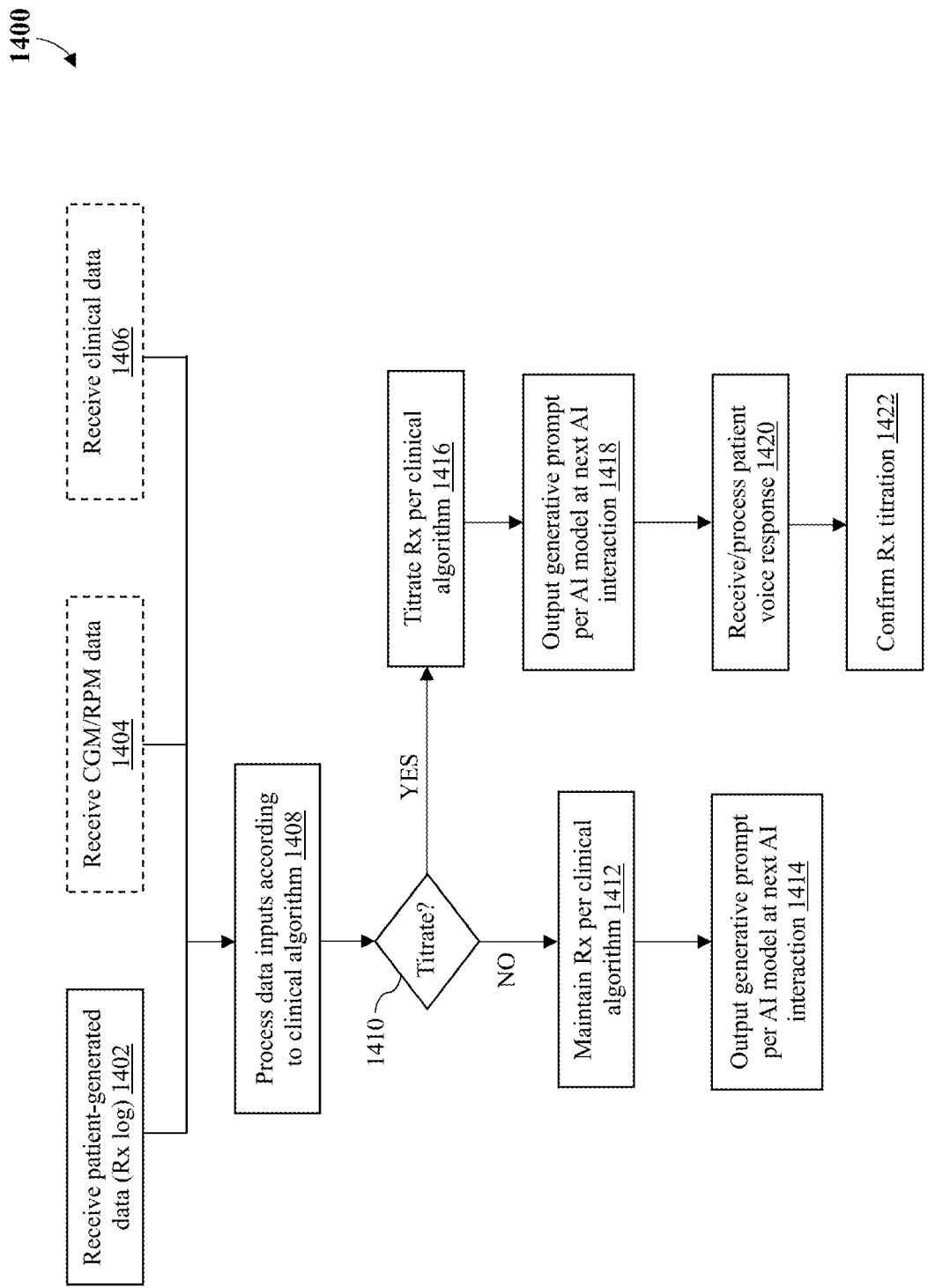
FIG. 14 is a process flow diagram of a process flow for a voice-based method for management of type 2 diabetes, in accordance with certain aspects of the present disclosure.

Referring now to FIG. 14, a process flow diagram of a voice-based method 1400 for management of type 2 diabetes is shown. In accordance with certain aspects of the present disclosure, method 1400 may be embodied as one or more functions or operations within system 100, as shown and described in FIG. 1, and/or system 300, as shown and described in FIG. 3. Method 1400 may be successive or sequential to one or more steps or operations of method 1300, as shown and described in FIG. 13. Method 1400 may comprise one or more steps or operations 1402-1422 for autonomous management and titration of at least one medication for management of type 2 diabetes in a patient user. The one or more steps or operations in method 1400 may be performed in the order presented, in a different order, or simultaneously. Further, in some exemplary embodiments, some of the operations may be omitted, added, modified, skipped, or the like without departing from the scope of the invention.

In accordance with certain aspects of the present disclosure, method 1400 may comprise one or more steps or operations for receiving one or more patient-generated inputs associated with management of type 2 diabetes in the patient user (Step 1402). In certain embodiments, the patient-generated inputs comprise one or more voice inputs at the smart speaker in response to at least one conversational interaction with the conversational agent. The patient-generated inputs may comprise medication log data (e.g., how much medication the patient user took and when) as well as patient health data, such as blood glucose data, side effect data, questionnaire response data, and patient-reported general well-being data. Method 1400 may further comprise one or more steps or operations for receiving (e.g., at the application server) CGM data and/or RPM data for the patient user from the CGM device and/or other RPM devices (Step 1404) and/or clinical data from the patient user via an external server or a client device (Step 1406). Method 1400 may comprise one or more steps or operations for processing one or more of the patient-generated data, the CGM data, the RPM data and/or the clinical data according to the clinical algorithm at the application server (Step 1408). In accordance with certain aspects of the present disclosure, method 1400 may comprise one or more steps or operations for determining whether to titrate one or more prescribed medication for the patient user according to the clinical algorithm (Step 1410). If YES, then the diabetes management application titrates the prescribed medication for the patient user according to the clinical algorithm and updates the dosage instructions for the prescribed medication per the titration in the application database (Step 1416). Method 1400 may proceed by executing one or more steps or operations for outputting a generative prompt as a computer voice output at the smart speaker to the patient user at the next conversational interaction, wherein the generative prompt comprises instructions for titrating the prescribed medication and a prompt to confirm the patient user's understanding/consent to the titrated dosage instructions (Step 1418). Method 1400 may comprise one or more steps or operations for receiving and processing at least one voice response from the patient user via the smart speaker (Step 1420) and confirming the titrated dosage instructions for the patient user in response to the at least one voice response (Step 1422). If the output of step 1410 is NO, then the diabetes management application maintains the current dosage instructions for the prescribed medication in the application database (Step 1412). Method 1400 may proceed by executing one or more steps or operations for outputting a generative prompt as a computer voice output at the smart speaker to the patient user at the next conversational interaction, wherein the generative prompt comprises instructions for maintaining the current dosage instructions for the prescribed medication (Step 1414). In accordance with certain embodiments, one or more of steps 1402-1422 may be embodied as one or more multi-turn conversational interactions between the patient user and the conversational agent; for example, as shown and described in FIGS. 10-12.

Figure 15:
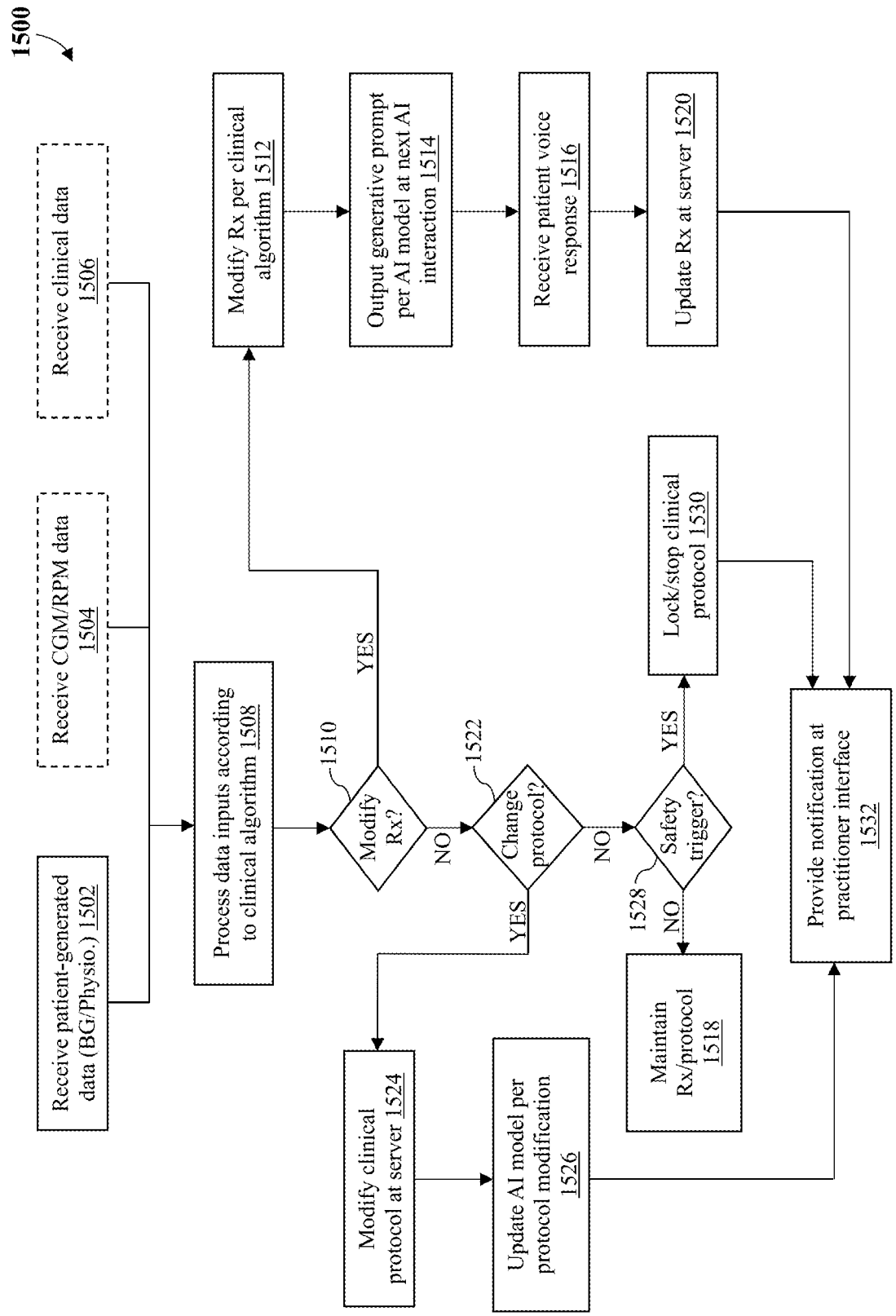
FIG. 15 is a process flow diagram of a process flow for a voice-based method for management of type 2 diabetes, in accordance with certain aspects of the present disclosure.

Referring now to FIG. 15, a process flow diagram of a voice-based method 1500 for management of type 2 diabetes is shown. In accordance with certain aspects of the present disclosure, method 1500 may be embodied as one or more functions or operations within system 100, as shown and described in FIG. 1, and/or system 300, as shown and described in FIG. 3. Method 1500 may be successive or sequential to one or more steps or operations of method 1300, as shown and described in FIG. 13, and/or method 1400, as shown and described in FIG. 14. Method 1500 may comprise one or more steps or operations 1502-1532 for modifying or discontinuing one or more clinical protocol for autonomous management and titration of at least one medication for management of type 2 diabetes in a patient user. The one or more steps or operations in method 1500 may be performed in the order presented, in a different order, or simultaneously. Further, in some exemplary embodiments, some of the operations may be omitted, added, modified, skipped, or the like without departing from the scope of the invention.

In accordance with certain aspects of the present disclosure, method 1500 may comprise one or more steps or operations for receiving at least one patient-generated dataset associated with management of type 2 diabetes in the patient user (Step 1502). In certain embodiments, the at least one patient-generated dataset may comprise one or more voice inputs at the smart speaker in response to at least one conversational interaction with the conversational agent. The at least one patient-generated dataset may comprise medication log data (e.g., how much medication the patient user took and when). The at least one patient-generated dataset may comprise physiological data such as blood glucose data, blood pressure data, EKG data, lab results, and the like. The patient-generated inputs may also comprise patient health data, side effect data, lab results, questionnaire response data, and general well-being data. Method 1500 may further comprise one or more steps or operations for receiving (e.g., at the application server) CGM data and/or RPM data for the patient user via the CGM device and/or other RPM devices (Step 1504) and/or clinical data from the patient user via an external server or a client device (Step 1506). Method 1500 may comprise one or more steps or operations for processing one or more of the patient-generated data, the CGM data, the RPM data and/or the clinical data according to the clinical algorithm at the application server (Step 1508). In accordance with certain aspects of the present disclosure, method 1500 may comprise one or more steps or operations for determining whether to modify at least one prescription for the patient user according to the clinical algorithm (Step 1510). If YES, then the diabetes management application modifies the prescription for the patient user according to the clinical algorithm and updates the prescription in the application database (Step 1512). Method 1500 may proceed by executing one or more steps or operations for outputting a generative prompt as a computer voice output at the smart speaker to the patient user at the next conversational interaction, wherein the generative prompt comprises instructions for modifying a prescribed medication and a prompt to confirm the patient user's understanding/consent to the modified prescription (Step 1514). Method 1500 may comprise one or more steps or operations for receiving and processing at least one voice response from the patient user via the smart speaker (Step 1516) and confirming the patient user's understanding/consent to the modified prescription in response to the at least one voice response (Step 1520). If the output of step 1510 is NO, then method 1500 may proceed by executing one or more steps or operations for determining whether to change the clinical protocol for the patient user according to one or more clinical parameters (Step 1522). For example, the clinical protocol may be updated in response to the patient starting a new medication; e.g., transitioning from a prescription for metformin only to a prescription for metformin and another glycemic medication, such as semaglutide. If YES, method 1500 comprises one or more steps or operations for modifying or updating the clinical protocol for the patient user within the diabetes management application/database (Step 1524) and updating the conversational AI model via the conversational AI engine per the protocol modification (Step 1526). In accordance with certain aspects of the present disclosure, method 1500 may comprise one or more steps or operations for communicating a notification of the modification to the clinical protocol at a practitioner user interface of the diabetes management application (Step 1532).

In accordance with certain aspects of the present disclosure, if the output of step 1522 is NO (i.e., the clinical protocol is not changed/modified), then method 1500 may proceed by executing one or more steps or operations for determining whether one or more of the at least one patient-generated dataset, the CGM/RPM data and/or the clinical data exceeds at least one threshold value for at least one safety trigger according to the clinical protocol (Step 1528). In accordance with certain embodiments, the at least one safety trigger may comprise at least one condition under which continuing the clinical protocol may be unsafe for the patient. For example, the patient has experienced successive hypoglycemic events, the patient's blood pressure is in excess of a threshold value, or the patient has started another medication that is contraindicated with at least one of the medications under the current protocol. If YES, method 1500 may comprise one or more steps or operations for locking or stopping the clinical protocol per the diabetes management application (Step 1530) and communicating a notification to the practitioner user interface of the diabetes management application to inform the practitioner user that the clinical protocol has been locked/stopped and the reasons therefor (Step 1532).

Figure 16:
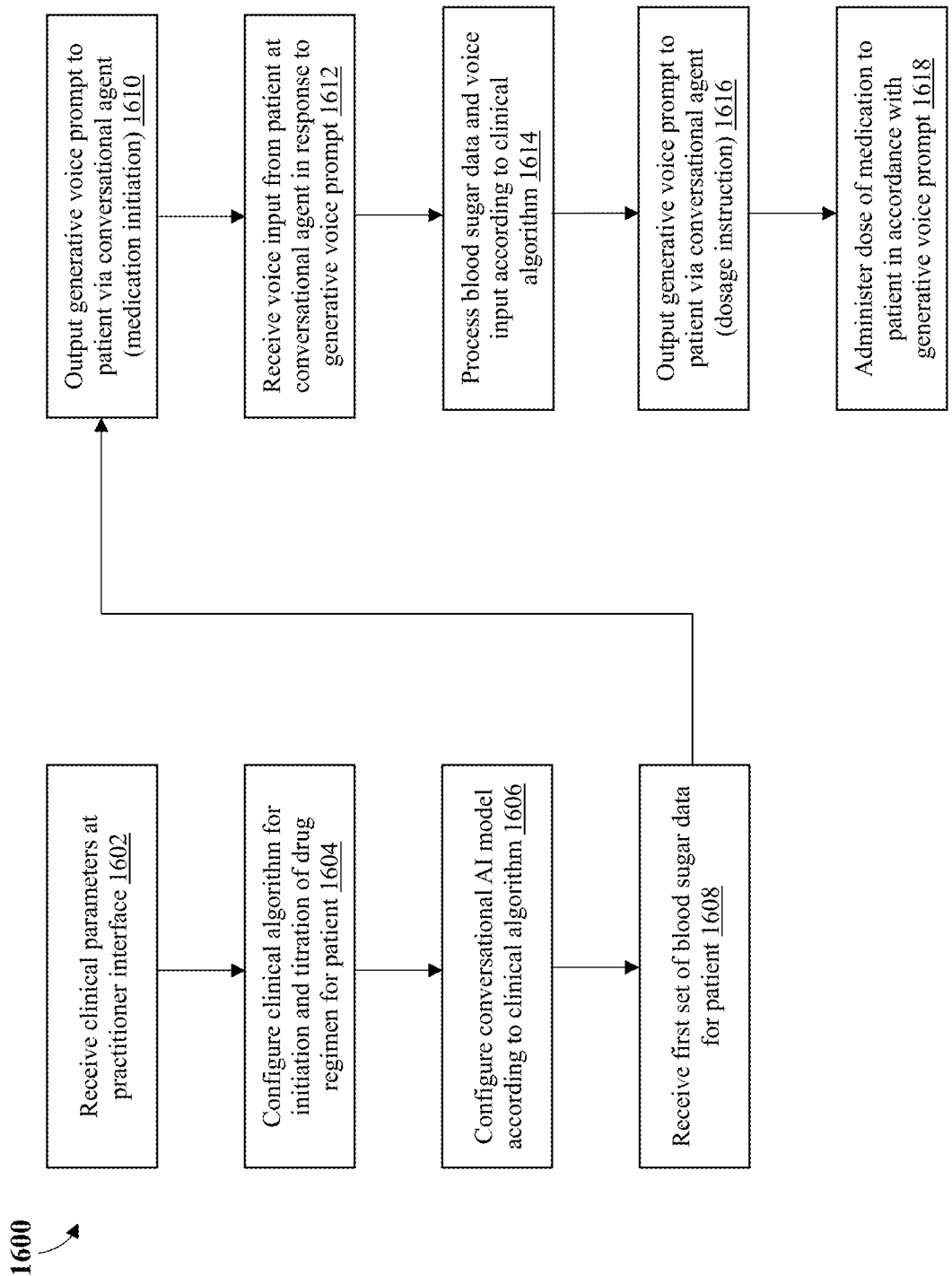
FIG. 16 is a process flow diagram of a voice-based method for management of type 2 diabetes, in accordance with certain aspects of the present disclosure.

Referring now to FIG. 16, a process flow diagram of a voice-based method 1600 for management of type 2 diabetes is shown. In accordance with certain aspects of the present disclosure, method 1600 may be embodied as one or more functions or operations within system 100, as shown and described in FIG. 1, and/or system 300, as shown and described in FIG. 3. Method 1600 may comprise one or more steps or operations 1602-1618 for an artificially intelligent, voice-based method for prescribing, managing and administering at least one medication for management of type 2 diabetes (e.g., an SGLT-2 inhibitor drug and/or a GLP-1 agonist drug and/or a biguanide drug) to a patient. The one or more steps or operations in method 1600 may be performed in the order presented, in a different order, or simultaneously. Further, in some exemplary embodiments, some of the operations may be omitted, added, modified, skipped, or the like without departing from the scope of the invention.

In accordance with certain aspects of the present disclosure provide, method 1600 may comprise one or more steps or operations for receiving (e.g., from a practitioner user via a first client device) a plurality of user-generated inputs comprising a plurality of clinical parameters for management of type 2 diabetes in a patient (Step 1602). The plurality of user-generated inputs may comprise one or more inputs at a graphical user interface of a practitioner instance of a diabetes management application (e.g., as shown in FIG. 5). Method 1600 may proceed by executing one or more steps or operations for configuring (e.g., with at least one server communicably engaged with the first client device) a clinical algorithm for initiation and titration of a diabetes drug regimen for the patient according to the plurality of user-generated inputs (Step 1604). In accordance with various aspects of the present disclosure, the diabetes drug may comprise one or more GLP-1 agonist drug and/or biguanide drug and/or SGLT-2 inhibitor drug. Method 1600 may proceed by executing one or more steps or operations for configuring (e.g., with the at least one server) a conversational AI model according to the clinical algorithm (Step 1606). Method 1600 may proceed by executing one or more steps or operations for receiving (e.g., with the at least one server) a first set of blood sugar data or hemoglobin A1C data for the patient (e.g., via at least one continuous blood glucose monitoring device or glucometer) (Step 1608). Method 1600 may proceed by executing one or more steps or operations for outputting (e.g., with a conversational agent) a first generative voice prompt to the patient according to the conversational AI model (Step 1610). In accordance with certain embodiments, the conversational agent comprises a smart speaker communicably engaged with at least one server via a network interface. In accordance with certain embodiments, the first generative voice prompt comprises a medication initiation prompt for at least one medication for management of type 2 diabetes for the patient. In certain embodiments, the at least one medication comprises one or more GLP-1 agonist drug, biguanide drug and/or SGLT-2 inhibitor drug. Method 1600 may proceed by executing one or more steps or operations for receiving (e.g., with the conversational agent) a first voice input from the patient in response to the first generative voice prompt (Step 1612). In accordance with certain embodiments, the first voice input comprises a response to the medication initiation prompt by the patient (i.e., confirmation of the prescription by the patient). Method 1600 may proceed by executing one or more steps or operations for processing (e.g., with the at least one server) the first set of blood sugar data or hemoglobin A1C data and the first voice input according to the clinical algorithm (Step 1614). Method 1600 may proceed by executing one or more steps or operations for outputting (e.g., with the conversational agent) a second generative voice prompt according to the conversational AI model (Step 1616). In certain embodiments, the second generative voice prompt comprises a first dosage instruction for the diabetes drug regimen for the patient according to the clinical algorithm. In accordance with certain aspects of the present disclosure, method 1600 may conclude upon the patient administering a first dose of the diabetes drug to himself or herself in accordance with the first dosage instruction (Step 1618).

In accordance with certain aspects of the present disclosure, method 1600 may further comprise one or more steps or operations for establishing a data transfer interface between a continuous glucose monitor device or glucometer for the patient and the at least one server. In certain embodiments, the first set of blood sugar data or hemoglobin A1C data for the patient comprises data collected via the continuous glucose monitor device or glucometer. In accordance with certain aspects of the present disclosure, method 1600 may further comprise one or more steps or operations for outputting (e.g., with the conversational agent) a third generative voice prompt according to the conversational AI model, wherein the third generative voice prompt comprises a medication log prompt for the diabetes drug regimen; receiving (e.g., with the conversational agent) a second voice input from the patient in response to the third generative voice prompt, wherein the second voice input comprises medication log data for the patient; and recording (e.g., with the at least one server) the medication log data for the patient according to the second voice input. In accordance with certain aspects of the present disclosure, method 1600 may further comprise one or more steps or operations for receiving (e.g., with the at least one server) a second set of blood sugar data or hemoglobin A1C data for the patient; and analyzing (e.g., with the at least one server) the second set of blood sugar data or hemoglobin A1C data and the medication log data for the patient according to the clinical algorithm. In accordance with certain aspects of the present disclosure, method 1600 may further comprise one or more steps or operations for outputting (e.g., with the conversational agent) a fourth generative voice prompt according to the conversational AI model, wherein the fourth generative voice prompt comprises a second medication dosage instruction for the diabetes drug regimen for the patient according to the clinical algorithm; and administering, by the patient, a second dose of medication to the patient in accordance with the second medication dosage instruction. In accordance with certain aspects of the present disclosure, method 1600 may further comprise one or more steps or operations for outputting (e.g., with the conversational agent) a fifth generative voice prompt according to the conversational AI model, wherein the fifth generative voice prompt comprises a check-in prompt for the patient; receiving (e.g., with the conversational agent) a third voice input from the patient in response to the fifth generative voice prompt, wherein the third voice input comprises a response to the check-in prompt; and recording (e.g., with the at least one server) response data for the patient according to the third voice input.

Figure 17:
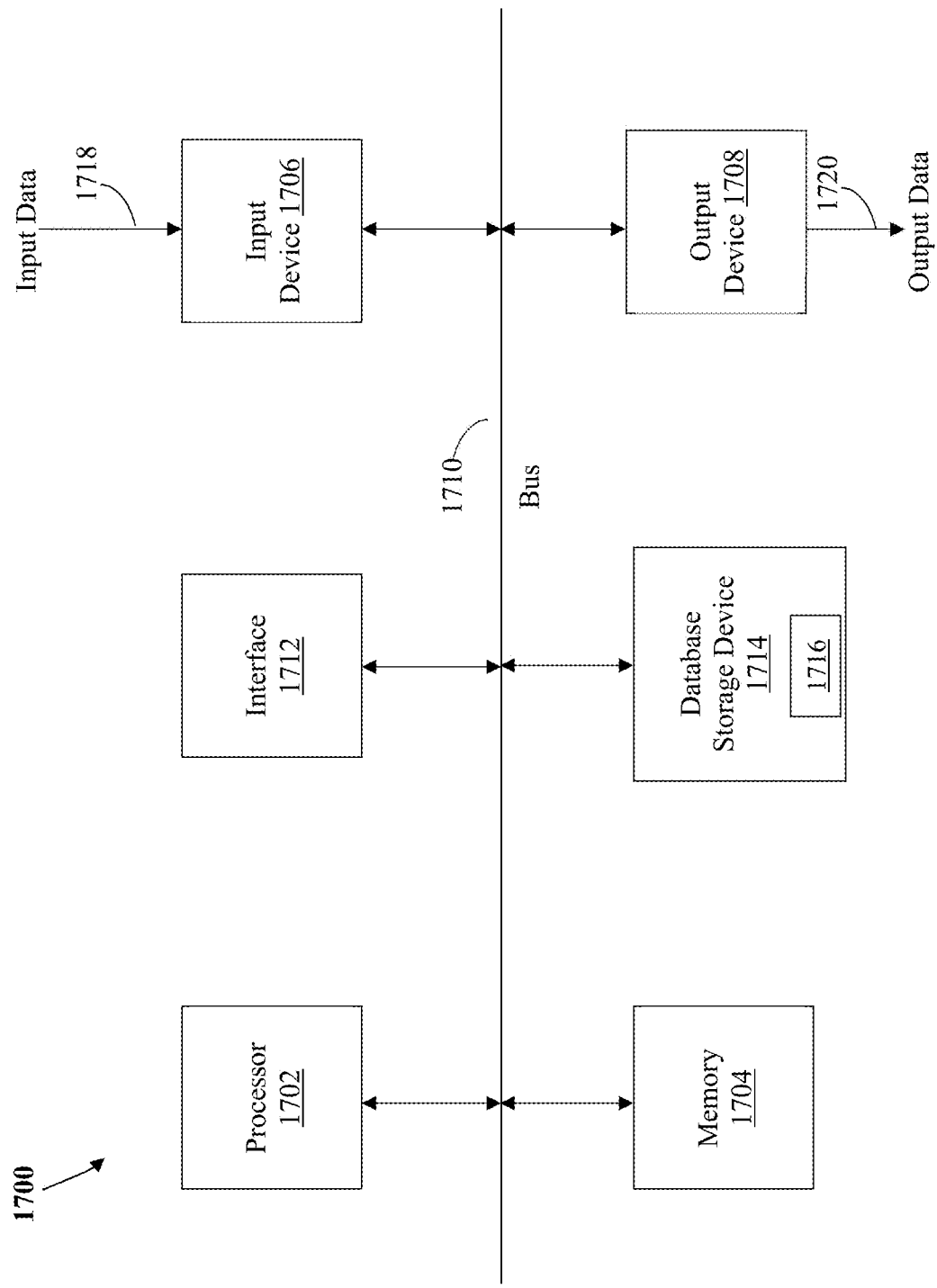
FIG. 17 is a functional diagram of an exemplary computing system through which one or more aspects of the present disclosure may be implemented.

Referring now to FIG. 17, a processor-implemented computing device in which one or more aspects of the present disclosure may be implemented is shown. According to an embodiment, a processing system 1700 may generally comprise at least one processor 1702, or processing unit or plurality of processors, memory 1704, at least one input device 1706 and at least one output device 1708, coupled together via a bus or group of buses 1710. In certain embodiments, input device 1706 and output device 1708 could be the same device. An interface 1712 can also be provided for coupling the processing system 1700 to one or more peripheral devices, for example interface 1712 could be a PCI card or PC card. At least one storage device 1714 which houses at least one database 1716 can also be provided. The memory 1704 can be any form of memory device, for example, volatile or non-volatile memory, solid state storage devices, magnetic devices, etc. The processor 1702 could comprise more than one distinct processing device, for example to handle different functions within the processing system 1700. Input device 1706 receives input data 1718 and can comprise, for example, a keyboard, a pointer device such as a pen-like device or a mouse, audio receiving device for voice-controlled activation such as a microphone, data receiver or antenna such as a modem or wireless data adaptor, data acquisition card, etc. Input data 1718 could come from different sources, for example keyboard instructions in conjunction with data received via a network. Output device 1708 produces or generates output data 1720 and can comprise, for example, a display device or monitor in which case output data 1720 is visual, a printer in which case output data 1720 is printed, a port for example a USB port, a peripheral component adaptor, a data transmitter or antenna such as a modem or wireless network adaptor, etc. Output data 1720 could be distinct and derived from different output devices, for example a visual display on a monitor in conjunction with data transmitted to a network. A user could view data output, or an interpretation of the data output, on, for example, a monitor or using a printer. The storage device 1714 can be any form of data or information storage means, for example, volatile or non-volatile memory, solid state storage devices, magnetic devices, etc.

In use, the processing system 1700 is adapted to allow data or information to be stored in and/or retrieved from, via wired or wireless communication means, at least one database 1716. The interface 1712 may allow wired and/or wireless communication between the processing unit 1702 and peripheral components that may serve a specialized purpose. In general, the processor 1702 can receive instructions as input data 1718 via input device 1706 and can display processed results or other output to a user by utilizing output device 1708. More than one input device 1706 and/or output device 1708 can be provided. It should be appreciated that the processing system 1700 may be any form of terminal, server, specialized hardware, or the like.

It is to be appreciated that the processing system 1700 may be a part of a networked communications system. Processing system 1700 could connect to a network, for example the Internet or a WAN. Input data 1718 and output data 1720 could be communicated to other devices via the network. The transfer of information and/or data over the network can be achieved using wired communications means or wireless communications means. A server can facilitate the transfer of data between the network and one or more databases. A server and one or more databases provide an example of an information source. Thus, the processing computing system environment 1700 illustrated in FIG. 17 may operate in a networked environment using logical connections to one or more remote computers. The remote computer may be a personal computer, a server, a router, a network PC, a peer device, or other common network node, and typically includes many or all of the elements described above.

It is to be further appreciated that the logical connections depicted in FIG. 17 include a local area network (LAN) and a wide area network (WAN) but may also include other networks such as a personal area network (PAN). Such networking environments are commonplace in offices, enterprise-wide computer networks, intranets, and the Internet. For instance, when used in a LAN networking environment, the computing system environment 1700 is connected to the LAN through a network interface or adapter. When used in a WAN networking environment, the computing system environment typically includes a modem or other means for establishing communications over the WAN, such as the Internet. The modem, which may be internal or external, may be connected to a system bus via a user input interface, or via another appropriate mechanism. In a networked environment, program modules depicted relative to the computing system environment 1700, or portions thereof, may be stored in a remote memory storage device. It is to be appreciated that the illustrated network connections of FIG. 17 are exemplary and other means of establishing a communications link between multiple computers may be used.

FIG. 17 is intended to provide a brief, general description of an illustrative and/or suitable exemplary environment in which embodiments of the below described present invention may be implemented. FIG. 17 is an example of a suitable environment and is not intended to suggest any limitation as to the structure, scope of use, or functionality of an embodiment of the present invention. A particular environment should not be interpreted as having any dependency or requirement relating to any one or combination of components illustrated in an exemplary operating environment. For example, in certain instances, one or more elements of an environment may be deemed not necessary and omitted. In other instances, one or more other elements may be deemed necessary and added.

In the foregoing description, certain embodiments have been described with reference to acts and symbolic representations of operations that are performed by one or more computing devices, such as the computing system environment 1700 of FIG. 17. As such, it will be understood that such acts and operations, which are at times referred to as being computer-executed, include the manipulation by the processor of the computer of electrical signals representing data in a structured form. This manipulation transforms the data or maintains them at locations in the memory system of the computer, which reconfigures or otherwise alters the operation of the computer in a manner understood by those skilled in the art. The data structures in which data is maintained are physical locations of the memory that have particular properties defined by the format of the data. However, while an embodiment is being described in the foregoing context, it is not meant to be limiting as those of skill in the art will appreciate that the acts and operations described hereinafter may also be implemented in hardware.

Embodiments may be implemented with numerous other general-purpose or special-purpose computing devices and computing system environments or configurations. Examples of well-known computing systems, environments, and configurations that may be suitable for use with an embodiment include, but are not limited to, personal computers, handheld or laptop devices, personal digital assistants, multiprocessor systems, microprocessor-based systems, set top boxes, programmable consumer electronics, network, minicomputers, server computers, game server computers, web server computers, mainframe computers, and distributed computing environments that include any of the above systems or devices.

Embodiments may be described in a general context of computer-executable instructions, such as program modules, being executed by a computer. Generally, program modules include routines, programs, objects, components, data structures, etc., that perform particular tasks or implement particular abstract data types. An embodiment may also be practiced in a distributed computing environment where tasks are performed by remote processing devices that are linked through a communications network. In a distributed computing environment, program modules may be located in both local and remote computer storage media including memory storage devices.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, exemplary methods and materials are now described. All publications mentioned herein are incorporated herein by reference to disclose and describe the methods and/or materials in connection with which the publications are cited.

It must be noted that as used herein and in the appended claims, the singular forms "a", "an," and "the" include plural referents unless the context clearly dictates otherwise. Thus, for example, reference to "a stimulus" includes a plurality of such stimuli and reference to "the signal" includes reference to one or more signals and equivalents thereof known to those skilled in the art, and so forth.

Any publications discussed herein are provided solely for their disclosure prior to the filing date of the present application. Nothing herein is to be construed as an admission that the present invention is not entitled to antedate such publication by virtue of prior invention. Further, the dates of publication provided may differ from the actual publication dates which may need to be independently confirmed.

As will be appreciated by one of skill in the art, the present invention may be embodied as a method (including, for example, a computer-implemented process, a business process, and/or any other process), apparatus (including, for example, a system, machine, device, computer program product, and/or the like), or a combination of the foregoing. Accordingly, embodiments of the present invention may take the form of an entirely hardware embodiment, an entirely software embodiment (including firmware, resident software, micro-code, etc.), or an embodiment combining software and hardware aspects that may generally be referred to herein as a "system." Furthermore, embodiments of the present invention may take the form of a computer program product on a computer-readable medium having computer-executable program code embodied in the medium.

Any suitable transitory or non-transitory computer readable medium may be utilized. The computer readable medium may be, for example but not limited to, an electronic, magnetic, optical, electromagnetic, infrared, or semiconductor system, apparatus, or device. More specific examples of the computer readable medium include, but are not limited to, the following: an electrical connection having one or more wires; a tangible storage medium such as a portable computer diskette, a hard disk, a random-access memory (RAM), a read-only memory (ROM), an erasable programmable read-only memory (EPROM or Flash memory), a compact disc read-only memory (CD-ROM), or other optical or magnetic storage device.

In the context of this document, a computer readable medium may be any medium that can contain, store, communicate, or transport the program for use by or in connection with the instruction execution system, apparatus, or device. The computer usable program code may be transmitted using any appropriate medium, including but not limited to the Internet, wireline, optical fiber cable, radio frequency (RF) signals, or other mediums.

Computer-executable program code for carrying out operations of embodiments of the present invention may be written in an object oriented, scripted or unscripted programming language such as Java, Perl, Smalltalk, C++, or the like. However, the computer program code for carrying out operations of embodiments of the present invention may also be written in conventional procedural programming languages, such as the "C" programming language or similar programming languages.

Embodiments of the present invention are described above with reference to flowchart illustrations and/or block diagrams of methods, apparatus (systems), and computer program products. It will be understood that each block of the flowchart illustrations and/or block diagrams, and/or combinations of blocks in the flowchart illustrations and/or block diagrams, can be implemented by computer-executable program code portions. These computer-executable program code portions may be provided to a processor of a general-purpose computer, special purpose computer, or other programmable data processing apparatus to produce a particular machine, such that the code portions, which execute via the processor of the computer or other programmable data processing apparatus, create mechanisms for implementing the functions/acts specified in the flowchart and/or block diagram block or blocks.

These computer-executable program code portions may also be stored in a computer-readable memory that can direct a computer or other programmable data processing apparatus to function in a particular manner, such that the code portions stored in the computer readable memory produce an article of manufacture including instruction mechanisms which implement the function/act specified in the flowchart and/or block diagram block(s).

The computer-executable program code may also be loaded onto a computer or other programmable data processing apparatus to cause a series of operational phases to be performed on the computer or other programmable apparatus to produce a computer-implemented process such that the code portions which execute on the computer or other programmable apparatus provide phases for implementing the functions/acts specified in the flowchart and/or block diagram block(s). Alternatively, computer program implemented phases or acts may be combined with operator or human implemented phases or acts in order to carry out an embodiment of the invention.

As the phrase is used herein, a processor may be "configured to" perform a certain function in a variety of ways, including, for example, by having one or more general-purpose circuits perform the function by executing particular computer-executable program code embodied in computer-readable medium, and/or by having one or more application-specific circuits perform the function.

Embodiments of the present invention are described above with reference to flowcharts and/or block diagrams. It will be understood that phases of the processes described herein may be performed in orders different than those illustrated in the flowcharts. In other words, the processes represented by the blocks of a flowchart may, in some embodiments, be performed in an order other than the order illustrated, may be combined or divided, or may be performed simultaneously. It will also be understood that the blocks of the block diagrams illustrate, in some embodiments, merely conceptual delineations between systems and one or more of the systems illustrated by a block in the block diagrams may be combined or share hardware and/or software with another one or more of the systems illustrated by a block in the block diagrams. Likewise, a device, system, apparatus, and/or the like may be made up of one or more devices, systems, apparatuses, and/or the like. For example, where a processor is illustrated or described herein, the processor may be made up of a plurality of microprocessors or other processing devices which may or may not be coupled to one another. Likewise, where a memory is illustrated or described herein, the memory may be made up of a plurality of memory devices which may or may not be coupled to one another.

In the claims, as well as in the specification above, all transitional phrases such as "comprising," "including," "carrying," "having," "containing," "involving," "holding," "composed of," and the like are to be understood as open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

While certain exemplary embodiments have been described and shown in the accompanying drawings, it is to be understood that such embodiments are merely illustrative of, and not restrictive on, the broad invention, and that this invention is not limited to the specific constructions and arrangements shown and described, since various other changes, combinations, omissions, modifications and substitutions, in addition to those set forth in the above paragraphs, are possible. Those skilled in the art will appreciate that various adaptations and modifications of the just described embodiments can be configured without departing from the scope and spirit of the invention. Therefore, it is to be understood that, within the scope of the appended claims, the invention may be practiced other than as specifically described herein.

What is claimed is:

1. A method for management of type 2 diabetes comprising:
   receiving, from a practitioner user via a first client device, a plurality of user-generated inputs comprising a plurality of clinical parameters for management of type 2 diabetes in a patient,
   wherein the plurality of clinical parameters comprise at least one dosage amount and at least one dosage frequency for a glucagon-like peptide 1 (GLP-1) agonist drug in a GLP-1 agonist drug regimen,
   wherein the plurality of clinical parameters comprise at least one blood sugar or hemoglobin A1C range for the patient;
   configuring, with at least one server communicably engaged with the first client device, a clinical algorithm for the GLP-1 agonist drug regimen for the patient according to the plurality of user-generated inputs,
   wherein the clinical algorithm comprises parameters for titrating the at least one dosage amount and modifying the at least one dosage frequency for the GLP-1 agonist drug in the GLP-1 agonist drug regimen according to the at least one blood sugar or hemoglobin A1C range for the patient;

configuring, with the at least one server, a conversational AI model according to the clinical algorithm, wherein the conversational AI model comprises a large language model configured to drive a plurality of generative text-to-speech outputs of a conversational agent;

receiving, with the at least one server, a first set of blood sugar or hemoglobin A1C data for the patient;

outputting, with the conversational agent, a first generative voice prompt to the patient according to the conversational AI model, wherein the first generative voice prompt comprises a medication log prompt for the GLP-1 agonist drug regimen, wherein the conversational agent comprises a smart speaker communicably engaged with the at least one server via a network interface;

receiving, with the conversational agent, a first voice input from the patient in response to the first generative voice prompt, wherein the first voice input comprises a first set of medication log data for the GLP-1 agonist drug for the patient;

processing, with the at least one server, the first set of medication log data for the GLP-1 agonist drug for the patient and the first set of blood sugar or hemoglobin A1C data for the patient according to the clinical algorithm;

titrating the dosage amount and/or modifying the dosage frequency of the GLP-1 agonist drug for the patient in response to processing the first set of medication log data for the GLP-1 agonist drug for the patient and the first set of blood sugar or hemoglobin A1C data according to the clinical algorithm;

configuring, with the at least one server, a second generative voice prompt according to the conversational AI model, wherein the second generative voice prompt comprises a dosage instruction for the GLP-1 agonist drug regimen for the patient, wherein the dosage instruction comprises the titrated dosage amount and/or the modified dosage frequency for the GLP-1 agonist drug according to the clinical algorithm;

outputting, with the conversational agent, the second generative voice prompt to the patient; and administering, by the patient, a dose of the GLP-1 agonist drug to the patient in accordance with the dosage instruction provided by the second generative voice prompt.

2. The method according to claim 1 further comprising establishing a data transfer interface between a continuous glucose monitor device or a glucometer for the patient and the at least one server.

3. The method according to claim 2 further comprising receiving, with the at least one server, the first set of blood sugar or hemoglobin A1C data for the patient via the continuous glucose monitor device or the glucometer.

4. The method according to claim 1 further comprising:
outputting, with the conversational agent, a third generative voice prompt according to the conversational AI model, wherein the third generative voice prompt comprises a medication log prompt for the GLP-1 agonist drug regimen for a subsequent specified time period;
receiving, with the conversational agent, a second voice input from the patient in response to the third generative voice prompt, wherein the second voice input comprises a second set of medication log data for the patient for the subsequent specified time period; and
recording, with the at least one server, the second set of medication log data for the patient according to the second voice input.

5. The method according to claim 4 further comprising:
receiving, with the at least one server, a second set of blood sugar or hemoglobin A1C data for the patient; and
analyzing, with the at least one server, the second set of blood sugar or hemoglobin A1C data and the second set of medication log data for the patient according to the clinical algorithm.

6. The method according to claim 5 further comprising:
calculating, according to the clinical algorithm, a subsequently titrated dosage amount and/or a subsequently modified dosage frequency for the GLP-1 agonist drug for the patient according to the second set of medication log data for the GLP-1 agonist drug for the patient for the subsequent specified time period and the second set of blood sugar or hemoglobin A1C data for the patient for the subsequent specified time period.

7. The method according to claim 6 further comprising:
configuring, with the at least one server, a fourth generative voice prompt according to the conversational AI model, wherein the fourth generative voice prompt comprises a subsequent dosage instruction for the GLP-1 agonist drug regimen for the patient.

8. The method according to claim 7 wherein the subsequent dosage instruction comprises the subsequently titrated dosage amount and/or the subsequently modified dosage frequency for the GLP-1 agonist drug according to the clinical algorithm.

9. The method according to claim 8 further comprising outputting, with the conversational agent, the fourth generative voice prompt to the patient.

10. The method according to claim 9 further comprising administering, by the patient, a subsequent dose of the GLP-1 agonist drug to the patient in accordance with the subsequent dosage instruction.

11. The method according to claim 4 further comprising:
outputting, with the conversational agent, a fourth generative voice prompt according to the conversational AI model, wherein the fourth generative voice prompt comprises a check-in prompt for the patient.

* * * * *